United States Patent
Chilkoti et al.

(10) Patent No.: US 12,296,018 B2
(45) Date of Patent: May 13, 2025

(54) ALBUMIN BINDING PEPTIDE-DRUG (AlBiPeD) CONJUGATES AND METHODS OF MAKING AND USING SAME

(71) Applicant: Duke University, Durham, NC (US)

(72) Inventors: Ashutosh Chilkoti, Durham, NC (US); Parisa Yousefpour, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 16/964,832

(22) PCT Filed: Jan. 25, 2019

(86) PCT No.: PCT/US2019/015176
§ 371 (c)(1),
(2) Date: Jul. 24, 2020

(87) PCT Pub. No.: WO2019/147954
PCT Pub. Date: Aug. 1, 2019

(65) Prior Publication Data
US 2021/0060171 A1    Mar. 4, 2021

Related U.S. Application Data

(60) Provisional application No. 62/622,249, filed on Jan. 26, 2018.

(51) Int. Cl.
| | | |
|---|---|---|
| A61K 47/64 | (2017.01) | |
| A61K 31/704 | (2006.01) | |
| A61K 47/65 | (2017.01) | |
| A61P 35/00 | (2006.01) | |

(52) U.S. Cl.
CPC ............ *A61K 47/64* (2017.08); *A61K 31/704* (2013.01); *A61K 47/65* (2017.08); *A61P 35/00* (2018.01)

(58) Field of Classification Search
None
See application file for complete search history.

(56) References Cited

U.S. PATENT DOCUMENTS

| | | |
|---|---|---|
| 4,415,732 A | 11/1983 | Caruthers et al. |
| 4,458,066 A | 7/1984 | Caruthers et al. |
| 4,500,707 A | 2/1985 | Caruthers et al. |
| 4,554,101 A | 11/1985 | Hopp |
| 4,668,777 A | 5/1987 | Caruthers et al. |
| 4,973,679 A | 11/1990 | Caruthers et al. |
| 4,976,734 A | 12/1990 | Urry et al. |
| 5,153,319 A | 10/1992 | Caruthers et al. |
| 5,250,516 A | 10/1993 | Urry |
| 5,278,302 A | 1/1994 | Caruthers et al. |
| 5,336,256 A | 8/1994 | Urry |
| 5,453,496 A | 9/1995 | Caruthers et al. |
| 5,534,408 A | 7/1996 | Green et al. |
| 5,578,577 A | 11/1996 | Ching et al. |
| 5,580,859 A | 12/1996 | Felgner et al. |
| 5,602,244 A | 2/1997 | Caruthers et al. |
| 5,676,646 A | 10/1997 | Hofmann et al. |
| 5,679,647 A | 10/1997 | Carson et al. |
| 5,702,359 A | 12/1997 | Hofmann et al. |
| 5,703,055 A | 12/1997 | Felgner et al. |
| 5,935,776 A | 8/1999 | Green et al. |
| 6,068,650 A | 5/2000 | Hofmann et al. |
| 6,096,020 A | 8/2000 | Hofmann |
| 6,120,493 A | 9/2000 | Hofmann |
| 6,150,148 A | 11/2000 | Nanda et al. |
| 6,181,964 B1 | 1/2001 | Hofmann et al. |
| 6,192,270 B1 | 2/2001 | Hofmann et al. |
| 6,207,749 B1 | 3/2001 | Mayes et al. |
| 6,208,893 B1 | 3/2001 | Hofmann |
| 6,216,034 B1 | 4/2001 | Hofmann et al. |
| 6,233,482 B1 | 5/2001 | Hofmann et al. |
| 6,241,701 B1 | 6/2001 | Hofmann |
| 6,245,515 B1 | 6/2001 | Vogelstein et al. |
| 6,296,831 B1 | 10/2001 | Weller et al. |
| 6,302,874 B1 | 10/2001 | Zhang et al. |
| 6,413,587 B1 | 7/2002 | Hawker et al. |
| 6,512,060 B1 | 1/2003 | Matyjaszewski et al. |
| 6,541,580 B1 | 4/2003 | Matyjaszewski et al. |
| 6,623,950 B1 | 9/2003 | Osten et al. |
| 6,649,138 B2 | 11/2003 | Adams et al. |
| 6,660,247 B1 | 12/2003 | Gutowska et al. |
| 6,841,617 B2 | 1/2005 | Jeong et al. |
| 6,852,834 B2 | 2/2005 | Chilkoti |
| 6,869,588 B2 | 3/2005 | Weller et al. |

(Continued)

FOREIGN PATENT DOCUMENTS

| | | |
|---|---|---|
| AU | 2007265628 B2 | 12/2012 |
| CA | 2327325 A1 | 11/1999 |

(Continued)

OTHER PUBLICATIONS

Alves AC, Magarkar A, Horta M, Lima JLFC, Bunker A, Nunes C, Reis S. Influence of doxorubicin on model cell membrane properties: insights from in vitro and in silico studies. Sci Rep. Jul. 24, 2017;7(1):6343 (Year: 2017).*
AACR, "AACR Cancer Progress Report 2016," Clin Cancer Res, Oct. 2016, vol. 22, Issue 19, 143 pages.
Aaron et al., "Elastin as a Random-Network Elastomer—a Mechanical and Optical Analysis of Single Elastin Fibers," Biopolymers, 1981, 20(6):1247-1260.
Abbruzzese et al., "A phase I clinical, plasma, and cellular pharmacology study of gemcitabine," J. Clin. Oncol. 1991, 3, 491-498.
Adams et al., "Safety and utilization of blood components as therapeutic delivery systems," Curr Pharm Biotechnol, 2003, 4(5):275-82.

(Continued)

*Primary Examiner* — Maury A Audet
(74) *Attorney, Agent, or Firm* — Michael Best & Friedrich LLP

(57) ABSTRACT

Described herein are albumin binding peptide drug (AlBiPeD) conjugates comprising a small molecule linked to an albumin binding domain (ABD) via a pH-sensitive linker and methods of purifying and using the same.

Figure 1:
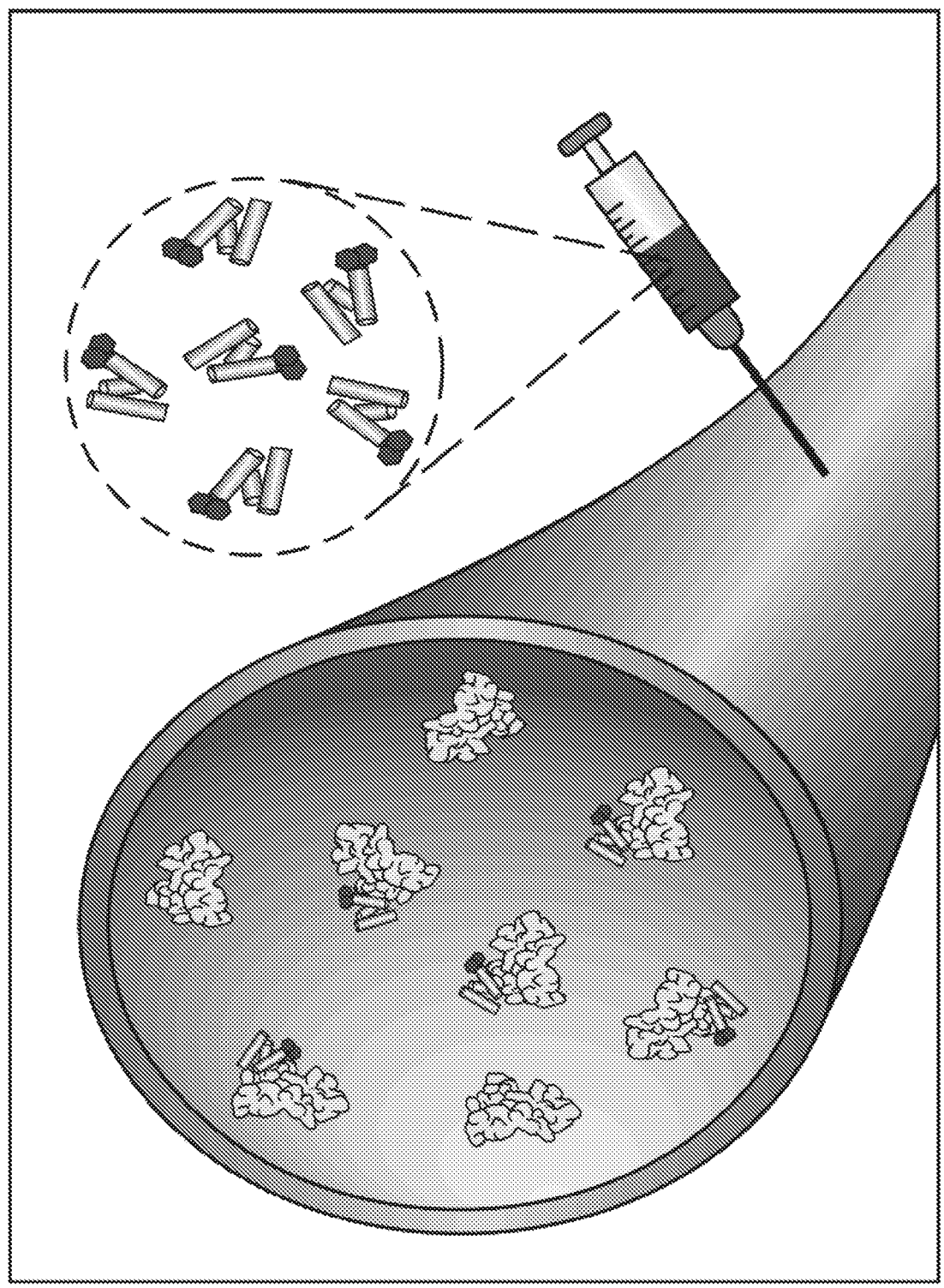

10 Claims, 20 Drawing Sheets
Specification includes a Sequence Listing.

(56) References Cited

U.S. PATENT DOCUMENTS

| | | | |
|---|---|---|---|
| 7,033,571 B2 | 4/2006 | Gutowska et al. |
| 7,087,244 B2 | 8/2006 | Jeong et al. |
| 7,300,922 B2 | 11/2007 | Sullenger et al. |
| 7,429,458 B2 | 9/2008 | Chilkoti |
| 7,531,524 B2 | 5/2009 | Rusconi |
| 7,664,545 B2 | 2/2010 | Westersten et al. |
| 7,674,882 B2 | 3/2010 | Kaplan et al. |
| 8,129,330 B2 | 3/2012 | Martinez et al. |
| 8,283,125 B2 | 10/2012 | Cebolla Ramirez et al. |
| 8,470,967 B2 | 6/2013 | Chilkoti et al. |
| 8,497,356 B2 | 7/2013 | Chilkoti et al. |
| 8,506,963 B2 | 8/2013 | Li et al. |
| 8,586,347 B2 | 11/2013 | Lochhead et al. |
| 8,841,414 B1 | 9/2014 | Raucher et al. |
| 8,912,310 B2 | 12/2014 | Chilkoti et al. |
| 8,937,153 B2* | 1/2015 | Abrahmsen ......... C07K 14/535 |
| | | | 530/324 |
| 9,127,047 B2 | 9/2015 | Chilkoti |
| 9,132,178 B2 | 9/2015 | Philip |
| 9,138,743 B2 | 9/2015 | Yager et al. |
| 9,482,664 B2 | 11/2016 | Chilkoti et al. |
| 9,592,303 B2 | 3/2017 | Chilkoti et al. |
| 9,771,396 B2 | 9/2017 | Chilkoti et al. |
| 9,804,170 B2 | 10/2017 | Krishna et al. |
| 9,890,420 B2 | 2/2018 | Chilkoti et al. |
| 10,064,954 B2 | 9/2018 | Wu |
| 10,131,690 B2* | 11/2018 | Bonny .............. A61K 47/6455 |
| 10,302,636 B2 | 5/2019 | Chilkoti et al. |
| 10,364,451 B2 | 7/2019 | Chilkoti et al. |
| 10,385,115 B2 | 8/2019 | Chilkoti et al. |
| 10,434,182 B2 | 10/2019 | Weng et al. |
| 2001/0034050 A1 | 10/2001 | Chilkoti |
| 2002/0052443 A1 | 5/2002 | Greenwald et al. |
| 2002/0146794 A1 | 10/2002 | Tomycz |
| 2003/0008308 A1 | 1/2003 | Enzelberger et al. |
| 2003/0138829 A1 | 1/2003 | Unger et al. |
| 2003/0175290 A1 | 9/2003 | Renner et al. |
| 2003/0185741 A1 | 10/2003 | Matyjaszewski et al. |
| 2003/0225251 A1 | 12/2003 | Sallberg et al. |
| 2003/0233675 A1 | 12/2003 | Cao et al. |
| 2004/0053976 A1 | 3/2004 | Martinez et al. |
| 2004/0101852 A1 | 5/2004 | Bennett et al. |
| 2004/0192072 A1 | 9/2004 | Snow et al. |
| 2005/0186214 A1 | 8/2005 | Liu et al. |
| 2005/0255554 A1 | 11/2005 | Chilkoti |
| 2005/0288229 A1 | 12/2005 | Sindrey et al. |
| 2006/0025524 A1 | 2/2006 | Schneider et al. |
| 2006/0034796 A1 | 2/2006 | Ashwell et al. |
| 2006/0051798 A1 | 3/2006 | Mirkin et al. |
| 2007/0087114 A1 | 4/2007 | Chilkoti et al. |
| 2007/0117173 A1 | 5/2007 | Levison et al. |
| 2008/0181861 A1 | 7/2008 | Jiang et al. |
| 2009/0098652 A1 | 4/2009 | Stupp et al. |
| 2009/0215194 A1 | 8/2009 | Magni et al. |
| 2009/0247424 A1 | 10/2009 | Chilkoti et al. |
| 2010/0015070 A1 | 1/2010 | Bollschweiler et al. |
| 2010/0022455 A1 | 1/2010 | Chilkoti |
| 2010/0048473 A1 | 2/2010 | Chaikof et al. |
| 2010/0120018 A1 | 5/2010 | Quake et al. |
| 2010/0241054 A1 | 9/2010 | Dacey et al. |
| 2010/0311059 A1 | 12/2010 | Didion et al. |
| 2010/0311669 A1 | 12/2010 | Greene et al. |
| 2010/0325765 P1 | 12/2010 | Pait et al. |
| 2011/0082283 A1 | 4/2011 | Dagher et al. |
| 2011/0119778 A1 | 5/2011 | Liss |
| 2011/0165557 A1 | 7/2011 | Ah et al. |
| 2011/0207673 A1 | 8/2011 | Chilkoti et al. |
| 2011/0248698 A1 | 10/2011 | Kikuchi et al. |
| 2011/0294189 A1 | 12/2011 | Chilkoti et al. |
| 2011/0303303 A1 | 12/2011 | Proper et al. |
| 2011/0305718 A1 | 12/2011 | Mugica et al. |
| 2012/0172298 A1 | 7/2012 | Andersen et al. |
| 2012/0208742 A1 | 8/2012 | Primiano et al. |
| 2013/0039927 A1 | 2/2013 | Dewhurst et al. |
| 2013/0079277 A1 | 3/2013 | Chilkoti |
| 2013/0079280 A1 | 3/2013 | Baca et al. |
| 2013/0096058 A1 | 4/2013 | Baca et al. |
| 2013/0102993 A1 | 4/2013 | Kim et al. |
| 2013/0130384 A1 | 5/2013 | Okamoto et al. |
| 2013/0157889 A1 | 6/2013 | Chilkoti et al. |
| 2013/0165389 A1 | 6/2013 | Schellenberger et al. |
| 2013/0172274 A1 | 7/2013 | Chilkoti |
| 2013/0197359 A1 | 8/2013 | Park et al. |
| 2013/0315823 A1 | 11/2013 | Trieu |
| 2013/0330335 A1 | 12/2013 | Bremel et al. |
| 2014/0024600 A1 | 1/2014 | Chilkoti et al. |
| 2014/0163201 A1 | 6/2014 | Winter et al. |
| 2014/0275227 A1 | 9/2014 | Hoge et al. |
| 2014/0294932 A1 | 10/2014 | Kim et al. |
| 2015/0094270 A1 | 4/2015 | Harris et al. |
| 2015/0099707 A1 | 4/2015 | Pastan et al. |
| 2015/0112022 A1 | 4/2015 | Chilkoti et al. |
| 2016/0017278 A1 | 1/2016 | Montclare et al. |
| 2016/0114053 A1 | 4/2016 | Chilkoti |
| 2016/0120952 A1 | 5/2016 | Chilkoti |
| 2016/0200787 A1 | 7/2016 | Matern et al. |
| 2016/0209356 A1 | 7/2016 | Herget et al. |
| 2016/0220727 A1 | 8/2016 | Lu et al. |
| 2016/0250165 A1 | 9/2016 | Sullenger et al. |
| 2016/0271262 A1 | 9/2016 | Lopez et al. |
| 2016/0303091 A1 | 10/2016 | Wang |
| 2016/0348147 A1 | 12/2016 | Lopez et al. |
| 2016/0355802 A1 | 12/2016 | Isaacs et al. |
| 2017/0088670 A1 | 3/2017 | Rowan et al. |
| 2017/0102357 A1 | 4/2017 | Liang et al. |
| 2017/0166621 A1 | 6/2017 | Boettcher et al. |
| 2017/0170142 A1 | 6/2017 | Edelstein et al. |
| 2017/0189545 A1 | 7/2017 | Lee et al. |
| 2017/0233714 A1 | 8/2017 | Chilkoti et al. |
| 2017/0239363 A1 | 8/2017 | Chilkoti et al. |
| 2017/0369651 A1 | 12/2017 | Cheng et al. |
| 2018/0135060 A1 | 5/2018 | Romero Ramos et al. |
| 2018/0161772 A1 | 6/2018 | Rammohan et al. |
| 2018/0171337 A1 | 6/2018 | O'Neill et al. |
| 2018/0200196 A1 | 7/2018 | Fahmy et al. |
| 2018/0217136 A1 | 8/2018 | Chilkoti et al. |
| 2018/0231469 A1 | 8/2018 | Gibbons et al. |
| 2018/0238864 A1 | 8/2018 | Burd et al. |
| 2018/0258157 A1 | 9/2018 | Chilkoti et al. |
| 2018/0326044 A1 | 11/2018 | Carter |
| 2018/0327752 A1 | 11/2018 | Pillay et al. |
| 2018/0369399 A1 | 12/2018 | Hershfield et al. |
| 2019/0016763 A1 | 1/2019 | Kitazawa et al. |
| 2019/0204309 A1 | 7/2019 | Gibbs |
| 2019/0285623 A1 | 9/2019 | Chilkoti et al. |
| 2019/0292549 A1 | 9/2019 | Zhang et al. |
| 2019/0345228 A1 | 11/2019 | Chilkoti et al. |
| 2020/0030496 A1 | 1/2020 | Reddy et al. |
| 2020/0078313 A1 | 3/2020 | Roy et al. |
| 2020/0121809 A1 | 4/2020 | Hope et al. |
| 2020/0148724 A1 | 5/2020 | Chilkoti et al. |
| 2020/0163878 A1 | 5/2020 | Baumhof et al. |
| 2020/0181555 A1 | 6/2020 | Hinojosa et al. |
| 2021/0128734 A1 | 5/2021 | Chilkoti et al. |
| 2021/0154143 A1 | 5/2021 | Chilkoti et al. |
| 2023/0225998 A1 | 7/2023 | Mansour et al. |

FOREIGN PATENT DOCUMENTS

| | | |
|---|---|---|
| CA | 2423488 A1 | 4/2002 |
| CN | 102575229 A | 7/2012 |
| CN | 104725628 B | 4/2018 |
| CN | 112961065 A | 6/2021 |
| EP | 1670315 B1 | 4/2017 |
| EP | 2664340 B1 | 2/2020 |
| JP | 2014-156428 A | 8/2014 |
| JP | 2014-534265 A | 12/2014 |
| WO | WO1991/019813 A1 | 12/1991 |
| WO | WO2003/040165 A2 | 10/2002 |
| WO | WO2004/096124 A2 | 11/2004 |
| WO | WO2006/004778 A2 | 1/2006 |
| WO | 2006/110292 A2 | 10/2006 |
| WO | WO2007/073486 A2 | 6/2007 |
| WO | WO2007/108013 A2 | 9/2007 |

(56) References Cited

FOREIGN PATENT DOCUMENTS

| WO | WO2007/134245 A2 | 11/2007 |
|---|---|---|
| WO | 2008/012543 A1 | 1/2008 |
| WO | 2008/030968 A2 | 3/2008 |
| WO | WO2009/067584 A1 | 5/2009 |
| WO | WO2010/054699 A1 | 5/2010 |
| WO | WO2010/057154 A1 | 5/2010 |
| WO | WO2010/096422 A1 | 8/2010 |
| WO | 2011/025572 A1 | 3/2011 |
| WO | WO2011/123813 A2 | 10/2011 |
| WO | 2012/156058 A1 | 11/2012 |
| WO | 2012/162426 A1 | 11/2012 |
| WO | WO2013/049234 A2 | 4/2013 |
| WO | WO2013/065009 A1 | 5/2013 |
| WO | 2013/106715 A1 | 7/2013 |
| WO | WO2014/037373 A1 | 3/2014 |
| WO | WO2014/194244 A1 | 12/2014 |
| WO | 2015/011231 A1 | 1/2015 |
| WO | WO2015/130846 A2 | 9/2015 |
| WO | 2016/065300 A1 | 4/2016 |
| WO | WO2016/065273 A1 | 4/2016 |
| WO | WO2016/090103 A1 | 6/2016 |
| WO | WO2016/154530 A1 | 9/2016 |
| WO | WO2017/015132 A1 | 1/2017 |
| WO | WO2017/024182 A1 | 2/2017 |
| WO | WO2017/112825 A2 | 6/2017 |
| WO | WO2017/112826 A2 | 6/2017 |
| WO | WO2017/192449 A1 | 11/2017 |
| WO | WO2018/115401 A1 | 6/2018 |
| WO | WO2018/144854 A1 | 8/2018 |
| WO | 2019/103744 A1 | 5/2019 |
| WO | WO2019/147954 A1 | 8/2019 |
| WO | 2020/037100 A1 | 2/2020 |
| WO | 2020/037214 A1 | 2/2020 |
| WO | 2020/051223 A1 | 3/2020 |
| WO | 2020/160472 A1 | 8/2020 |
| WO | 2021/178898 A1 | 9/2021 |
| WO | 2022/016089 A2 | 1/2022 |
| WO | 2022/178438 A1 | 8/2022 |
| WO | 2022/066635 A1 | 3/2023 |

OTHER PUBLICATIONS

Adams et al., "Sustained release of antibiotics from injectable and thermally responsive polypeptide depots," J Biomed Mater Res B Appl Biomater, Jul. 2009, vol. 90B, Issue 1, pp. 67-74.

Adamska et al., "Pancreatic ductal adenocarcinoma: Current and evolving therapies," J Mol Sci, Jun. 2017, vol. 18, Issue 7, pp. 1338-1380.

Adiseshaiah et al., "Nanomedicine strategies to overcome the pathophysiological barriers of pancreatic cancer," Nat Rev Clin Oncol, Dec. 2016, vol. 13, Issue 12, pp. 750-765.

Aladini et al., "Chemical Synthesis and Characterization of Elastin-Like Polypeptides (ELPs) With Variable Guest Residues," J Pept Sci, May 2016, vol. 22, Issue 5, pp. 334-342.

Alarcon et al., "Exendin 4 controls insulin production in rat islet beta cells predominantly by potentiation of glucose-stimulated proinsulin biosynthesis at the translational level," Diabetologia, 2006, 49(12):2920-2929.

Albanese et al., "The effect of nanoparticle size, shape, and surface chemistry on biological systems," Annu. Rev. Biomed. Eng., Aug. 2012, vol. 14, pp. 1-16.

Alconcel et al., "FDA-approved poly(ethylene glycol)-protein conjugate drugs," Polym. Chem., vol. 2, Apr. 2011, Issue 7, pp. 1442-1448.

Allen et al., "Liposomal drug delivery systems: from concept to clinical applications," Adv Drug Deliv Rev, Elsevier, Jan. 2013, 65(1):36-48.

Alley et al., "Feasibility of drug screening with panels of human tumor cell lines using a microculture tetrazolium assay," Cancer Res., 1988, 48, 589-601.

Aluri et al., "Elastin-like peptide amphiphiles Form nanofibers with tunable length," Biomacromolecules, Sep. 2012, vol. 13, Issue 9, pp. 2645-2654.

American Diabetes Association, Standards of medical care in diabetes—2018. Diabetes Care, Jan. 2018, vol. 41, Supplement 1, pp. S1-S159.

Amiram et al., "A depot-forming glucagon-like peptide-1 fusion protein reduces blood glucose for five days with a single injection," J. Control. Release, Nov. 2013, vol. 172, Issue, pp. 144-151.

Amiram et al., "Injectable protease-operated depots of glucagon-like peptide-1 provide extended and tunable glucose control," Proc. Natl. Acad. Sci., Feb. 2013, vol. 110, Issue 8, pp. 2792-2797.

Andersen et al., "Extending Half-life by Indirect Targeting of the Neonatal Fc Receptor (FcRn) Using a Minimal Albumin Binding Domain," Journal of Biological Chemistry, Feb. 2011, vol. 286, Issue 7, pp. 5234-5241.

Anselmo et al., "Nanoparticles in the clinic," Bioeng Transl Med, Jun. 2016, 1(1):10-29.

Antos et al., "Lipid Modification of Proteins through Sortase-Catalyzed Transpeptidation," J. Am. Chem. Soc., Dec. 2008, vol. 130, Issue 48, pp. 16338-16343.

Antos et al., "Site-Specific N- and C-Terminal Labeling of a Single Polypeptide Using Sortases of Different Specificity," J. Am. Chem. Soc., Aug. 2009, vol. 131, Issue 31, pp. 10800-10801.

Arami et al., "In vivo delivery, pharmacokinetics, biodistribution and toxicity of iron oxide nanoparticles," Chem Soc Rev, Dec. 2015, 44(23):8576-8607.

Arias et al., "Superior preclinical efficacy of gemcitabine developed as chitosan nanoparticulate system," Biomacromolecules, Jan. 2011, vol. 12, Issue 1, pp. 97-104.

Armstrong et al., "Antibody against poly(ethylene glycol) adversely affects PEG-asparaginase therapy in acute lymphoblastic leukemia patients," Cancer, Jul. 2007, vol. 110, Issue 1, pp. 103-111.

Armstrong et al., "The Hydrodynamic Radii of Macromolecules and Their Effect on Red Blood Cell Aggregation," Biophys. J., 2004, 87, 4259-4270.

Arner et al., "FGF21 attenuates lipolysis in human adipocytes—a possible link to improved insulin sensitivity," FEBS Lett, May 2008, vol. 582, Issue 12, pp. 1725-1730.

Arnida et al., "Geometry and surface characteristics of gold nanoparticles influence their biodistribution and uptake by macrophages," Eur J Pharm Biopharm, Apr. 2011, vol. 77, Issue 3, pp. 417-423.

Asai et al., "Protein polymer hydrogels by in situ, rapid and reversible self-gelation," Biomaterials, Jul. 2012, vol. 33, Issue 21, pp. 5451-5458.

Astete et al., "Synthesis and characterization of PLGA nanoparticles," Journal of Biomaterials Science, Polymer Edition 2006, 17(3):247-289.

Atun et al., "Expanding global access to radiotherapy," Lancet Oncol, Sep. 2015, vol. 16, Issue 10, pp. 1153-1186.

Averick et al., "ATRP under biologically relevant conditions: grafting from a protein," ACS Macro. Lett., Jan. 2012, vol. 1, Issue 1, pp. 6-10.

Averick et al., "Protein-polymer hybrids: conducting ARGET ATRP from a genetically encoded cleavable ATRP initiator," Eur. Polym. J., Oct. 2013, vol. 49, Issue 10, pp. 2919-2924.

Awai et al., "Studies of the metabolism of I-131-labeled human transferrin," J. Lab. Clin. Med. 61, 1963, 363-396.

Awasthi et al., "Comparative benefits of Nab-paclitaxel over gemcitabine or polysorbate-based docetaxel in experimental pancreatic cancer," Carcinogenesis, Oct. 2013, vol. 34, Issue 10, pp. 2361-2369.

Awasthi et al., "Evaluation of combination treatment benefits of nab-paclitaxel in experimental pancreatic cancer," Journal of Clinical Oncology, 2012, 30, 170.

Axup et al., "Synthesis of site-specific antibody-drug conjugates using unnatural amino acids," Proc Natl Acad Sci USA, Feb. 2012, vol. 109, Issue 40, pp. 16101-16106.

Azhdarinia et al., "Regional radiochemotherapy using in situ hydrogel," Pharm Res., 2005, 22, 776-783.

Babu, "The contribution of intrinsically disordered regions to protein function, cellular complexity, and human disease," Biochem Soc Trans, Oct. 2016, 44(5):1185-1200.

Bache et al., "Investigating the accuracy of microstereotactic-body-radiotherapy utilizing anatomically accurate 3D printed rodent-morphic dosimeters," Medical Physics, Feb. 2015, vol. 42, Issue 2, pp. 846-855.

(56) References Cited

OTHER PUBLICATIONS

Badi, "Non-linear PEG-based thermoresponsive polymer systems," Progress in Polymer Science, Mar. 2017, vol. 66, pp. 54-79.

Bae et al., "Targeted drug delivery to tumors: myths, reality and possibility," J Control Release, Elsevier, Aug. 2011, 153(3):198-205.

Baggio et al., "A recombinant human glucagon-like peptide (GLP)-1-albumin protein (Albugon) mimics peptidergic activation of GLP-1 receptor-dependent pathways coupled with satiety, gastrointestinal motility, and glucose homeostasis," Diabetes 53, 2004, 2492-2500.

Baggio et al., "Biology of Incretins: GLP-1 and GIP," Gastroenterology, May 2007, vol. 132, Issue 6, pp. 2131-2157.

Bailey et al., "Genomic analyses identify molecular subtypes of pancreatic cancer," Nature, Mar. 2016, vol. 531, Issue 7592, pp. 47-52.

Balu et al., "An16-resilin: an advanced multi-stimuli-responsive resilin-mimetic protein polymer," Acta Biomater, Nov. 2014, 10:4768-4777.

Bamford et al., "The COSMIC (Catalogue of Somatic Mutations in Cancer) database and website," British Journal of Cancer, 2004, 91, 355-358.

Banani et al., "Biomolecular condensates: organizers of cellular biochemistry," Nat Rev Mol Cell Biol, May 2017, 18(5):285-298.

Banerjee et al., "Nanoparticles in cancer chemotherapy," Prog Mol Biol Transl Sci, Elsevier, Nov. 2011, 104:489-507.

Banga et al., "Parenteral controlled delivery and parmacokinetics of therapeutic peptides and proteins," (CRC Press, Boca Raton, FL, 2005).

Banjade et al., "Phase transitions of multivalent proteins can promote clustering of membrane receptors," Elife, Oct. 2014, 3:e04123.

Bansal et al., "PEGylation improves pharmacokinetic profile, liver uptake and efficacy of Interferon gamma in liver fibrosis," J. Control. Release, Sep. 2011, vol. 154, Issue 3, pp. 233-240.

Banskota et al., "Genetically encoded stealth nanoparticles of a zwitterionic polypeptide-paclitaxel conjugate have wider therapeutic window than Abraxane in multiple tumor models," Nano Lett, Mar. 2020, 20(4):2396-2409.

Barbuti et al., "Paclitaxel through the ages of anticancer therapy: Exploring its role in chemoresistance and radiation therapy," Cancers, Dec. 2015, vol. 7, Issue 4, pp. 2360-2371.

Barnett et al., "Normal tissue reactions to radiotherapy: towards tailoring treatment dose by genotype," Nat Rev Cancer, Feb. 2009, vol. 9, Issue 2, pp. 134-142.

Barton et al., "Estimating the demand for radiotherapy form the evidence: A review of changes from 2003 to 2012," Radiother Oncol, Jul. 2014, vol. 112, Issue 1, pp. 140-144.

Baskar et al., "Cancer and Radiation Therapy: Current Advances and Future Directions," Int. J. Med. Sci., Feb. 2012, vol. 9, Issue 3, pp. 193-199.

Bates et al., "Block copolymer thermodynamics: theory and experiment," Annu Rev. Phys. Chem., 1990, 41:525-57.

Bedford et al., "WW domain-mediated interactions reveal a spliceosome-associated protein that binds a third class of proline-rich motif: The proline glycine and methionine-rich motif," PNAS, 1998, 95: 10602-10607.

Beenken et al., "The FGF family: biology, pathophysiology and therapy," Nat Rev Drug Discov, Mar. 2009, vol. 8, Issue 3, pp. 235-253.

Begg et al., "Strategies to improve radiotherapy with targeted drugs," Nat Rev Cancer, Apr. 2011, vol. 11, Issue 4, pp. 239-253.

Bellucci et al., "A noncanonical function of sortase enables site-specific conjugation of small molecules to lysine residues in proteins," Angew. Chem. Int. Ed. 54, Jan. 2015, vol. 54, Issue 2, pp. 441-445.

Bellucci et al., "Three-in-One Chromatography-Free Purification, Tag Removal, and Site-Specific Modification of Recombinant Fusion Proteins Using Sortase A and Elastin-like Polypeptides," Angewandte Chemie International Edition, Mar. 2013, vol. 52, Issue 13, pp. 3703-3708.

Bender et al., "Synthesis, Crystallization, and Biological Evaluation of an Orally Active Prodrug of Gemcitabine," J. Med. Chem., Nov. 2009, vol. 52, Issue 22, pp. 6958-6961.

Berisio et al., "Imino Acids and Collagen Triple Helix Stability: Characterization of Collagen-like Polypeptides Containing Hyp-Hyp-Gly Seqeucne Repeats," JACS, 2004, 126: 11402-11403.

Bernacki et al., "Length-dependent aggregation of uninterrupted polyalanine peptides," Biochemistry, Sep. 2011, vol. 50, Issue 43, pp. 9200-9211.

Berndt et al., "Synthetic lipidation of peptides and amino acids: Monolayer structure and properties," J. Am. Chem. Soc., 1995, 117, 9515-9522.

Bessa et al., "Thermoresponsive self-assembled elastin-based nanoparticles for delivery of BMPs," Journal of Controlled Release, Mar. 2010, vol. 142, Issue 3, pp. 312-318.

Best, "Computational and theoretical advances in studies of intrinsically disordered proteins," Curr Opin Struct Biol, Feb. 2017, 42:147-154.

Bhattacharyya et al., "A paclitaxel-loaded recombinant polypeptide nanoparticle outperforms Abraxane in multiple murine cancer models," Nat. Commun., Aug. 2015, Issue 6, Article 7939, 30 pages.

Bhattacharyya et al., "Encapsulating a Hydrophilic Chemotherapeutic into Rod-Like Nanoparticles of a Genetically Encoded Asymmetric Triblock Polypeptide Improves its Efficacy," Advanced functional materials, Mar. 2017, vol. 27, Issue 12, Article 1605421, 9 pages.

Bidwell et al., "Development of elastin-like polypeptide for thermally targeted delivery of doxorubicin," Biochemical Pharmacology, Mar. 2007, vol. 73, Issue 5, pp. 620-631.

Binz et al., "Engineering novel binding proteins from nonimmunoglobulin domains," Nat Biotechnol, 2005, 23(10):1257-68.

Blanco et al., "Principles of nanoparticle design for overcoming biological barriers to drug delivery," Nat Biotechnol, Sep. 2015, 33(9):941-51.

Blasko et al., "Brachytherapy for carcinoma of the prostate: Techniques, patient selection, and clinical outcomes," Seminars in Radiation Oncology, 2002, 12, 81-94.

Blasko et al., "The role of external beam radiotherapy with I-125/Pd-103 brachytherapy for prostate carcinoma," Radiother Oncol, 2000, 57, 273-278.

Blasko et al., "Transperineal percutaneous iodine-125 implantation for prostatic carcinoma using transrectal ultrasound and template guidance," Endocurietherapy/Hyperthermia Oncology, 1987, 3, 131-139.

Bley et al., "Microtubule stabilising agents and ionising radiation: Multiple exploitable mechanisms for combined treatment," Eur J Cancer, Jan. 2013, vol. 49, Issue 1, pp. 245-253.

Bobo et al., "Nanoparticle-based medicines: a review of FDA-approved materials and clinical trials to date." Pharmaceutical research, Oct. 2016, vol. 33, Issue 10, pp. 2373-2387.

Bocci et al., "The pharmacological bases of the antiangiogenic activity of paclitaxel," Angiogenesis, Jul. 2013, vol. 16, Issue 3, pp. 481-492.

Bochicchio et al., "Investigating by CD the molecular mechanism of elasticity of elastomeric proteins," Chirality, Sep. 2008, vol. 20, Issue 9, pp. 985-994.

Boekhorst et al., "Genome-wide detection and analysis of cell wall-bound proteins with LPxTG-like sorting motifs," J. Bacteriol. 187, 2005, 4928-4934.

Boeynaems et al., "Protein Phase Separation: A New Phase in Cell Biology," Trends Cell Biol, Jun. 2018, 28(6):420-435.

Boldt, "Use of albumin: an update," Br J. Anaesth., Mar. 2010, vol. 104, Issue 3, pp. 276-284.

Bond, "Exenatide (Byetta) as a novel treatment option for type 2 diabetes mellitus," Proc. (Bayl. Univ. Med. Cent.), Jul. 2006, vol. 19, Issue 3, pp. 281-284.

Bontempo et al., "Streptavidin as a macroinitiator for polymerization: in situ protein-polymer conjugate formation," J. Am. Chem. Soc., 2005, 6508-6509.

Borst et al., "The Therapeutic Antibody LM609 Selectively Inhibits Ligand Binding to Human αVβ3 Integrin via Steric Hindrance," Structure, Nov. 2017, 25(11):1732-1739.e5.

(56) References Cited

OTHER PUBLICATIONS

Bowditch et al., "Identification of a novel integrin binding site in fibronectin. Differential utilization by β3 integrins," Journal of Biological Chemistry, 1994, 269(14):10856-10863.
Boyer et al., "Well-Defined Protein-Polymer Conjugates via in Situ RAFT Polymerization," J. Am. Chem. Soc., Jun. 2007, vol. 129, Issue 22, pp. 7145-7154.
Branco et al., "Self-assembling materials for therapeutic delivery," Acta Biomaterialia, Mar. 2009, vol. 5, Issue 3, pp. 817-831.
Brangwynne et al., "Polymer physics of intracellular phase transitions," Nature Physics, Nov. 2015, 11(11):899-904.
Brannon-Peppas et al., "Nanoparticle and targeted systems for cancer therapy," Advanced Drug Delivery Reviews, Elsevier, Sep. 2012, 64(11):206-212.
Broome et al., "Expanding the utility of beta-galactosidase complementation: piece by piece," Mol Pharm, ACS Publications, Feb. 2010, 7(1):60-74.
Broyer et al., "Emerging synthetic approaches for protein-polymer conjugations," Chem. Commun., Feb. 2011, vol. 47, Issue 8, pp. 2212-2226.
Brusa et al., "Antitumor activity and pharmacokinetics of liposomes containing lipophilic gemcitabine prodrugs," Anticancer Res., Jan. 2007, vol. 27, Issue 1A, pp. 195-199.
Burchard, "Light Scattering Techniques," Physical techniques for the study of food biopolymers, 1994, 151-213.
Burke et al., "Multimodal nanoparticle imaging agents: design and applications," Philos Trans A Math Phys Eng Sci, Nov. 2017, 375:20170261.
Burnouf, "Modern plasma fractionation," Transfus. Med. Rev., Apr. 2007, vol. 21, Issue 2, pp. 101-117.
Buteau et al., "Glucagon-like peptide-1 prevents beta cell glucolipotoxicity," Diabetologia, 2004, 47(5):806-815.
Butler et al., "β-Cell Deficit and Increased β-Cell Apoptosis in Humans With Type 2 Diabetes," Diabetes, 2003, 52(1):102-110.
Cabral et al., "Accumulation of sub-100 nm polymeric micelles in poorly permeable tumours depends on size," Nature Nanotechnology, Oct. 2011, vol. 6, Issue 12, pp. 815-823.
Cabrera et al., "Automated, High-Throughput Assays for Evaluation of Human Pancreatic Islet Function," Cell Transplant, First published Nov. 2007, vol. 16, Issue 10, pp. 1039-1048.
Cabrera et al., "Glutamate Is a Positive Autocrine Signal for Glucagon Release," Cell Metab, Jun. 2008, vol. 7, Issue 6, pp. 545-554.
Cai et al., "Long-acting preparations of exenatide," Drug Des. Devel. Ther., Sep. 2013, vol. 7, pp. 963-970.
Caliceti et al., "Pharmacokinetic and biodistribution properties of poly(ethylene glycol)-protein conjugates," Adv. Drug Deliv. Rev, 2003, 55, 1261-1277.
Callahan et al., "Triple stimulus-responsive polypeptide nanoparticles that enhance intratumoral spatial distribution," Nano Letters, Mar. 2012, vol. 12, Issue 4, pp. 2165-2170.
Camilloni et al., "Determination of secondary structure populations in disordered states of proteins using nuclear magnetic resonance chemical shifts," Biochemistry, Feb. 2012, vol. 51, Issue 11, pp. 2224-2231.
Campbell et al., "Pegylated peptides V. Carboxy-terminal PEGlyted analogs of growth hormone- releasing factor (GRF) display enhanced duration of biological activity in vivo," J. Peptide Res., 1997, 49:527-537.
Cao et al., "Monitoring the effects of anti-angiogenesis on the radiation sensitivity of pancreatic cancer xenografts using dynamic contrast-enhanced computed tomography," Int J Radiation Oncol Biol Phys, Feb. 2014, vol. 88, Issue 2, pp. 412-418.
Cardenes et al., "Locally advanced pancreatic cancer: Current therapeutic approach," The Oncologist, Jun. 2006, vol. 11, Issue 6, pp. 612-623.
Carreiras et al., "Expression and localization of alpha v integrins and their ligand vitronectin in normal ovarian epithelium and in ovarian carcinoma," Gynecol Oncol, 1996, 62(2):260-7.
Carrico et al., "Introducing genetically encoded aldehydes into proteins," Nat Chem Biol, Jun. 2007, vol. 3, Issue 6, pp. 321-322.
Cataldo et al., "Radiation-induced crosslinking of collagen gelatin into a stable hydrogel," Journal of Radioanalytical and Nuclear Chemistry, Sep. 2008, vol. 275, Issue 1, pp. 125-131.
Centers for Disease Control and Prevention, "National Diabetes Statistics Report, 2017," Atlanta, GA: Centers for Disease Control and Prevention, US Department of Health and Human Services; 2017. Reviewed: Feb. 24, 2018.
Ceska et al., "A new and rapid method for the clinical determination of α-amylase activities in human serum and urine. Optimal conditions," Clinica Chimica Acta, 1969, 26, 437-444.
Chakrabartty et al., "Stability of α-Helices," Adv Protein Chem, 1995, 46, 141-176.
Champion et al., "Particle shape: a new design parameter for micro- and nanoscale drug delivery carriers," J Control Release, Elsevier, Aug. 2007, 121(1-2):3-9.
Champion et al., "Role of particle size in phagocytosis of polymeric microspheres," Pharm Res, Srpinger, Mar. 2008, 25(8):1815-21.
Champion et al., "Role of target geometry in phagocytosis," Proc Natl Acad Sci U S A, The National Academy of Sciences of the USA, Mar. 2006, 103(13):4930-4.
Champion et al., "Shape induced inhibition of phagocytosis of polymer particles," Pharm Res, Springer, Jan. 2009, 26(1):244-9.
Chang et al., "Tumor-stroma interaction in orthotopic primary pancreatic cancer xenografts during hedgehog pathway inhibition," Int. J. Cancer, Jul. 2013, vol. 133, Issue 1, pp. 225-235.
Chatterjee et al., "Type 2 diabetes," The Lancet, Jun. 2017, vol. 389, Issue 10085, pp. 2239-2251.
Chaudhury et al., "The major histocompatibility complex-related Fc receptor for IgG (FcRn) binds albumin and prolongs its lifespan," J Exp Med, 2003, 197(3): p. 315-322.
Chen et al., "Anisotropic hydrogels fabricated with directional freezing and radiation-induced polymerization and crosslinking method," Materials Letters, Dec. 2012, vol. 89, pp. 104-107.
Chen et al., "Anti-hypervariable region antibody induced by a defined peptide: An approach for studying the structural correlates of idiotypes," PNAS, 1984, 81:1784-1788.
Chen et al., "Bioinspired Modular Synthesis of Elastin-Mimic Polymers to Probe the Mechanism of Elastin Elasticity," J. Am. Chem. Soc., Mar. 2010, vol. 132, Issue 13, pp. 4577-4579.
Chen et al., "Rheology of Soft Materials," Annual Review of Condensed Matter Physics, May 2010, vol. 1, pp. 301-322.
Chen et al., "Site-specific labeling of cell surface proteins with biophysical probes using biotin ligase," Nat Methods, 2005, 2(2):99-104.
Chen et al., "The use of self-adjuvanting nanofiber vaccines to elicit high-affinity B cell responses to peptide antigens without inflammation," Biomaterials, Nov. 2013, vol. 34, Issue 34, pp. 8776-8785.
Chen, "Small-molecule delivery by nanoparticles for anticancer therapy," Trends Mol Med, Cell Press, Dec. 2010, 16(12):594-602.
Chilkoti et al., "Design of thermally responsive, recombinant polypeptide carriers for targeted drug delivery," Advance Drug Delivery Reviews, 2002, 54:1093-1111.
Chilkoti et al., "Stimulus responsive elastin biopolymers: applications in medicine and biotechnology," Curr Opin Chem Biol, Dec. 2006, vol. 10, Issue 6, pp. 652-657.
Chilkoti et al., "Targeted drug delivery by thermally responsive polymers," Advanced Drug Delivery Reviews, 2002, 54:613-630.
Chithrani et al., "Determining the size and shape dependence of gold nanoparticle uptake into mammalian cells," Nano Lett, Apr. 2006, vol. 6, Issue 4, pp. 662-668.
Chithrani et al., "Elucidating the mechanism of cellular uptake and removal of protein-coated gold nanoparticles of different sizes and shapes," Nano letters, ACS Publications, Jun. 2007, 7(6):1542-1550.
Chitkara et al., "Self-Assembling, Amphiphilic Polymer—Gemcitabine Conjugate Shows Enhanced Antitumor Efficacy Against Human Pancreatic Adenocarcinoma," Bioconjug. Chem., Jun. 2013, vol. 24, Issue 7, pp. 1161-1173.
Cho et al., "Effects of hofmeister anions on the phase transition temperature of elastin-like polypeptides," J. Phys. Chem. B., Nov. 2008, vol. 112, Issue 44, pp. 13765-13771.

(56) References Cited

OTHER PUBLICATIONS

Cho et al., "Hydrogen bonding of β-turn structure is stabilized in D(2)O," J Am Chem Soc, Oct. 2009, vol. 131, Issue 42, pp. 15188-15193.

Cho et al., "Therapeutic nanoparticles for drug delivery in cancer," Clin. Cancer Res., Mar. 2008, vol. 14, Issue 5, pp. 1310-1316.

Chockalingam et al., "Design and application of stimulus-responsive peptide systems," Protein Engineering, Design & Selection, Apr. 2007, 20(4):155-161.

Choi et al., "Renal Clearance of Nanoparticles," Nature biotechnology, Oct. 2007, vol. 25, Issue 10, pp. 1165-1170.

Chow et al., "Peptide-based biopolymers in biomedicine and biotechnology," Mater. Sci. Eng. R Reports, Jan. 2008, vol. 62, Issue 4, pp. 125-155.

Chow et al., "Ultra-High Expression of a Thermally Responsive Recombinant Fusion Protein in E. coli," Biotechnology Progress, Sep. 2006, vol. 22, Issue 3, pp. 638-646.

Choy et al., "Investigation of taxol as a potential radiation sensitizer," Cancer, 1993, 71, 3774-3778.

Christensen et al., "Fusion order controls expression level and activity of elastin-like polypeptide fusion proteins," Protein Science, Jul. 2009, vol. 18, Issue 7, pp. 1377-1387.

Christensen et al., "Predicting Transition Temperatures of Elastin-Like Polypeptide Fusion Proteins," Biomacromolecules, Mar. 2013, vol. 14, Issue 5, pp. 1514-1519.

Cid-Arregui et al., "Perspectives in the treatment of pancreatic adenocarcinoma," World Journal of Gastroenterology, Aug. 2015, vol. 21, Issue 31, pp. 9297-9316.

Ciezki et al., "Brachytherapy or surgery? A composite view," Oncology, Oct. 2009, vol. 23, Issue 11, pp. 960-964.

Cima, "AVMA Guidelines for the Euthanasia of Animal: 2013 Edition," Journal of the American Veterinary Medical Association, Jan. 2013, vol. 242, 102 pages.

Cirulis et al., "Viscoelastic properties and gelation of an elastin-like polypeptide," Journal of Rheology, Sep. 2009, vol. 53, Issue 5, pp. 1215-1228.

Clarke et al., "Tropoelastin massively associates during coacervation to form quantized protein spheres," Biochemistry, Jul. 2006, vol. 45, Issue 33, pp. 9989-9996.

Clavéet al., "Amylase, lipase, pancreatic isoamylase, and phospholipase A in diagnosis of acute pancreatitis," Clinical Chemistry, 1995, 41, 1129-1134.

Coin et al., "Solid-phase peptide synthesis: from standard procedures to the synthesis of difficult sequences," Nat. Protoc., Dec. 2007, vol. 2, Issue 12, 3247-3256.

Colomb et al., "Radiation-Convertible Polymers from Norbornenyl Derivatives. Crosslinking with Ionizing Radiation," Journal of Applied Polymer Science, 1970, 14, 1659-1670.

Conner et al., "Regulated portals of entry into the cell," Nature, 2003, 422(6927):37-44.

Conrad et al., "ELPylated anti-human TNF therapeutic single-domain antibodies for prevention of lethal septic shock," Plant Biotechnology Journal, Jan. 2011, vol. 9, Issue 1, pp. 22-31.

Coskun et al., "Fibroblast Growth Factor 21 Corrects Obesity in Mice," Endocrinology, Dec. 2008, vol. 149, Issue 12, pp. 6018-6027.

Costa et al., "Active Targeting of Cancer Cells by Nanobody Decorated Polypeptide Micelle with Bio-orthogonally Conjugated Drug," Nano letters, Dec. 2018, 19(1):247-254.

Craik et al., "The future of peptide-based drugs," Chemical biology & drug design 81, Dec. 2013, vol. 81, Issue 1, pp. 136-147.

Cui et al., "Amino acid sequence in constitutionally isomeric tetrapeptide amphiphiles dictates architecture of one-dimensional nanostructures," J. Am. Chem. Soc., Aug. 2014, vol. 136, Issue 35, 12461-12468.

Cui et al., "Self-assembly of peptide amphiphiles: from molecules to nanostructures to biomaterials," Biopolymers, Jan. 2010, vol. 94, Issue 1, pp. 1-18.

Dai et al., "Versatile biomanufacturing through stimulus-responsive cell—material feedback," Nature chemical biology, Sep. 2019, 15(10):1017-1024.

Dalhaimer et al., "Single Molecule Visualization of Stable, Stiffness-Tunable, Flow-Conforming Worm Micelles," Macromolecules, 2003, 36(18):6873-6877.

Dalla Poza et al., "Targeting gemcitabine containing liposomes to CD44 expressing pancreatic adenocarcinoma cells causes an increase in the antitumoral activity," Biochim. Biophys. Acta, May 2013, vol. 1828, Issue 5, pp. 1396-1404.

Darzynkiewicz et al., "DNA content measurement for DNA ploidy and cell cycle analysis," Current Protocols in Cytometry, 2001, 7.5.1-7.5.24.

Das et al., "Conformations of intrinsically disordered proteins are influenced by linear sequence distributions of oppositely charged residues," Proc Natl Acad Sci U S A, National Academy of Sciences, Aug. 2013, 110(33):13392-13397.

Dasgupta et al., "Isopeptide Ligation Catalyzed by Quintessential Sortase A: Mechanistic Cues From Cyclic and Branched Oligomers of Indolicidin," The Journal of Biological Chemistry, May 2011, vol. 286, No. 27, pp. 23996-24006, Supplemental Information.

Day et al., "A new glucagon and GLP-1 co-agonist eliminates obesity in rodents," Nat Chem Biol, Oct. 2009, 5:749.

De et al., "Temperature-Regulated Activity of Responsive Polymer-Protein Conjugates Prepared by Grafting-from via RAFT Polymerization," J. Am. Chem. Soc. Jul. 2008, 130, 11288-11289.

De Simone et al., "Accurate random coil chemical shifts from an analysis of loop regions in native states of proteins," J Am Chem Soc, Nov. 2009, 131, 16332-16333.

Deer et al., "Phenotype and genotype of pancreatic cancer cell lines," Pancreas, May 2010, 39, 425-435.

Dejana et al., "The role of adherens junctions and VE-cadherin in the control of vascular permeability," J Cell Sci, Jul. 2008, 121, 2115-2122.

Delaglio et al., "NMRPipe: A multidimensional spectral processing system based on UNIX pipes," Journal of Biomolecular NMR 6, 1995, 277-293.

DeLisser et al., "Vascular endothelial platelet endothelial cell adhesion molecule 1(PECAM-1) regulates advanced metastatic progression," PNAS, Oct. 2010, 107, 18616-18621.

Dennis et al., "Albumin binding as a general strategy for improving the pharmacokinetics of proteins," J Biol Chem, 2002, 277(38): p. 35035-43.

Dennis et al., "Co-Translational Myristoylation Alters the Quaternary Structure of HIV-1 Nef in Solution," Proteins: Structure, Function, and Bioinformatics, 2005, 60:658-669.

Depp et al., "Native protein-initiated ATRP: A viable and potentially superior alternative to PEGylation for stabilizing biologics," Acta Biomater. Feb. 2009, 5, 560-569.

Deshayes et al., "Radium 223 dichloride for prostate cancer treatment," Drug Des Devel Ther, Sep. 2017, 11, 2643-2651.

DeYoung et al., "Encapsulation of exenatide in poly-(D,L-lactide-co-glycolide) microspheres produced an investigational long-acting once-weekly formulation for type 2 diabetes," Diabetes Technol Ther, Nov. 2011, 13, 1145-1154.

Diana et al., "Prognostic role and correlation of CA9, CD31, CD68 and CD20 with the desmoplastic stroma in pancreatic ductal adenocarcinoma," Oncotarget, Nov. 2016, 7, 72819-72832.

Diehl et al., "A Good Practice Guide to the Administration of Substances and Removal of Blood Including Routes and Volumes," J Appl Toxicol, 2001, 21, 15-23.

Dignon et al., "Relation between single-molecule properties and phase behavior of intrinsically disordered proteins," Proc Natl Acad Sci U S A, Oct. 2018, 115(40):9929-9934.

Dignon et al., "Sequence determinants of protein phase behavior from a coarse-grained model," PLoS Comput Biol, Jan. 2018, 14(1):e1005941.

Ding et al., "Mechanism for the alpha-helix to beta-hairpin transition," Proteins, 2003, 53, 220-228.

Ding et al., "βKlotho Is Required for Fibroblast Growth Factor 21 Effects on Growth and Metabolism," Cell Metab, Sep. 2012, 16(3):387-393.

(56) References Cited

OTHER PUBLICATIONS

Donnelly et al., "DNA Vaccines," Ann. Rev. Immunol., 1997, 15, 617-648.
Dreher et al., "Evaluation of an elastin-like polypeptide-doxorubicin conjugate for cancer therapy," J. of Controlled Release, 2003, 91:31-43.
Dreher et al., "Temperature triggered self-assembly of polypeptides into multivalent spherical micelles," J. Am. Chem. Soc. Jan. 2008, 130, 687-694.
Dreher et al., "Thermal cycling enhances the accumulation of a temperature-sensitive biopolymer in solid tumors," Cancer Res, May 2007, 67, 4418-4424.
Dreher, M. R. Ph.D. Thesis, Duke University, Durham, NC, Apr. 2006.
Dreis et al., "Preparation, Characterisation and Maintenance of Drug Efficacy of Doxorubicin—Loaded Human Serum Albumin (HSA) Nanoparticles," Int. J. Pharm., Aug. 2007, 341, 207-214.
Drucker "Mechanisms of Action and Therapeutic Application of Glucagon-like Peptide-1," Cell Metab, Apr. 2018, 27(4):740-756.
Drucker et al., "The incretin system: glucagon-like peptide-1 receptor agonists and dipeptidyl peptidase-4 inhibitors in type 2 diabetes," Lancet 368, Nov. 2006, 1696-1705.
Drucker, "Glucagon-like peptides," Diabetes 47, 1998, 159-169.
Drucker, "Incretin action in the pancreas: potential promise, possible perils, and pathological pitfalls," Diabetes, Oct. 2013, 62, 3316-3323.
Du et al., "Endoscope-assisted brachytherapy for pancreatic cancer: From tumor killing to pain relief and drainage," Journal of interventional gastroenterology, Jan. 2011, 1, 23-27.
Du et al., "Tailor-made dual pH-sensitive polymer-doxorubicin nanoparticles for efficient anticancer drug delivery," J. Am. Chem. Soc., Oct. 2011, 133, 17560-17563.
Duan et al., "Fibronectin type III domain based monobody with high activity," Biochemistry, Oct. 2007 46(44):12656-12664.
Duan et al., "Improving the thermostability and catalytic efficiency of Bacillus deramificans pullulanase by site-directed mutagenesis," Appl Environ Microbiol, American Society for Microbiology, Jul. 2013, 79(13):4072-4077.
Dubey et al., "Development and evaluation of folate functionalized albumin nanoparticles for targeted delivery of gemcitabine," Int J Pharm., Aug. 2015, 492(1-2):80-91.
Ducreux et al., "Radiation plus docetaxel and cisplatin in locally advanced pancreatic carcinoma: A non-comparative randomized phase II trial," Digestive and Liver Disease, Oct. 2014, 46, 950-955.
Duke University, "Gemcitabine/Nab-Paclitaxel With HIGRT in Resectable Pancreatic Cancer," Clinical Trial NCT02318095 <https://clinicaltrials.gov/ct2/show/NCT02318095> Webpage accessed Jan. 11, 2017.
Duncan, "The dawning era of polymer therapeutics," Nature Reviews Drug Discovery, 2003, 2, 347-360.
Duncan, R. "Polymer conjugates as anticancer nanomedicines," Nat. Rev. Cancer, Sep. 2006, 6, 688-701.
Duronio et al., "Protein N-myristoylation in Escherichia coli: Reconstitution of a eukaryotic protein modification in bacteria," Proc. Natl. Acad. Sci. USA, 1990, vol. 87, pp. 1506-1510.
Dyrberg et al., "Peptide as Atigens," J. Exp. Med., 1986, 164:1344-1349.
Dzuricky et al., "Avidity and Cell Uptake of Integrin Targeting Polypeptide Micelles is Strongly Shape Dependent," Nano letters, Sep. 2019, 19(9):6124-6132.
Dzuricky et al., "The Convergence of Artificial Protein Polymers and Intrinsically Disordered Proteins," Biochemistry, May 2018, 57(17):2405-2414.
Egan et al., "The Insulinotropic Effect of Acute Exendin-4 Administered to Humans: Comparison of Nondiabetic State to Type 2 Diabetes," The Journal of Clinical Endocrinology & Metabolism, 2002, 87, 1282-1290.
Ehlerding et al., "Biodegradable and Renal Clearable Inorganic Nanoparticles," Adv Sci (Weinh), Feb. 2016, 3(2):1500223.
Eisenhaber et al., "Prediction of lipid posttranslational modifications and localization signals from protein sequences: Big-II, NMT and PTS1," Nucleic Acids Res., 2003, 31, 3631-3634.
Eisenhauer et al., "New response evaluation criteria in solid tumours: Revised RECIST guideline (version 1.1)," Eur J Cancer, Jan. 2009, 45(2):228-247.
El-Assaad et al., "Saturated Fatty Acids Synergize with Elevated Glucose to Cause Pancreatic β-Cell Death," Endocrinology, 2003, 144(9):4154-4163.
Elbaum-Garfinkle et al., "The disordered P granule protein LAF-1 drives phase separation into droplets with tunable viscosity and dynamics," Proc Natl Acad Sci U S A, Jun. 2015, 112(23):7189-7194.
Ellis, "Macromolecular crowding: obvious but underappreciated," Trends Biochem. Sci., 2001, 26 (10), 597-604.
Elsabahy et al., "Design of polymeric nanoparticles for biomedical delivery applications," Chem Soc Rev, Royal Society of Chemistry, Apr. 2012, 41(7):2545-61.
Elvin et al., "Synthesis and properties of crosslinked recombinant pro-resilin," Nature, 2005, 437(7061):999-1002.
Elzoghby et al., "Implications of Protein- and Peptide-Based Nanoparticles as Potential Vehicles for Anticancer Drugs," Advances in Protein Chemistry and Structural Biology, Academic Press, Elsevier, Mar. 2015, Chapter Six, vol. 98, pp. 169-221.
Engin et al., "Thermoradiotherapy in the management of superficial malignant tumors," Clinical Cancer Research, 1995, 1, 139-145.
Erickson-Miller et al., "Differential toxicity of camptothecin, topotecan and 9-aminocamptothecin to human, canine, and murine myeloid progenitors (CFU-GM) in vitro," Cancer Chemother. Pharmacol., 1997, 39 (5), 467-472.
Etrych et al., "HPMA Copolymer Conjugates of Paclitaxe; and Docetaxel with pH-Controlled Drug Release," Molecular Pharmaceutics, Jun. 2010, 7(4):1015-1026.
Falk et al., "Hyperthermia in oncology," Int J Hyperthermia, 2001, 17, 1-18.
Farazi et al., "Structures of *Saccharomyces* cerevisiae N-myristoyltransferase with bound myristoylCoA and peptide provide insights about substrate recognition and catalysis," Biochemistry, 2001, 40, 6335-6343.
Farmer et al., "Conformational behavior of chemically reactive alanine-rich repetitive protein polymers," Biomacromolecules, 2005, 6, 1531-1539.
Farokhzad et al., "Targeted nanoparticle-aptamer bioconjugates for cancer chemotherapy in vivo," Proc Natl Acad Sci U S A, The National Academy of Sciences of the USA, Apr. 2006, 103(16):6315-20.
Feng et al., "Protein resistant surfaces: comparison of acrylate graft polymers bearing oligo-ethylene oxide and phosphorylcholine side chains," Biointerphases, Mar. 2006, 1 (1), 50.
Fernandez-Colino et al., "Amphiphilic Elastin-Like Block Co-Recombinamers Containing Leucine Zippers: Cooperative Interplay between Both Domains Results in Injectable and Stable Hydrogels," Biomacromolecules, Sep. 2015, 16, 3389-3398.
Finan et al., "A rationally designed monomeric peptide triagonist corrects obesity and diabetes in rodents," Nat Med, Jan. 2015, 21:27-36.
Finan et al., "Unimolecular Dual Incretins Maximize Metabolic Benefits in Rodents, Monkeys, and Humans," Sci Transl Med, Oct. 2013, 5(209):209ra151.
Fluegel et al., "Chain stiffness of elastin-like polypeptides," Biomacromolecules, Oct. 2010, 11, 3216-3218.
Fosgerau et al., "Peptide therapeutics: current status and future directions," Drug Discovery Today, Jan. 2015, 20, 122-128.
Franzmann et al., "Phase separation of a yeast prion protein promotes cellular fitness," Science, Jan. 2018, 359(6371):eaao5654.
Free et al., "A Phase 1, multi-center, randomized, double-blind, placebo controlled study to evaluate the safety/tolerability, pharmacokinetic and hemodynamic response following single ascending subcutaneous doses of PB1046 (Vasomera) in subjects with essential hypertension," Circulation, Mar. 2018, 130:A19112.
Friedman et al., "Directed Evolution to Low Nanomolar Affinity of a Tumor-Targeting Epidermal Growth Factor Receptor-Binding Affibody Molecule," J. Mol. Biol., Mar. 2008, 376, 1388-1402.

(56) References Cited

OTHER PUBLICATIONS

Frilling et al., "Recommendations for management of patients with neuroendocrine liver metastases," The lancet oncology, Jan. 2014, 15, e8-21.

Fu et al., "Nanoparticle Albumin—Bond (NAB) Technology is a Promising Method for Anti-Cancer Drug Delivery," Recent Patents on Anti-Cancer Drug Discovery, Nov. 2009. 4(3):262-272.

Fujiwara et al., "Modulating effect of the PI3-kinase inhibitor LY294002 on cisplatin in human pancreatic cancer cells," Journal of Experimental & Clinical Cancer Research, Nov. 2008, 27, 76.

Furgeson et al., "Structural optimization of a "smart" doxorubicin-polypeptide conjugate for thermally targeted delivery to solid tumors," Journal of Controlled Release, Jan. 2006, 110:362-369.

Furumoto et al., "Effect of coupling of albumin onto surface of PEG liposome on its in vivo disposition," International Journal of Pharmaceutics, Mar. 2007, 329(1-2): p. 110-116.

Gaberc-Porekar et al., "Obstacles and pitfalls in the PEGylation of therapeutic proteins," Curr. Opin. Drug Discov. Devel. Mar. 11, 2008, 242-250.

Gabizon et al., "Prolonged circulation time and enhanced accumulation in malignant exudates of doxorubicin encapsulated in poly-ethylene-glycol coated liposomes," Cancer Res., Feb. 1994, 54, 987-992.

Gaich et al., "The Effects of LY2405319, an FGF21 Analog, in Obese Human Subjects with Type 2 Diabetes," Cell Metab, Sep. 2013, 18(3):333-340.

Ganson et al., "Control of hyperuricemia in subjects with refractory gout, and induction of antibody against poly(ethylene glycol) (PEG), in a phase I trial of subcutaneous PEGylated urate oxidase," Arthritis Res. Ther. Feb. 8, 2006, R12-R22.

Ganson et al., "Pre-existing anti-polyethylene glycol antibody linked to first-exposure allergic reactions to pegnivacogin, a PEGylated RNA aptamer," J Allergy Clin Immunol, May 2016, 137(5): 1610-1613, e1617.

Gao et al., "In situ growth of a PEG-like polymer from the C terminus of an intein fusion protein improves pharmacokinetics and tumor accumulation" PNAS Early Edition, Jul. 2010, vol. 107, 1-6.

Gao et al., "In situ growth of a PEG-like polymer from the C terminus of an intein fusion protein improves pharmacokinetics and tumor accumulation," Proc. Natl. Acad. Sci., Sep. 2010, 107(38):16432-16437.

Gao et al., "In situ growth of a stoichiometric PEG-like conjugate at a protein's N-terminus with significantly improved pharmacokinetics," Proc. Natl. Acad. Sci., Sep. 2009, 15231-15236.

Gao, "Site-specific and in situ growth of stealth polymer conjugates of proteins with significally improved pharmacology," Journal of Controlled Release, Nov. 2013, 172(1):e116-e117.

Garanger et al., "Structural Evolution of a Stimulus-Responsive Diblock Polypeptide Micelle by Temperature Tunable Compaction of its Core," Macromolecules, Sep. 2015, 48, 6617-6627.

Garay et al., "Antibodies against polyethylene glycol in healthy subjects and in patients treated with PEG-conjugated agents," Expert Opinion. Drug Deliv. 9, Nov. 2012, 1319-1323.

Garcia Quiroz et al., "Syntax of Phase Transition Peptide Polymers with LCST and UCST Behavior," Jan. 1, 2013, Retrieved from the Internet: URL:https://dukespace.lib.duke.edu/dspace/bitstream/handle/10161/7256/GarciaQuirozduke0066D 11972.pdf?sequence=1 &isAllowed=y.

Gauthier et al., "Peptide/protein—polymer conjugates: synthetic strategies and design concepts," Chem. Commun., Jul. 2008, 2591-2611.

Ge et al., "Self-Cleavable Stimulus Responsive Tags for Protein Purification without Chromatography" J. Am. Chem. Soc., 2005, 127: 11228-11229.

Genbank Accession NM_001182082.1 (Mar. 2017).

Geng et al., Shape effects of filaments versus spherical particles in flow and drug delivery, Nat Nanotechnol, Nature Research, Apr. 2007, 2(4):249-55.

Ghoorchian et al., "Molecular architecture influences the thermally induced aggregation behavior of elastin-like polypeptides," Biomacromolecules, Oct. 2011, 12, 4022-4029.

Gianni et al., "Nonlinear pharmacokinetics and metabolism of paclitaxel and its pharmacokinetic/pharmacodynamic relationships in humans," J. Clin. Oncol., 1995, 13 (1), 180-190.

Giberti et al., "Radical retropubic prostatectomy versus brachytherapy for low-risk prostatic cancer: a prospective study," World J Urol, Oct. 2009, 27, 607-612.

Gibson et al., "Enzymatic assembly of DNA molecules up to several hundred kilobases," Nat Methods, May 2009, 6, 343-345.

Gilbreth et al., "Structural insights for engineering binding proteins based on non-antibody scaffolds," Curr Opin Struct Biol, Elsevier, Jun. 2012, 22(4):413-20.

Gillies et al., "Dendrimers and dendritic polymers in drug delivery," Drug Discovery Today, 2005, 10(1):35-43.

Gilroy et al., "Fusion of fibroblast growth factor 21 to a thermally responsive biopolymer forms an injectable depot with sustained anti-diabetic action," J Control Release, May 2018, 277:154-164.

Glassman et al., "Toughening of Thermoresponsive Arrested Networks of Elastin-Like Polypeptides to Engineer Cytocompatible Tissue Scaffolds," Biomacromolecules, Feb. 2016, 17, 415-426.

Gluck et al., "Single Vector System for Efficient N-myristoylation of Recombinant Proteins in *E. coli*," Plos One, Apr. 2010, 5(4) e100881.

Göke et al., "Exendin-4 is a high potency agonis and truncated exendin-(9-39)-amide an antagonist at the glucagon-like peptide 1-(7-36)-amide receptor of insulin-secreting b-cells," J. Biol. Chem. 268, 1993, 19650-19655.

Goldsmith et al., "Enzyme engineering: reaching the maximal catalytic efficiency peak," Curr Opin Struct Biol, Dec. 2017, 47:140-150.

Gordon et al., "Protein N-myristoylation," J. Biol. Chem., 1991, 266, 8647-8650.

Gosline et al., "Elastic proteins: biological roles and mechanical properties," Philos Trans R Soc Lond B Biol Sci, 2002, 357, 121-132.

Gottlieb et al., "NMR chemical shifts of common laboratory solvents as trace impurities," J. Org. Chem., 1997, 62, 7512-7515.

Goutelle et al., "The Hill equation: a review of its capabilities in pharmacological modelling. Fundam," Clin. Pharmacol. Dec. 22, 2008, 633-648.

Graff et al., "Theoretical analysis of antibody targeting of tumor spheroids: importance of dosage for penetration, and affinity for retention," Cancer Research, 2003, 63(6):1288-1296.

Gratton et al., "The effect of particle design on cellular internalization pathways," Proc Natl Acad Sci U S A, The National Academy of Sciences of the USA, Aug. 2008, 105(33):11613-8.

Greco et al., "The search for synergy: a critical review from a response surface perspective," Pharmacological Reviews, 1995, 24, 331-385.

Green et al., "Abraxane®, a novel Cremophor®-free, albumin-bound particle form of paclitaxel for the treatment of advanced non-small-cell lung cancer," Annals of Oncology, Aug. 2006, 17, 1263-1268.

Green et al., "Novel dipeptidyl peptidase IV resistant analogues of glucagon-like peptide-1(7-36) amide have preserved biological activities in vitro conferring improved glucose-lowering action in vivo" J. of Mol. Endocrin., 2003, 31(3): 529-540.

Greenfield, "Using circular dichroism spectra to estimate protein secondary structure," Nat. Protoc., Dec. 2006, 1(6):2876-90.

Grimm et al., "Advances in Brachytherapy," Reviews in Urology, 2004, 6, S37-S48.

Grover et al., "Protein-Polymer Conjugates: Synthetic Approaches by Controlled Radical Polymerizations & Interesting Applications", Curr Opin Chem Bioi., Dec. 2010; 14(6): 818-827.

Gu et al., "Enzymatic Synthesis of Nucleobase-Modified Single-Stranded DNA Offers Turnable Resistance to Nuclease Degradation," Biomacromolecules, Jul. 2018, 19, 3525-3535.

Gu et al., "Photocontrolled micellar aggregation of amphiphilic DNA-azobenzene conjugates," Colloids Surfaces B: Biointerfaces, Nov. 2015, 135, 126-132.

(56) References Cited

OTHER PUBLICATIONS

Gu et al., "Precise engineering of targeted nanoparticles by using self-assembled biointegrated block copolymers," Proc Natl Acad Sci U S A, The National Academy of Sciences of the USA, Feb. 2008, 105(7):2586-91.

Güngör et al., "Pancreatic cancer," British Journal of Pharmacology, Jan. 2014, 171, 849-858.

Guo et al., "Nanoparticles escaping RES and endosome: challenges for siRNA delivery for cancer therapy," J. Nanomaterials, Aug. 2011, 2011: 1-12.

Gustafsson, "Nonlinear structured-illumination microscopy: widefield fluorescence imaging with theoretically unlimited resolution," Proc Natl Acad Sci U S A, 2005, 102, 13081-13086.

Gustafsson, "Surpassing the lateral resolution limit by a factor of two using structured illumination microscopy," Short Communication. Journal of Microscopy, 2000, 198, 82-87.

Guzman et al., "Leiodermatolide, a novel marine natural product, has potent cytotoxic and antimitotic activity against cancer cells, appears to affect microtubule dynamics, and exhibits antitumor activity," Int. J. Cancer, Nov. 2016, 139, 2116-2126.

Ha et al., "Immunoglobulin Fc Heterodimer Platform Technology: From Design to Applications in Therapeutic Antibodies and Proteins," Front Immunol, Oct. 2016, 7(394) (in English).

Haider et al., "Genetically engineered polymers: Status and prospects for controlled release," J. Control. Release, 2004, 95, 1-26.

Halozyme Therapeutics, "PEGPH20 Plus Nab-Paclitaxel Plus Gemcitabine Compared With Nab-Paclitaxel Plus Gemcitabine in Subjects With Stage IV Untreated Pancreatic Cancer (HALO-109-202)," Clinical Trial NCT01839487 <https://clinicaltrials.gov/ct2/show/study/NCT01839487> Accessed May 29, 2018.

Hamada et al., "Novel therapeutic strategies targeting tumor-stromal interactions in pancreatic cancer," Frontiers in Physiology, Nov. 2013, vol. 4, Article 331, 7 pages.

Hamidi et al., "Pharmacokinetic Consequences of Pegylation," Drug Deliv., Dec. 2006, 13, 399-409.

Hamley, "Self-assembly of amphiphilic peptides," Soft Matter, Feb. 2011, 7, 4122.

Hampp et al., "Use of Antidiabetic Drugs in the U.S., 2003-2012," Diabetes Care, May 2014, 37:1367-1374.

Han et al., "Survival of patients with advanced pancreatic cancer after iodine$^{125}$ seeds implantation brachytherapy: A meta-analysis," Medicine, Feb. 2017, 96, e5719.

Harmon et al., "A Model for Hysteresis Observed in Phase Transitions of Thermally Responsive Intrinsically Disordered Protein Polymers," Biophysical Journal, Feb. 2017, 112(3):207a.

Harries et al., "Nanoparticle Albumin-Bound Paclitaxel for Metastatic Breast Cancer," J. Clin. Oncol., 2005, 23(31):7768-7771.

Harris et al., "Pegylation," Clinical Pharmacokinetics, 2001, 40(7):539-551.

Hart et al., "Attenuation of FGF signalling in mouse β-cells leads to diabetes," Nature, 2000, 408:864.

Hartgerink et al., "Self-assembly and mineralization of peptide-amphiphile nanofibers," Science, 2001, 294, 1684-8.

Hassouneh et al., "Elastin-like Polypeptide Diblock Copolymers Self-Assemble into Weak Micelles," Macromolecules, Jun. 2015, 48, 4183-4195.

Hassouneh et al., "Elastin-Like Polypeptides as a Purification Tag for Recombinant Proteins," Curr Protoc Protein Sci., Aug. 2010, Chapter 6. Unit 6.11. 10.1002/0471140864.ps0611s61.

Hassouneh et al., "Fusions of elastin-like polypeptides to pharmaceutical proteins," Methods Enzymol., Jan. 2012, 502, 215-37.

Hassouneh et al., "Unexpected Multivalent Display of Proteins by Temperature Triggered Self-assembly of Elastin-like Polypeptide Block Copolymers," Biomacromolecules, Apr. 2012, vol. 13, Issue 4, pp. 1598-1605.

Hathout et al., "Analysis of seed loss and pulmonary seed migration in patients treated with virtual needle guidance and robotic seed delivery," American journal of clinical oncology, Oct. 2011, 34, 449-453.

He et al., "Comparative genomics of elastin: Sequence analysis of a highly repetitive protein," Matrix Biology, Sep. 2007, 26:524-540.

He et al., "Improving protein resistance of α-Al2O3 membranes by modification with POEGMA brushes," Applied Surface Science, Nov. 2011, 258(3):1038-1044.

Heagerty et al., Biometrics, "Time-dependent ROC curves for censored survival data and a diagnostic marker," Jun. 2000, 56(2):337-44.

Heal et al., "N-Myristoyl transferase-mediated protein labelling in vivo," Org. Biomol. Chem., Aug. 2008, 6(13):2308-2315.

Heal et al., "Site-specific N-terminal labelling of proteins in vitro and in vivo using N-myristoyl transferase and bioorthogonal ligation chemistry," Chem. Commun., Jan. 2008, 3, 480-482.

Heredia et al., "In Situ Preparation of Protein—"Smart" Polymer Conjugates with Retention of Bioactivity," J. Am. Chem. Soc. Jan. 2006, 127, 16955-16960.

Herrero-Vanrell et al., "Self-assembled particles of an elastin-like polymer as vehicles for controlled drug release," J Control Release, 2005, 102, 113-122.

Hershfield et al., "Induced and pre-existing anti-polyethylene glycol antibody in a trial of every 3-week dosing of pegloticase for refractory gout, including in organ transplant recipients," Arthritis Res. Ther. 16, Mar. 2014, R63.

Hidalgo, "Pancreatic Cancer," N Engl J Med, Apr. 2010, 362, 1605-1617.

Hingorani et al., "Phase Ib Study of PEGylated Recombinant Human Hyaluronidase and Gemcitabine in Patients with Advanced Pancreatic Cancer," Clinical Cancer Research, Jun. 2016, 22, 2848-2854.

Ho et al., "Chemoenzymatic Labeling of Proteins for Imaging in Bacterial Cells," J. Am. Chem. Soc., Nov. 2016, 138(46):15098-15101.

Ho et al., "Internal radiation therapy for patients with primary or metastatic hepatic cancer: a review," Cancer, 1998, 83, 1894-1907.

Hober et al., "Protein A chromatography for antibody purification," Journal of Chromatography B 848, Mar. 2007, pp. 40-47.

Hochkoeppler, "Expanding the landscape of recombinant protein production in *Escherichia coli*," Biotechnol. Lett., Dec. 2013, 35, 1971-1981.

Hofmann et al., "A kinetic study on the enzymatic hydrolysis of fluoresceindiacetate and fluorescein-di-β-D-galactopyranoside," Analytical biochemistry, 1983, 131(1):180-186.

Holehouse et al., "CIDER: Classification of Intrinsically Disordered Ensemble Regions," Biophysical Journal, Feb. 2015, vol. 108, Issue 2, Supplement 1, p. 228a.

Holehouse et al., "Functional Implications of Intracellular Phase Transitions," Biochemistry, May 2018, 57(17):2415-2423.

Holm et al., "Transperineal $^{125}$iodine seed implantation in prostatic cancer guided by transrectal ultrasonography," The Journal of urology, 2002, 167, 985-988.

Hopp et al., "The effects of affinity and valency of an albumin-binding domain (ABD) on the half-life of a single-chain diabody-ABD fusion protein," Protein Engineering Design and Selection, Sep. 2010, 23(11): p. 827-834.

Hortobágyi, "Anthracyclines in the Treatment of Cancer," Drugs, 1997, vol. 54, No. 4, pp. 1-7.

Howell et al., "The Mird Perspective 1999," J Nucl Med, 1999, 40, 3S-10S.

Hruby et al., "New bioerodable thermoresponsive polymers for possible radiotherapeutic applications," Journal of Controlled Release, May 2007, 119, 25-33.

Hruby et al., "Thermoresponsive polymeric radionuclide delivery system—an injectable brachytherapy," Eur J Pharm Sci., Feb. 2011, 42, 484-488.

Hrycushko et al., "Direct intratumoral infusion of liposome encapsulated rhenium radionuclides for cancer therapy: effects of non-uniform intratumoral dose distribution," Med Phys, Mar. 2011, 38, 1339-1347.

Hu et al., "Design of tumor-homing and pH-responsive polypeptide-doxorubicin nanoparticles with enhanced anticancer efficacy and reduced side effects," Chemical Communications, Jun. 2015, 51, 11405-11408.

(56) References Cited

OTHER PUBLICATIONS

Hu et al., "Nanografting De Novo Proteins onto Gold Surfaces," Langmuir, 2005, vol. 21:9103-9109.

Huang et al., "Photodynamic Therapy Synergizes with Irinotecan to Overcome Compensatory Mechanisms and Improve Treatment Outcomes in Pancreatic Cancer," Cancer Research, Mar. 2016, 76, 1066-1077.

Huber et al., "Designer amphiphilic proteins as building blocks for the intracellular formation of organelle-like compartments," Nat Mater, Jan. 2015, 14(1):125-132.

Huotari et al., "Endosome maturation," EMBO J, Aug. 2011, 30 (17), 3481-3500.

Hwang et al., "Caprolactonic poloxamer analog: PEG-PCL-PEG," Biomacromolecules, 2005, 6, 885-890.

Hwang et al., "Gene therapy for primary and metastatic pancreatic cancer with intraperitoneal retroviral vector bearing the wild-type p53 gene," Surgery, 1998, 124, 143-151.

Ibrahim et al., "Phase I and pharmacokinetic study of ABI-007, a Cremophor-free, protein-stabilized, nanoparticle formulation of paclitaxel," Clin. Cancer Res., 2002, 8 (5), 1038-1044.

Ilangovan et al., "Structure of sortase, the transpeptidase that anchors proteins to the cell wall of *Staphylococcus aureus*," Proc. Natl. Acad. Sci. 98, 2001, 6056-6061.

Inostroza-Brito et al., "Co-assembly, spatiotemporal control and morphogenesis of a hybrid protein—peptide system," Nat. Chem., Nov. 2015, 7, 1-8.

Ishida et al., "Accelerated blood clearance (ABC) phenomenon upon repeated injection of PEGylated liposomes," International Journal of Pharmaceutics, May 2008, 354(1-2):56-62.

Ito et al., "Impaired negative feedback suppression of bile acid synthesis in mice lacking βKlotho," J Clin Invest, 2005, 115(8):2202-2208.

Ito et al., "In vivo antitumor effect of the mTOR inhibitor CCI-779 and gemcitabine in xenograft models of human pancreatic cancer," International Journal of Cancer, May 2006, 118, 2337-2343.

Jacob et al., "Human phagocytes employ the myeloperoxidase-hydrogen peroxide system to synthesize dityrosine, trityrosine, pulcherosine, and isodityrosine by a tyrosyl radical-dependent pathway," J. Biol. Chem., 1996, 271, 19950-19956.

Jain, "Barriers to Drug-Delivery in Solid Tumors," Sci Am, 1994, 271, 58-65.

Jakubowski et al., "Activators regenerated by electron transfer for atom-transfer radical polymerization of (meth)acrylates and related block copolymers," Angew. Chem. Int. Ed., Jun. 2006, 4482-4486.

Janes et al., "Chitosan nanoparticles as delivery systems for doxorubicin," J. Control Release, 2001, 73, 255-267.

Jenkins et al., In vivo monitoring of tumor relapse and metastasis using bioluminescent PC-3M-luc-C6 cells in murine models of human prostate cancer. Clinical & Experimental Metastasis, 2003, 20, 745-756.

Ji et al., "RGD-conjugated albumin nanoparticles as a novel delivery vehicle in pancreatic cancer therapy," Cancer Biology & Therapy, Feb. 2012, 13, 206-215.

Jia et al., "Preparation, physicochemical characterization and cytotoxicity in vitro of gemcitabine-loaded PEG-PDLLA nanovesicles," World J. Gastroenterol., Feb. 2010, 16(8):1008-1013.

Jiang et al., "Nanoparticle-mediated cellular response is size-dependent," Nat Nanotechnol, Nature Research, Mar. 2008, 3(3):145-50.

Jiang et al., "The internal structure of self-assembled peptide amphiphiles nanofibers," Soft Matter, Feb. 2007, 3, 454.

Jin et al., "Protein-resistant polyurethane prepared by surface-initiated atom transfer radical graft polymerization (ATRgP) of water-soluble polymers: effects of main chain and side chain lengths of grafts," Colloids and surfaces. B, Biointerfaces, Apr. 2009, 70 (1), 53-9.

Johansson et al., "Structure, Specificity, and Mode of Interaction for Bacterial Albumin-binding Modules," J. Biol. Chem. 2002, 277 (10), 8114-8120.

Johansson et al., "The GA module, a mobile albumin-binding bacterial domain, adopts a three-helix-bundle structure," FEBS Lett, 1995, 374(2):257-261.

Johnson et al., "Fibroblast Growth Factor 21 Reduces the Severity of Cerulein-Induced Pancreatitis in Mice," Gastroenterology, Nov. 2009, 137(5):1795-1804.

Jokerst et al., "Nanoparticle PEGylation for imaging and therapy," Nanomedicine (Lond), Future Medicine, Jun. 2011, 6(4):715-28.

Jonsson et al., "Engineering of a femtomolar affinity binding protein to human serum albumin," Protein Engineering Design and Selection, Aug. 2008, 21(8): 515-527.

Junutula et al., "Site-specific conjugation of a cytotoxic drug to an antibody improves the therapeutic index," Nat Biotechnol, Aug. 2008, 26(8):925-932.

Jurney et al., "Unique size and shape-dependent uptake behaviors of non-spherical nanoparticles by endothelial cells due to a shearing flow," J Control Release, Jan. 2017, 245:170-176.

Kaighn et al., "Establishment and characterization of a human prostatic carcinoma cell line (PC- 3)," Investigative urology, 1979, 17, 16-23.

Kaitin et al., "Pharmaceutical innovation in the 21st century: new drug approvals in the first decade, 2000-2009," Clin Pharmacol Ther, Feb. 2011, 89, 183-188.

Kamaly et al., "Targeted polymeric therapeutic nanoparticles: design, development and clinical translation," Chem Soc Rev, Royal Society of Chemistry, Apr. 2012, 41(7):2971-3010.

Kamisawa et al., "Pancreatic cancer," Lancet, Jul. 2016, 388, 73-85.

Kanoski et al., "The role of nausea in food intake and body weight suppression by peripheral GLP-1 receptor agonists, exendin-4 and liraglutide," Neuropharmacology 62, Apr. 2012, 1916- 1927.

Kanyama et al., "Usefulness of Repeated Direct Intratumoral Gene Transfer Using Hemagglutinating Virus of Japan-Liposome Method for Cytosine Deaminase Suicide Gene Therapy," Cancer Research, 2001, 61, 14-18.

Karagoz et al., "Polymerization-Induced Self-Assembly (PISA)—control over the morphology of nanoparticles for drug delivery applications," Polym. Chem., Jan. 2014, 5(2):350-355.

Karamanolis et al., "Increased expression of VEGF and CD31 in postradiation rectal tissue: implications for radiation proctitis," Mediators Inflamm, May 2013, 515048.

Karperien, A. FracLac for Image J, version 2.5 <http://rsb.info.nih.gov/ij/plugins/fraclac/FLHelp/Introduction.htm> 1999-2012.

Kaspar et al., "Future directions for peptide therapeutics development," Drug Discovery Today, Sep. 2013, 18, 807-817.

Katakura, "Nuclear Data Sheets for A = 125," Nuclear Data Sheets, Mar. 2011, 112, 495-705.

Kataoka et al., "Block copolymer micelles for drug delivery: Design, characterization and biological significance," Advanced Drug Delivery Reviews, 2001, 47:113-131.

Kato et al., "Acidic extracellular microenvironment and cancer," Cancer Cell Int, Sep. 2013, 13, 89, 8 pages.

Katti et al., "Amino acid repeat patterns in protein sequences: Their diversity and structural-functional implications," Protein Science, 2000, 9: 1203-1209.

Keefe et al., "Poly(zwitterionic) protein conjugates offer increased stability without sacrificing binding affinity or bioactivity," Nat Chem, Jan. 2012, 4(1):59-63.

Keller et al., "Empirical Statistical Model to Estimate the Accuracy of Peptide Identifications Made by MS/MS and Database Search," Anal. Chem. 2002, 74, 5383-5392.

Kelly et al., "How to study proteins by circular dichroism," Biochim. Byophys. Acta—Proteins Proteomics, 2005, 1751(2):119-39.

Kelly et al., "Shape-specific, monodisperse nano-molding of protein particles," J Am Chem Soc, ACS Publications, Apr. 2008, 130(16):5438-9.

Kesharwani et al., "Dendrimer as nanocarrier for drug delivery," Progress in Polymer Science, Feb. 2014, 39(2):268-307.

Keten et al., "Nanoconfinement controls stiffness, strength and mechanical toughness of β-sheet crystals in silk," Nat Mater, Mar. 2010, 9, 359-367.

Khandare et al., "Polymer-drug conjugates: Progress in polymeric drugs," Prog. Polym. Sci., 2005, vol. 31, pp. 359-397.

(56) References Cited

OTHER PUBLICATIONS

Khanna et al., "The dog as a cancer model," Nat. Biotechnol., Sep. 2006, 24, 1065-1066.
Kharitonenkov et al., "FGF-21 as a novel metabolic regulator," J Clin Invest, 2005, 115(6):1627-1635.
Kharitonenkov et al., "FGF21 Revolutions: Recent Advances Illuminating FGF21 Biology and Medicinal Properties," Trends Endocrinol Metab, Nov. 2015, 26(11):608-617.
Kharitonenkov et al., "Fibroblast growth factor 21 night watch: advances and uncertainties in the field," J Intern Med, Nov. 2016, 281(3):233-246.
Kharitonenkov et al., "Inventing new medicines: The FGF21 story," Mol Metab, Jun. 2014, 3(3):221-229.
Khazov et al., "Nuclear Data Sheets for A = 131," Nuclear Data Sheets, 2006, 107, 2715-2930.
Khoo et al., "Activation of mitogen-activating protein kinase by glucose is not required for insulin secretion," Proc Natl Acad Sci USA, 1997, 94(11):5599-5604.
Khoo et al., "Regulation of Insulin Gene Transcription by ERK1 and ERK2 in Pancreatic β Cells," J Biol Chem, 2003, 278(35):32969-32977.
Kim et al., "Effects of Once-Weekly Dosing of a Long-Acting Release Formulation of Exenatide on Glucose Control and Body Weight in Subjects With Type 2 Diabetes," Diabetes Care, Jun. 2007, 30, 1487-93.
Kim et al., "Recombinant elastin-mimetic biomaterials: Emerging applications in medicine," Adv Drug Deliv Rev, Dec. 2010, 62, 1468-1478.
Kim et al., "Site-Specific PEGylated Exendin-4 Modified with a High Molecular Weight Trimeric PEG Reduces Steric Hindrance and Increases Type 2 Antidiabetic Therapeutic Effects," Bioconjugate Chem., Nov. 2012, 23, 2214-2220.
Kim et al., "Ultrasensitive Carbon nanotube-based biosensors using antibody-binding fragments," Analytical Biochemistry, Jul. 2008, 381, 193-198.
Knop et al., "Poly(ethylene glycol) in Drug Delivery: Pros and Cons as Well as Potential Alternatives," Angewandte Chemie International Edition, Aug. 2010, 49(36):6288-6308.
Knudsen, "Glucagon-like Peptide-1: The Basis of a New Class of Treatment for Type 2 Diabetes" J. Med. Chem, 2004, 47: 4128-4134.
Kobashigawa et al., "Attachment of an NMR-Invisible Solubility Enhancement Tag Using A Sortase-Mediated Protein Ligation Method," J Biomol NMR. Mar. 2009, vol. 43, No. 3; pp. 145-150.
Kobayashi et al., "Summary of recombinant human serum albumin development," Biologicals, Mar. 2006, 34(1): 55-59.
Koehler et al., "Albumin affinity tags increase peptide half-life in vivo," Bioorganic & Medicinal Chemistry Letters, 2002, 12(20): 2883-2886.
Kontos et al., "Drug development: longer-lived proteins," Chemical Society Reviews, Feb. 2012, 41(7):2686-2695.
Koong et al., "Phase II study to assess the efficacy of conventionally fractionated radiotherapy followed by a stereotactic radiosurgery boost in patients with locally advanced pancreatic cancer," Int J Radiation Oncol Biol Phys, 2005, 63, 320-323.
Kothare et al., "Pharmacokinetics, pharmacodynamics, tolerability, and safety of exenatide in Japanese patients with type 2 diabetes mellitus," J. Clin. Pharmacol. 48, Jan. 2009, 1389-1399.
Kowalczyk et al., "Elastin-like Polypeptides as a Promising Family of Genetically-Engineered Protein Based Polymers," World Journal of Microbiology and Biotechnology, Springer, Apr. 2014, 30(8):2141-2152.
Kramer et al., "Quantitative Side-Chain Modifications of Methionine-Containing Elastin-Like Polypeptides as a Versatile Tool to Tune Their Properties," ACS Macro Lett., Nov. 2015, 4(11):1283-1286.
Kraulis et al., "The serum albumin-binding domain of *streptococcal* protein G is a three-helical bundle: a heteronuclear NMR study," FEBS letters, 1996, 378(2): p. 190-194.
Krause et al., "Structure and function of claudins," Biochmica et Biophysica Acta, Mar. 2008, 1778, 631-645.
Krempien et al., "Neoadjuvant chemoradiation in patients with pancreatic adenocarcinoma," HPB (Oxford), Feb. 2006, 8(1):22-28.
Kruger et al., "Analysis of the Substrate Specificity of the *Staphylococcus aureus* Sortase Transpeptidase SrtA†," Biochemistry, 2004, 43, 1541-1551.
Kulkarni et al., "Bioorthogonal Chemoenzymatic Functionalization of Calmodulin for Bioconjugation Applications," Bioconjug. Chem., Oct. 2015, 26(10):2153-2160.
Kulkarni et al., "Design of lipid nanoparticles for in vitro and in vivo delivery of plasmid DNA," Nanomedicine, May 2017, 13(4):1377-1387.
Kulkarni et al., "Selective functionalization of the protein N terminus with N-myristoyl transferase for bioconjugation in cell lysate," ChemBioChem, Oct. 2013, 14, 1958-1962.
Kumar et al., "N-Terminal Region of the Catalytic Domain of Human N-Myristoyltransferase 1 Acts as an Inhibitory Module," PLoS One, May 2015, 10(5):e0127661.
Kupelian et al., "Radical prostatectomy, external beam radiotherapy <72 Gy, external beam radiotherapy > or =72 Gy, permanent seed implantation, or combined seeds/external beam radiotherapy for stage T1-T2 prostate cancer," International journal of radiation oncology, biology, physics, 2004, 58, 25-33.
Kurosu et al., "Tissue-specific Expression of βKlotho and Fibroblast Growth Factor (FGF) Receptor Isoforms Determines Metabolic Activity of FGF19 and FGF21," J Biol Chem, Sep. 2007, 282(37):26687-26695.
Kyte et al., "A Simple Method for Displaying the Hydropathic Character of a Protein," J. Mol. Biol., 1982, 157:105-132.
Labelle et al., "Vascular endothelial cadherin promotes breast cancer progression via transforming growth factor β signaling," Cancer Res, Mar. 2008, 68, 1388-1397.
Lacroix et al., "Elucidating the folding problem of alpha-helices: local motifs, long-range electrostatics, ionic-strength dependence and prediction of NMR parameters," J Mol Biol, 1998, 284, 173-191.
Langer et al., "Designing materials for biology and medicine," Nature, 2004, 428, 487-92.
Laybutt et al., "Endoplasmic reticulum stress contributes to beta cell apoptosis in type 2 diabetes," Diabetologia, Apr. 2007, 50(4):752-763.
Le Droumaguet et al., "Recent advances in the design of bioconjugates from controlled/living radical polymerization," Polym. Chem. Jan. 2010, 1, 563-598.
Le Meins et al., "Hybrid polymer/lipid vesicles: State of the art and future perspectives," Mater. Today, Oct. 2013, 16, 397-402.
Leader et al., "Protein therapeutics: a summary and pharmacological classification," Nat. Rev. Drug Discov. Jan. 7, 2008, 21-39.
Lee et al., "Atomistic molecular dynamics simulations of peptide amphiphile self-assembly into cylindrical nanofibers," J. Am. Chem. Soc., Feb. 2011, 133, 3677-3683.
Lee et al., "Immunohistochemical analysis of claudin expression in pancreatic cystic tumors," Oncology Reports, Apr. 2011, 25(4):971-978.
Lee et al., "In vivo bioluminescent imaging of irradiated orthotopic pancreatic cancer xenografts in nonobese diabetic-severe combined immunodeficient mice: a novel method for targeting and assaying efficacy of ionizing radiation," Transl. Oncol., Jun. 2010, 3, 153-159.
Lee et al., "Mechanical properties of cross-linked syntheti elastomeric polypentapeptides," Macromolecules, 2001, 34, 5968-5974.
Lee et al., "Nanoparticle-Delivered Chemotherapy: Old Drugs in New Packages." Oncology (Williston Park, NY) 31.3 (Mar. 2017): 198-208.
Lee et al., "Phase transition and elasticity of protein-based hydrogels," J. Biomater. Sci. Polymer Edn, 2001, 12, 229-242.
Lee et al., "Polymersomes for drug delivery: design, formation and characterization," J Control Release, Elsevier, Jul. 2012, 161(2):473-83.
Lee et al., "Structures of β-klotho reveal a 'zip code'-like mechanism for endocrine FGF signaling," Nature, Jan. 2018, 553:501-505.

(56) References Cited

OTHER PUBLICATIONS

Lee et al., "Theranostic nanoparticles with controlled release of gemcitabine for targeted therapy and MRI of pancreatic cancer," ACS Nano, Mar. 2013, 7(3):2078-2089.

Leibowitz et al., "Glucose-Regulated Proinsulin Gene Expression Is Required for Adequate Insulin Production during Chronic Glucose Exposure," Endocrinology, 2002, 143(9):3214-3220.

Lele et al., "Synthesis of uniform protein-polymer conjugates," Biomacromolecules 6, 2005, 3380-3387.

Lennen et al., "Membrane Stresses Induced by Overproduction of Free Fatty Acids in *Escherichia coli*," Appl Environ Microb., Nov. 2011, 77(22):8114-28.

Leung et al., "Bio-Click Chemistry: Enzymatic Functionalization of PEGylated Capsules for Targeting Applications **," Angew. Chem. Int. Ed. Jul. 2012, 51, 7132-7136.

LeVine et al., "Thioflavine T interaction with synthetic Alzheimer's disease beta-amyloid peptides: detection of amyloid aggregation in solution," Protein Sci., 1993, 2, 404-10.

Levy et al., "Novel Exenatide Analogs with Peptidic Albumin Binding Domains: Potent Anti-Diabetic Agents with Extended Duration of Action," PLoS ONE, Feb. 2014, 9(2): e87704, 9 pages.

Lewis et al., "Use of digitized video microscopy with a fluorogenic enzyme substrate to demonstrate cell-and compartment-specific gene expression in *Salmonella enteritidis* and Bacillus subtilis," Molecular microbiology, 1994, 13:655-662.

Li et al., "Elastin is an essential determinant of arterial morphogenesis," Nature, 1998, 393, 276-280.

Li et al., "FGF21 Is Not a Major Mediator for Bone Homeostasis or Metabolic Actions of PPARα and PPARγ Agonists," J Bone Miner Res, Apr. 2017, 32(4):834-845.

Li et al., "Molecular description of the LCST behavior of an elastin-like polypeptide," Biomacromolecules, Aug. 2014, 15, 3522-3530.

Li et al., "Nanoparticles Evading the Reticuloendothelial System: Role of The Supported Bilayer," Biochim. Biophys. Acta, Oct. 2009, 1788 (10), 2259-2266.

Li et al., "Pancreatic cancer," Lancet, 2004, 363, 1049-1057.

Li et al., "Phase transitions in the assembly of multivalent signalling proteins," Nature, Nature Research, Mar. 2012, 483(7389):336-340.

Li et al., "Prediction of solvent-induced morphological changes of polyelectrolyte diblock copolymer micelles," Soft Matter, Nov. 2015, 11(42): 8236-45.

Li et al., "Protein adsorption on oligo(ethylene glycol)-terminated alkanethiolate self-assembled monolayers: The molecular basis for nonfouling behavior," The journal of physical chemistry. B, 2005, 109 (7), 2934-41.

Li et al., "Temperature-Triggered Phase Separation of a Hydrophilic Resilin-Like Polypeptide," Macramol. Rapid Commun., Jan. 2015, 36(1):90-95.

Li et al., "Tunable Assembly of Protein-Microdomains in Living Vertebrate Embryos," Advanced Biosystems, Oct. 2018, 2(10):1800112.

Liao et al., "Removal of N-terminal methionine from recombinant proteins by engineered *E. coli* methionine aminopeptidase," Prot. Sci. 13, 2004, 1802-1810.

Liechty et al., "Polymers for Drug Delivery Systems," Annual review of chemical and biomolecular engineering, Aug. 2010, 1:149-173.

Lillie et al., "The viscoelastic basis for the tensile strength of elastin," Int J Biol Macromol, 2002, 30, 119-127.

Lim et al., "Improved Non-Chromatographic Purification of a Recombinant Protein by Cationic Elastin-like Polypeptides" Biomacromolecules, May 2007, 8(5): 1417-1424.

Lim et al., "In situ cross-linking of elastin-like polypeptide block copolymers for tissue repair," Biomacromolecules, Feb. 2008, 9, 222-230.

Lim et al., "In vivo post-translational modifications of recombinant mussel adhesive protein in insect cells," Biotechnol. Prog., Sep.-Oct. 2011, 27(5):1390-1396.

Lin et al., "Adiponectin Mediates the Metabolic Effects of FGF21 on Glucose Homeostasis and Insulin Sensitivity in Mice," Cell Metab, May 2013, 17(5):779-789.

Lin et al., "Formation and Maturation of Phase-Separated Liquid Droplets by RNA-Binding Proteins," Mol Cell, Oct. 2015, 60(2):208-219.

Lin et al., "Functional expression of a biologically active fragment of soluble gp130 as an ELP-fusion protein in transgenic plants: purification via inverse transition cycling," Biochem J, Sep. 2006, 398(3):577-583.

Lin et al., "Intrinsically disordered sequences enable modulation of protein phase separation through distributed tyrosine motifs," J Biol Chem, Nov. 2017, 292(46):19110-19120.

Lin et al., "Phase Separation and Single-Chain Compactness of Charged Disordered Proteins are Strongly Correlated," Biophys J, May 2017, 112(10):2043-2046.

Lin et al., "Sequence-Specific Polyampholyte Phase Separation in Membraneless Organelles," Phys Rev Lett, Oct. 2016, 117(17):178101.

Lin et al., "Statistical properties of the traditional algorithm-based designs for phase I cancer clinical trials," Biostatistics, 2001, 2(2):203-215.

Lin et al., "Utility of immunohistochemistry in the pancreatobiliary tract," Arch Pathol Lab Med, Jan. 2015, 139, 24-38.

Linder et al., "Lipid Modifications of G Protein Subunits," J. Biol. Chem., 1991, 266(7):4654-4659.

Ling et al., "Protein thioester synthesis enabled by sortase," J. Am Chem Soc, Jul. 2012, 134(26):10749-10752.

Liong et al., "Multifunctional inorganic nanoparticles for imaging, targeting, and drug delivery," ACS Nano, ACS Publications, May 2008, 2(5):889-96.

Litiere et al., "Recist—learning from the past to build the future," Nat Rev Clin Oncol, Mar. 2017, 14, 187-192.

Liu et al., "Brachytherapy using injectable seeds that are self-assembled from genetically encoded polypeptides in situ," Cancer Res, Nov. 2012, 72, 5956-5965.

Liu et al., "Hydrophobic modifications of cationic polymers for gene delivery," Prog. In Polym. Sci., Sep. 2010, 35, 1144-1162.

Liu et al., "In Situ Formation of Protein-Polymer Conjugates through Reversible Addition Fragmentation Chain Transfer Polymerization**," Angew. Chem. Int. Ed. Apr. 2007, 46, 3099-3103.

Liu et al., "Injectable intratumoral depot of thermally responsive polypeptide-radionuclide conjugates delays tumor progression in a mouse model," J. Control Release, May 2010, 144(1):2-9.

Liu et al., "Integrin $\alpha_v \beta_3$-Targeted Cancer Therapy," Drug Dev Res, Wiley, Sep. 2008, 69(6):329-339.

Liu et al., "Tracking the in vivo fate of recombinant polypeptides by isotopic labeling," Journal of Controlled Release, Sep. 2006, 114, 184-192.

Liu et al., "Tumor accumulation, degradation and pharmacokinetics of elastin-like polypeptides in nude mice," Journal of Controlled Release, Nov. 2006, 116, 170-178.

Livingstone, "Theoretical property predictions. Curr Top Med Chem Field Full Journal Title: Current topics in medicinal chemistry," Curr. Top. Med. Chem. 2003, 3, 1171-1192.

Loh et al., "Utilising inorganic nanocarriers for gene delivery," Biomater Sci, Jan. 2016, 4(1):70-86.

LoPresti et al., "Polymersomes: nature inspired nanometer sized compartments," Journal of Materials Chemistry, RSC Publishing, Jun. 2009, 19(22):3576-3590.

Lovshin et al., "Incretin-based therapies for type 2 diabetes mellitus," Nat. Rev. Endocrinol. Jun. 5, 2009, 262-269.

Ludden, "Nonlinear pharmacokinetics: clinical Implications," Clin. Pharmacokinet., 1991, 20 (6), 429-446.

Luginbuhl et al., "One-week glucose control via zero-order release kinetics from an injectable depot of glucagon-like peptide-1 fused to a thermosensitive biopolymer," Nat. Biomed. Eng. Jun. 1, 2017, Article No. 0078.

Luginbuhl et al., "Recombinant Synthesis of Hybrid Lipid-Peptide Polymer Fusions that Self-Assemble and Encapsulate Hydrophobic Drugs," Angew Chem Int Ed Engl., Nov. 2017, 56(45):13979-13984.

(56) References Cited

OTHER PUBLICATIONS

Lukyanov et al., "Micelles From Lipid Derivatives of Water-Soluble Polymers as Delivery Systems for Poorly Soluble Drugs," Adv. Drug Deliver. Rev., 2004, 56(9):1273-1289.
Lukyanov et al., "Tumor-targeted liposomes: doxorubicin-loaded long-circulating liposomes modified with anti-cancer antibody," J Control Release, 2004, 100(1):135-44.
Lund et al., "Phase II study of gemcitabine (2',2'-difluorodeoxycytidine) in previously treated ovarian cancer patients," J. Natl. Cancer. Inst. 1994, 86(20):1530-1533.
Luo et al., "Noncovalent Modulation of the Inverse Temperature Transition and Self-Assembly of Elastin-b-Collagen-like Peptide Bioconjugates," J Am Chem Soc, Dec. 2015, 137, 15362-15365.
Lutz et al., "About the Phase Transitions in Aqueous Solutions of Thermoresponsive Copolymers and Hydrogels Based on 2-(2-methoxyethoxy)ethyl Methacrylate and Oligo(ethylene glycol) Methacrylate," Macromolecules, Mar. 2007, 40, 2503-2508.
Lutz et al., "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," Macromolecules, Jan. 2006, 39, 893-896.
Lyons et al., "Comparisons of Recombinant Resilin-like Proteins: Repetitive Domains are Sufficient to Confer Resilin-like Properties," Biomacromolecules, ACS Publications, Oct. 2009, 10(11):3009-3014.
Lyons et al., "Design and facile production of recombinant resilin-like polypeptides: Gene construction and a rapid protein purification method," Protein Engineering Design & Selection, Oxford university Press, Jan. 2007, 20(1):25-32.
Ma et al., "Non-fouling" oligo(ethylene glycol)-functionalized polymer brushes synthesized by surface-initiated atom transfer radical polymerization, Advanced Materials 2004, 16 (4), 338.
Ma et al., "Protein-resistant polymer coatings on silicon oxide by surface-initiated atom transfer radical polymerization," Langmuir: the ACS journal of surfaces and colloids, Mar. 2006, 22 (8), 3751-6.
Ma et al., "Surface-Initiated Atom Transfer Radical Polymerization of Oligo(ethylene glycol) Methyl Methacrylate from a Mixed Self-Assembled Monolayer on Gold," Advanced Functional Materials, Mar. 2006, 16 (5), 640-648.
MacEwan et al., "Applications of elastin-like polypeptides in drug delivery," Journal of Controlled Release, Sep. 2014, 190: p. 314-330.
MacEwan et al., "Controlled apoptosis by a thermally toggled nanoscale amplifier of cellular uptake," Nano Letters, Apr. 2014, 14, 2058-2064.
MacEwan et al., "Digital switching of local arginine density in a genetically encoded self-assembled polypeptide nanoparticle controls cellular uptake," Nano Lett., Jun. 2012, 12, 3322- 3328.
MacEwan et al., "Elastin-like polypeptides: Biomedical applications of tunable biopolymers," Biopolymers, Jan. 2010, 94, 60-77.
MacEwan et al., "Non-chromatographic Purification of Recombinant Elastin-like Polypeptides and their Fusions with Peptides and Proteins from Escherichia coli," Jun. 2014, 88, p. e51583.
MacEwan et al., "Phase Behavior and Self-Assembly of Perfectly Sequence-Defined and Monodisperse Multiblock Copolypeptides," Biomacromolecules, Jan. 2017, 18(2):599-609.
Mack et al., "Antiobesity action of peripheral exenatide (exendin-4) in rodents: effects on food intake, body weight, metabolic status and side-effect measures," Int. J. Obes. Sep. 30, 2006, 1332-1340.
MacKay et al., "Self-assembling chimeric polypeptide-doxorubicin conjugate nanoparticles the abolish tumors after single injection," Nat Mater, Dec. 2009, 8(12):993-999.
Maeda et al., "Tumor vascular permeability and the EPR effect in macromolecular therapeutics: a review," J. Control. Release, Mar. 2000, 65(1-2)271-284.
Maeda et al., "Tumoritropic and lymphotropic principles of macromolecular drugs," Critical reviews in therapeutic drug carrier systems, 1989, 6(3):193-210.
Maeda, "The enhanced permeability and retention (EPR) effect in tumor vasculature: the key role of tumor-selective macromolecular drug targeting," Advances in Enzyme Regulation, 2001, 41(1):189-207.
Magnusson et al., "In Situ Growth of Side-Chain PEG Polymers from Functionalized Human Growth Hormone—A New Technique for Preparation of Enhanced Protein-Polymer Conjugates," Bioconjugate Chem. Mar. 21, 2010, 671-678.
Magnusson et al., "Ion-Sensitive "Isothermal" Responsive Polymers Prepared in Water," Journal of the American Chemical Society, Aug. 2008, 130, 10852-10853.
Maitra et al., "Pancreatic Cancer," Annu Rev Pathol Mech Dis, Feb. 2008, 3, 157-188.
Malam et al., "Liposomes and nanoparticles: nanosized vehicles for drug delivery in cancer," Trends Pharmacol Sci, Cell Press, Nov. 2009, 30(11):592-9.
Malik et al., "Recent advances in protein and peptide drug delivery systems," Curr. Drug Deliv. Apr. 2, 2007, 141-151.
Manders et al., "Dynamics of three-dimensional replication patterns during the S-phase, analysed by double labelling of DNA and confocal microscopy," Journal of cell science, 1992, 103(Pt 3):857-862.
Mann et al., "Proteomic analysis of post-translational modifications," Nat. Biotechnol., 2003, 21, 255-61.
Manzoor et al., "Overcoming limitations in nanoparticle drug delivery: triggered, intravascular release to improve drug penetration into tumors," Cancer Res, Nov. 2012, 72, 5566-5575.
Mao et al., "DNA repair by nonhomologous end joining and homologous recombination during cell cycle in human cells," Cell cycle, Sep. 2008, 7, 2902-2906.
Mao et al., "Net charge per residue modulates conformational ensembles of intrinsically disordered proteins," Proc Natl Acad Sci U S A, 2010, 107(18):8183-8188.
Mao et al., "Sortase-mediated protein ligation: a new method for protein engineering," J. Am. Chem. Soc., 2004, 126(9):2670-2671.
Maraffini et al., "Sortases and the art of anchoring proteins to the envelopes of Gram-positive bacteria," Microbiol Mol Biol Rev, Mar. 2006, 70(1):192-221.
Mariam et al., "Albumin corona on nanoparticles—a strategic approach in drug delivery," Drug Deliv., Oct. 2016, 23 (8), 2668-2676.
Marr et al., "Effect of Temperature on the Composition of Fatty Acids in Escherichia coli," J Bacteriol., 1962, 84(6):1260-7.
Marten et al., "A randomized multicentre phase II trial comparing adjuvant therapy in patients with interferon alpha-2b and 5-FU alone or in combination with either external radiation treatment and cisplatin (CapRI) or radiation alone regarding event-free survival—CapRI-2," BMC Cancer, Feb. 2009, 9, 1-8.
Maskarinec et al., "Protein engineering approaches to biomaterials design," Curr. Opin. Biotechnol., 2005, 16, 422-426.
Masood, "Polymeric nanoparticles for targeted drug delivery system for cancer therapy," Mater Sci Eng C Mater Biol Appl, Mar. 2016, 60:569-578.
Massey et al., "Self-Assembly of a Novel Organometallic-Inorganic Block Copolymer in Solution and the Solid State: Nonintrusive Observation of Novel Wormlike Poly(ferrocenyldimethylsilane)-b-Poly(dimethylsiloxane) Micelles," J. Am. Chem. Soc. 1998, 120(37):9533-9540.
Mastria et al., "Doxorubicin-conjugated polypeptide nanoparticles inhibit metastasis in two murine models of carcinoma," J Control Release, Jun. 2015, 208:52-8.
Mastria et al., "Nanoparticle formulation improves doxorubicin efficacy by enhancing host antitumor immunity," J Control Release, Jan. 2018, 269:364-373.
Matsumura et al., "A new concept for macromolecular therapeutics in cancer chemotherapy: mechanism of tumoritropic accumulation of proteins and the antitumor agent smancs," Cancer Res. 1986, 46, 6387-6392.
Matsumura, "Cancer stromal targeting (CAST) therapy," Advanced Drug Delivery Reviews, Jun. 2012, 64, 710-719.
Matthews et al., "Pharmacodynamics, Pharmacokinetics, Safety, and Tolerability of Albiglutide, a Long-Acting Glucagon-Like Peptide-1

(56) References Cited

OTHER PUBLICATIONS

Mimetic, in Patients with Type 2 Diabetes," J Clin Endocrinol Metab, Dec. 2008, 93(12):4810-4817.
Matyjaszewski et al., "Atom transfer radical polymerization," Chem. Rev. 101, Sep. 2001, 2921-2990.
Matyjaszewski et al., "Macromolecular engineering by atom transfer radical polymerization," J. Am. Chem. Soc. 136, 2014, 6513-6533.
Maurer-Stroh et al., "N-terminal N-myristoylation of proteins: prediction of substrate proteins from amino acid sequence" J Mol Biol., 2002, 317(4):541-557.
Maurer-Stroh et al., "N-terminal N-myristoylation of proteins: Refinement of the sequence motif and its taxon-specific differences," J Mol Biol., 2002, 317(4):523-540.
Mayo et al., "Cell Adhesion Promoting Peptide GVKGDKGNPGWPGAP from the Collagen Type IV Triple Helix: Cis/Trans Proline-Induced Multiple 1H NMR Conformations and Evidence for a KG/PG Multiple Turn Repeat Motif in the All-Trans proline State," Biochemistry, 1991, 30: 8251-8267.
McConkey et al., "Molecular Characterization of Pancreatic Cancer Cell Lines," Pancreatic Cancer, Jan. 2010, 457-469.
McDaniel et al., "A unified model for de novo design of elastin-like polypeptides with tunable inverse transition temperatures," Biomacromolecules, Aug. 2013, 14(8):2866-2872.
McDaniel et al., "Actively targeting solid tumours with thermoresponsive drug delivery systems that respond to mild hyperthermia," Int J Hyperthermia, Aug. 2013, 29, 501-510.
McDaniel et al., "Doxorubicin-conjugated chimeric polypeptide nanoparticles that respond to mild hyperthermia," Control. Release, May 2012, 159 (3), 362-367.
McDaniel et al., "Drug delivery to solid tumors by elastin-like polypeptides," Adc. Drug Deliver. Rev., Dec. 2010, 62(15):1456-1467.
McDaniel et al., "Noncanonical Self-Assembly of Highly Asymmetric Genetically Encoded Polypeptide Amphiphiles into Cylindrical Micelles," Nano Lett., Sep. 2014, 14(11):6590-6598.
McDaniel et al., "Rational design of "heat seeking" drug loaded polypeptide nanoparticles that thermally target solid tumors," Nano Letters, Apr. 2014, 14, 2890-2895.
McDaniel et al., "Recursive Directional Ligation by Plasmid Reconstruction Allows Rapid and Seamless Cloning of Oligomeric Genes," Biomacromolecules, Feb. 2010, 11(4):944-952.
McDaniel et al., "Self-assembly of thermally responsive nanoparticles of a genetically encoded peptide polymer by drug conjugation," Chem. Int. Ed. Feb. 2013, 52, 1683-1687.
McDaniel, "Assembly of Highly Asymmetric Genetically-Encoded Amphiphiles for Thermally Targeted Delivery of Therapeutics," Dissertation, 2013, 295 pages, Published Mar. 1, 2014.
McHale et al., "Synthesis and in vitro evaluation of enzymatically cross-linked elastin-like polypeptide gels for cartilaginous tissue repair," Tissue Eng., 2005, 11, 1768-1779.
McIlhinney et al., "Characterization of a polyhistidine-tagged form of human myristoyl-CoA: protein N-myristoyltransferase produced in *Escherichia coli*," European Journal of Biochemistry, 1994, 222(1):137-146.
McKenzie et al., "Multivalent Binding of a Ligand-Coated Particle: Role of Shape, Size, and Ligand Heterogeneity," Biophys J, Apr. 2018, 114(8):1830-1846.
Meier et al., "Determination of Optimal Sample Size for Quantification of β-Cell Area, Amyloid Area and β-Cell Apoptosis in Isolated Islets," J Histochem Cytochem, Aug. 2015, 63(8):663-673.
Mejuch et al., "Synthesis of lipidated proteins," Bioconjug. Chem. Jul. 27, 2016, 1771-1783.
Meng et al., "Stimuli-responsive polymersomes for programmed drug delivery," Biomacromolecules, ACS Publications, Feb. 2009, 10(2):197-209.
Merkel et al., "Using mechanobiological mimicry of red blood cells to extend circulation times of hydrogel microparticles," Proc Natl Acad Sci U S A, The National Academy of Sciences of the USA, Jan. 2011, 108(2):586-91.
Mero et al., "Transglutaminase-mediated PEGylation of proteins: direct identification of the sites protein modification by mass spectrometry using a novel monodisperse PEG," Bioconjug Chem, Feb. 2009, 20(2):384-389.
Merriam Webster Dictionary, "Plurality," <https://www.merriam-webster.com/dictionary/plurality> webpage accessed Jun. 25, 2020.
Merrick et al., "Seed fixity in the prostate/periprostatic region following brachytherapy," International journal of radiation oncology, biology, physics, 2000, 46, 215-220.
Meyer et al., "Drug targeting using thermally responsive polymers and local hyperthermia," Journal of Controlled Release, 2001, 74, 213-224.
Meyer et al., "Genetically Encoded Synthesis of Protein-Based Polymers with Precisely Specified Molecular Weight and Sequence by Recursive Directional Ligation: Examples from the Elastin-like Polypeptide System," Biomacromolecules, 2002, 3:357-367.
Meyer et al., "Purification of recombinant proteins by fusion with thermally-responsive polypeptide," Nat. Biotechnol., 1999, 17(11):1112-1115.
Meyer et al., "Quantification of the effects of chain length and concentration on the thermal behavior of elastin-like polypeptides," Biomacromolecules, 2004, 5(3):846-51.
Meyer et al., "Targeting a Genetically Engineered Elastin-Like Polypeptide to Solid Tumors by Local Hyperthermia," Cancer Res., 2001, 61(4):1548-1554.
Miao et al., "Sequence and domain arrangements influence mechanical properties of elastin-like polymeric elastomers," Biopolymers, Jun. 2013, 99, 392-407.
Miao et al., "Structural determinants of cross-linking and hydrophobic domains for self-assembly of elastin-like polypeptides," Biochemistry, 2005, 44, 14367-14375.
Michl et al., "Current concepts and novel targets in advanced pancreatic cancer," Gut, Jan. 2013, 62, 317-326.
Micsonai et al. "Accurate secondary structure prediction and fold recognition for circular dichroism spectroscopy," Proc Natl Acad Sci U S A, Jun. 2015, 112, E3095-3103.
Milenic et al., "Antibody-targeted radiation cancer therapy," Nature Reviews Drug Discovery, 2004, 3, 488-498.
Miller et al., "Solubilized, Spaced Polyalanines: A Context-Free System for Determining Amino Acid α-Helix Propensities," Journal of the American Chemical Society, 2002, 124, 945-962.
Mitragotri et al., "Physical approaches to biomaterial design," J. Nat Mater, Nature Publishing Group, Jan. 2009, 8(1):15-23.
Miyata et al., "Polymeric micelles for nano-scale drug delivery," Reaction & Functional Polymers, Mar. 2011, 71, 227-234.
Mjelle et al., "Cell cycle regulation of human DNA repair and chromatin remodeling genes," DNA Repair, Jun. 2015, 30, 53-67.
Modery et al., "Heteromultivalent liposomal nanoconstructs for enhanced targeting and shear-stable binding to active platelets for site-selective vascular drug delivery," Biomaterials, Elsevier, Dec. 2011, 32(35):9504-9514.
Molliex et al., "Phase separation by low complexity domains promotes stress granule assembly and drives pathological fibrillization," Cell, Sep. 2015, 163(1):123-133.
Moosmann et al., "Alpha complementation of LacZ in mammalian cells," Nucleic Acids Res, 1996, 24(6):1171-1172.
Morgan et al., "The combination of epidermal growth factor receptor inhibitors with gemcitabine and radiation in pancreatic cancer," Clin Cancer Res, Aug. 2008, 14, 5142-5149.
Mosbach et al., "Formation of proinsulin by immobilized Bacillus subtilis," Nature, 1983, 302, 543-545.
Mozhdehi et al., "Genetically Encoded Cholesterol-Modified Polypeptides," Journal of the American Chemical Society, Jan. 2019, 141(2):945-951.
Mozhdehi et al., "Genetically encoded lipid-polypeptide hybrid biomaterials that exhibit temperature-triggered hierarchical self-assembly," Nature chemistry, May 2018, 10(5):496-505.
Mu et al., "FGF21 Analogs of Sustained Action Enabled by Orthogonal Biosynthesis Demonstrate Enhanced Antidiabetic Pharmacology in Rodents," Diabetes, Feb. 2012, 61(2):505-512.
Muiznieks et al., "Modulated growth, stability and interactions of liquid-like coacervate assemblies of elastin," Matrix Biology 36, Jun. 2014, pp. 39-50.

(56) References Cited

OTHER PUBLICATIONS

Muiznieks et al., "Proline periodicity modulates the self-assembly properties of elastin-like polypeptides," J Biol Chem, The American Society for Biochemistry and Molecular Biology, Inc, Dec. 2010, 285(51):39779-39789.

Muiznieks et al., "Structural changes and facilitated association of tropoelastin," Archives of Biochemistry and Biophysics, 2003, 410, 317-323.

Muñoz et al., "Elucidating the folding problem of helical peptides using empirical parameters," Nature Structural Biology, 1994, 1, 399-409.

Muñoz et al., "Elucidating the Folding Problem of Helical Peptides using Empirical Parameters. II†. Helix Macrodipole Effects and Rational Modification of the Helical Content of Natural Peptides," Journal of Molecular Biology, 1995, 245, 275-296.

Muñoz et al., "Elucidating the folding problem of helical peptides using empirical parameters. III. Temperature and pH dependence," J Mol Biol, 1995, 245, 297-308.

Muralidharan et al., "Protein Ligation: an Enabling Technology for the Biophysical Analysis of Proteins," Nature Methods, Jun. 2006, vol. 3, No. 6, pp. 429-438.

Muro, "Challenges in design and characterization of ligand-targeted drug delivery systems," J Control Release, Elsevier, Dec. 2012, 164(2):125-37.

Murphy et al., "A dosimetric model of duodenal toxicity after stereotactic body radiotherapy for pancreatic cancer," Int J Radiation Oncology Biol Phys, Dec. 2010, 78, 1420-1426.

Na et al., "Thermoresponsive pore structure of biopolymer microspheres for a smart drug carrier," Langmuir, Jun. 2010, 26, 11165-11169.

Nagarsekar et al., "Genetically Engineered Polymers for Drug Delivery," Journal of Drug Targeting, 1999, 7(1):11-32.

Nahire et al., "Multifunctional Polymersomes for Cytosolic Delivery of Gemcitabine and Doxorubicin to Cancer Cells," Biomaterials, Aug. 2014, 35(24):6482-6497.

Nairn et al., "A Synthetic Resilin Is Largely Unstructured," Biophysical Journal, Oct. 2008, vol. 95 3358-3365.

Nakaoka et al., "Prolongation of the serum half-life period of superoxide dismutase by poly(ethylene glycol) modification," Journal of Controlled Release, 1997, 46(3):253-261.

Nanoprecision Medical, "Pipeline, Type II Diabetes," <http://www.nanoprecisionmedical.com/pipeline/diabetes> webpage available as early as Aug. 2018.

Napier et al., "Nanoparticle drug delivery platform," Journal of Macromolecular Science, Part C: Polymer Reviews, Taylor & Francis Group, LLC, Aug. 2007, 47(3):321-327.

National Institute of Mental Health, "Methods and Welfare Considerations in Behavioral Research with Animals: Report of a National Institutes of Health Workshop," NIH Publication No. 02-54083, Washington, DC: U.S. Government Printing Office. (Mar. 2002).

Nauck "Glucagon-like Peptide 1 (GLP-1) in the Treatment of Diabetes," Horm Metab Res, 2004, 36(11/12):852-858 (in English).

Nayeem et al., "Engineering enzymes for improved catalytic efficiency: a computational study of site mutagenesis in epothilone-B hydroxylase," Protein Eng Des Sel, Oxford Academy, Apr. 2009, 22(4):257-266.

Neidigh et al., "Exendin-4 and glucagon-like-peptide-q: NMR structural comparisons in the solution and micelle-associated states," Biochemistry 40, 2001, 13188-13200.

Nettles et al., "Applications of elastin-like polypeptides in tissue engineering," Adv Drug Deliv Rev, Dec. 2010, 62, 1479-1485.

Nettles et al., "In situ crosslinking elastin-like polypeptide gels for application to articular cartilage repair in a goat osteochondral defect model," Tissue Eng Part A, Jul. 2008, 14, 1133-1140.

Newcomb et al., "Advances in cryogenic transmission electron microscopy for the characterization of dynamic self-assembling nanostructures," Current Opinion in Colloid and Interface Science, Dec. 2012, 17, 350-359.

Newton et al., "Commissioning a small-field biological irradiator using point, 2D, and 3D dosimetry techniques," Medical Physics, Dec. 2011, 38, 6754-6762.

Ni et al., "Engineering of inorganic nanoparticles as magnetic resonance imaging contrast agents," Chem Soc Rev, Nov. 2017, 46(23):7438-7468.

Nichols et al., "Claudin 4 protein expression in primary and metastatic pancreatic cancer," Am J Clin Pathol, 2004, 121, 226-230.

Nicolas et al., "Fluorescently tagged polymer bioconjugates from protein derived macroinitiators," Chem. Commun. Jan. 2007, 45, 4697-4699.

Nie, "Understanding and overcoming major barriers in cancer nanomedicine," Nanomedicine (Lond) Jun. 2010, 5 (4), 523-528.

Nielsen, "Incretin mimetics and DPP-IV inhibitors for the treatment of type 2 diabetes," Drug Discov. Today 10, 2005, 703-710.

Nies et al., "Fibroblast Growth Factor Signaling in Metabolic Regulation," Front Endocrinol, Jan. 2016, 6(193) (in English).

Nilvebrant et al., "The albumin-binding domain as a scaffold for protein engineering," Computational and Structural Biotechnology Journal, Mar. 2013, 6: e201303009, 8 pages.

Niu et al., "The role of adhesion molecules, αvβ3, αvβ5 and their ligands in the tumor cell and endothelial cell adhesion," Eur J Cancer Prev, Wolters Kluwer, Dec. 2007, 16(6):517-27.

Nott et al., "Phase transition of a disordered nuage protein generates environmentally responsive membraneless organelles," Mol Cell, Mar. 2015, 57(5):936-947.

Nucci et al., "The therapeutic value of poly(ethylene glycol)-modified proteins," Adv. Drug Deliv. Rev., 1991, 6(2):133-151.

Nuhn et al., "Secondary structure formation and LCST behavior of short elastin-like peptides," Biomacromolecules, Sep. 2008, 9, 2755-2763.

O'Day et al., "Therapeutic Protein-polymer Conjugates: Advancing beyond PEGylation," J. Am. Chem. Soc., Sep. 2014, vol. 136, pp. 14323-14332.

Ogawara et al., "Pre-coating with serum albumin reduces receptor-mediated hepatic disposition of polystyrene nanosphere: implications for rational design of nanoparticles," Journal of Controlled Release, 2004, 100(3): 451-455.

Olafsen et al., "Covalent disulfide-linked anti-CEA diabody allows site-specific conjugation and radiolabeling for tumor targeting applications," Protein Engineering, Design & Selection, 2004, 17(1):21-27.

Ortega et al., "Hydrodynamic properties of rodlike and dislike particles in dilute solution," The Journal of Chemical Physics, 2003, 119(18):9914-9919.

Ortony et al., "Internal dynamics of a supramolecular nanofibre," Nat. Mater., Aug. 2014, 13, 1-5.

Ozer et al., "Site-Specific and Stoichiometric Stealth Polymer Conjugates of Therapeutic Peptides and Proteins," Bioconjug Chem, Mar. 2017, 28(3):713-723.

Pace et al., "How to measure and predict the molar absorption coefficient of a protein" Protein Science 1995, 4: 2411-2423.

Pagani et al., "International guidelines for management of metastatic breast cancer: can metastatic breast cancer be cured?," Journal of the National Cancer Institute, Apr. 2010, 102, 456-463.

Pak et al., "Sequence Determinants of Intracellular Phase Separation by Complex Coacervation of a Disordered Protein," Mol Cell, Jul. 2016, 63(1):72-85.

Palmerston Mendes et al., "Dendrimers as Nanocarriers for Nucleic Acid and Drug Delivery in Cancer Therapy," Molecules, Aug. 2017, 22(9):1401.

Palta et al., "Interim Acute Toxicity Analysis and Surgical Outcomes of Neoadjuvant Gemcitabine/nab-Paclitaxel and Hypofractionated Image Guided Intensity Modulated Radiation Therapy in Resectable and Borderline Resectable Pancreatic Cancer (Anchor) Study," International Journal of Radiation Oncology • Biology • Physics, Oct. 2016, 96, S204-S205.

Palva et al., "Secretion of interferon by Bacillus subtilis," Gene, 1983, 22, 229-235.

Pang et al., "A Modular Method for the High-Yield Synthesis of Site-Specific Protein-Polymer Therapeutics," Angew Chem Int Ed Engl, Jul. 2016, 55, 10296-10300.

(56) References Cited

OTHER PUBLICATIONS

Paolino et al., "Folate-targeted supramolecular vesicular aggregates as a new frontier for effective anticancer treatment in in vivo model," Eur. J. Pharm. Biopharm., Jun. 2012, 82(1):94-102.

Paolino et al., "Gemcitabine-loaded PEGylated unilamellar liposomes vs Gemzar: biodistribution, pharmacokinetic features and in vivo antitumor activity," J. Control. Release Jun. 2010, 144(2):144-150.

Paoloni et al., "Translation of new cancer treatments from pet dogs to humans," Nat. Rev. Cancer Feb. 2008, 8 (2), 147-156.

Papa et al., "PEGylated Liposomal Gemcitabine: Insights Into a Potential Breast Cancer Therapeutic," Cell Oncol. (Dordr), Oct. 2013, 36(6):449-457.

Paramonov et al., "Self-assembly of peptide-amphiphile nanofibers: The roles of hydrogen bonding and amphiphilic packing," J. Am. Chem. Soc., May 2006, 128, 7291-7298.

Pardridge, "The blood-brain barrier: bottleneck in brain drug development," NeuroRx, 2005, 2(1):3-14.

Park et al., "Exendin-4 and exercise improve hepatic glucose homeostasis by promoting insulin signaling in diabetic rats," Metabolism, Jan. 2010, 59, 123-133.

Park et al., "Formulation optimization and in vivo proof-of-concept study of thermosensitive liposomes balanced by phospholipid, elastin-like polypeptide, and cholesterol," PLoS One, Jul. 2014, 9: e103116, 13 pages.

Park et al., "Protein stitchery: Design of a protein for selective binding to a specific DNA sequence," PNAS, 1992, vol. 89:9094-9096.

Parker et al., "Antibody mimics based on human fibronectin type three domain engineered for thermostability and high-affinity binding to vascular endothelial growth factor receptor two," Protein Eng Des Sel, 2005, 18(9):435-44.

Parkes et al. "Discovery and development of exenatide: the first antidiabetic agent to leverage the multiple benefits of the incretin hormone, GLP-1," Expert Opinion. Drug Deliv., Feb. 2013, 8(2):219-244.

Parveen et al., "Nanomedicine," Clinical Pharmacokinetics, Oct. 2006, 45(10):965-988.

Pastuszka et al., "A tunable and reversible platform for the intracellular formation of genetically engineered protein microdomains," Biomacromolecules, ACS Publications, Oct. 2012, 13(11):3439-3444.

Patil et al., "Cellular delivery of doxorubicin via pH-controlled hydrazone linkage using multifunctional nano vehicle based on poly(beta-I-malic acid)," Int J Mol Sci, Sep. 2012, 13, 11681-11693.

Peeler et al., "Genetically encoded initiator for polymer growth from proteins," J. Am. Chem. Soc. 132, Oct. 2010, 13575-13577.

Peng et al., "Length-dependent prediction of protein intrinsic disorder," BMC Bioinformatics, Springer Nature, Apr. 2006, 7:208.

Peters, "Serum albumin," Adv. Protein Chem. 37, 1985, 161-245.

Petitdemange et al., "Tuning Thermoresponsive Properties of Cationic Elastin-like Polypeptides by Varying Counterions and Side-Chains," Bioconjug. Chem., May 2017, 28(5):1403-1412.

Petros et al., "Strategies in the design of nanoparticles for therapeutic applications," Nat Rev Drug Discov, Nature Research, Aug. 2010, 9(8):615-27.

Phan et al., "Temperature-responsive self-assembly of charged and uncharged hydroxyethylcellulose-graft-poly(N-isopropylacrylamide) copolymer in aqueous solution," Colloid Polym. Sci., Apr. 2011, 289 (9), 993-1003.

Pinkas et al., "Tunable, post-translational hydroxylation of collagen domains in *Escherichia coli*," ACS Chem. Biol., Apr. 2011, 6(4):320-324.

Pliarchopoulou et al., "Pancreatic cancer: Current and future treatment strategies," Cancer Treatment Reviews, Aug. 2009, 35, 431-436.

Poitout et al., "Glucolipotoxicity: Fuel Excess and β-Cell Dysfunction," Endocr Rev, May 2008, 29(3):351-366.

Pometun et al., "Quantitative observation of backbone disorder in native elastin," J Biol Chem, 2004, 279, 7982-7987.

Popp et al., "Site-specific labeling via sortase-mediated transpeptidation," Curr. Protoc. Protein Sci. 56, Apr. 2009, 15.13.1-15.13.9.

Popp et al., "Sortase-Catalyzed Transformations That Improve the Properties of Cytokines," PNAS, Feb. 2011, vol. 108, No. 8, pp. 3169-3174.

Potters et al., "12-year outcomes following permanent prostate brachytherapy in patients with clinically localized prostate cancer," The Journal of urology, 2005, 173, 1562-1566.

Potters et al., "Monotherapy for stage T1-T2 prostate cancer: radical prostatectomy, external beam radiotherapy, or permanent seed implantation," Radiotherapy and oncology: journal of the European Society for Therapeutic Radiology and Oncology, 2004, 71, 29-33.

Potters et al., "Potency after permanent prostate brachytherapy for localized prostate cancer," International journal of radiation oncology, biology, physics, 2001, 50(5): 1235-1242.

Potthoff et al., "Endocrine fibroblast growth factors 15/19 and 21: from feast to famine," Genes Dev, Feb. 2012, 26(4):312-324.

Prestwich et al., "Beta dose point kernels for radionuclides of potential use in radioimmunotherapy," J Nucl Med, 1989, 30, 1036-1046.

Privratsky et al., "PECAM-1: regulator of endothelial junctional integrity," Cell Tissue Res, Mar. 2014, 355, 607-619.

Prostate Seed Center, "Brachytherapy seed pre-plan rendering," <http://www.prostateseedcenter.com/dynamics-of-brachytherapy> webpage available as early as Aug. 30, 2012.

Provenzano et al., "Enzymatic targeting of the stroma ablates physical barriers to treatment of pancreatic ductal adenocarcinoma," Cancer cell, Mar. 2012, 21, 418-429.

Provenzano et al., "Hyaluronan, fluid pressure, and stromal resistance in pancreas cancer," Br J Cancer, Jan. 2013, 108, 1-8.

Pulaski et al., "Mouse 4T1 breast tumor model," Curr. Protoc. Immunol., 2001, Chapter 20, Unit 20.2.

Qamar et al., "FUS Phase Separation Is Modulated by a Molecular Chaperone and Methylation of Arginine Cation-pi Interactions," Cell, Apr. 2018, 173(3):720-734.e15.

Qi et al., "A brush-polymer conjugate of exendin-4 reduces blood glucose for up to five days and eliminates poly(ethylene glycol) antigenicity," Nat Biomed Eng, Nov. 2016, 1:0002.

Qi et al., Dataset for a brush-polymer conjugate of exendin-4 reduces blood glucose for up to five days and eliminates poly(ethylene glycol) antigenicity. Figshare, Nov. 2016, <http://dx.doi.org/10.6084/m9.figshare.3976761>.

Qi et al., "Growing polymers from peptides and proteins: a biomedical perspective," Polym. Chem., Jan. 2014, 5(2):266-276.

Qi et al., "Protein-polymer conjugation—moving beyond PEGylation," Curr. Opin. Chem. Biol. 28, Oct. 2015, 181-193.

Qi et al., "Sortase-catalyzed initiator attachment enables high yield growth of a stealth polymer from the C terminus of a protein," Macromol. Rapid Commun., Aug. 2013, 34(15):1256-1260.

Qiu et al., "Development of Orthotopic Pancreatic Tumor Mouse Models," Methods Mol Biol, Jan. 2013, 980: 215-223.

Qiu et al., "Polymer Architecture and Drug Delivery," Pharmaceutical Research, Feb. 2006, 23(1):1-30.

Quarmby et al., "Irradiation induces upregulation of CD31 in human endothelial cells," Arterioscler Thromb Vasc Biol, 1999, 19, 588-597.

Quarmby et al., "Radiation-induced normal tissue injury: role of adhesion molecules in leukocyte-endothelial cell interactions," Int J Cancer, 1999, 82, 385-395.

Quiroz et al., "Intrinsically disordered proteins access a range of hysteretic phase separation behaviors," Scientific advances, Oct. 2019, 5(10):eaax5177.

Quiroz et al., "Sequence heuristics to encode phase behaviour in intrinsically disordered protein polymers," Nat. Mater., Nov. 2015, 14(11):1164-1171.

Rabotyagova et al., "Protein-based block copolymers," Biomacromolecules, Feb. 2011, 12(2): 269-289.

Radivojac et al., "Intrinsic Disorder and Functional Proteomics," Biophysical Journal, Mar. 2007, vol. 92, Issue 5, pp. 1439-1456.

Ragupathi et al., "Abstract A73: Antitumor activity of MVT-5873, a monoclonal antibody targeting sialyl Lewisa, alone and in combination with gemcitabine/nab-paclitaxel in a BxPC3 human pancreatic cancer xenograft model," Cancer Research, Dec. 2016, 76.

(56) References Cited

OTHER PUBLICATIONS

Rankine et al., "Investigating end-to-end accuracy of image guided radiation treatment delivery using a micro-irradiator," Physics in Medicine and Biology, Nov. 2013, 58(21): 7791-7801.
Rao et al., "Synthetic nanoparticles camouflaged with biometric erythrocyte membranes for reduced reticuloendothelial system uptake," Nanotechnology, Jan. 2016, 27 (8), 85106, 9 pages.
Rapaka et al., "Coacervation of Sequential Polypeptide Models of Tropoelastin," Int J Peptide Protein Res, 1978, 11: 97-108.
Ratner et al., "Radiation-grafted hydrogels for biomaterial applications as studied by the ESCA technique," Journal of Applied Polymer Science, 1978, 22, 643-664.
Ratner, "A pore way to heal and regenerate: 21st century thinking on biocompatibility," Regen Biomater, Feb. 2016, 3(2):107-110.
Rauscher et al. "Proline and Glycine Control Protein Self-Organization into Elastomeric or Amyloid Fibrils," Structure, Nov. 2006, 14(11):1667-1676.
Ravikumar et al., "Mimicking adhesive functionalities of blood platelets using ligand-decorated liposomes," Bioconjugate chemistry, ACS Publications, May 2012, 23(6):1266-1275.
Ray et al., "Aptamer-mediated delivery of chemotherapy to pancreatic cancer cells." Nucleic acid therapeutics, Oct. 2012, 22(5): 295-305.
Regier et al., American Heart Association 2014 Scientific Sessions, May 2015, vol. 7, pp. 299-303.
Reguera et al., "Thermal Behavior and Kinetic Analysis of the Chain Unfolding and Refolding and of the Concomitant Nonpolar Solvation and Desolvation of Two Elastin-like Polymers," Macromolecules, 2003, 36, 8470-8476.
Ren et al., "Mesenchymal stem cell-mediated immunosuppression occurs via concerted action of chemokines and nitric oxide," Cell Stem Cell, Feb. 2008, 2(2): p. 141-150.
Ribeiro et al., "Influence of the amino-acid sequence on the inverse temperature transition of elastin-like polypeptides," Biophysical Journal, Jul. 2009, 97(1):312-320.
Richards et al., "Engineered fibronectin type III domain with a RGDWE sequence binds with enhanced affinity and specificity to human $\alpha v\beta 3$ integrin," J Mol Biol, 2003, 326(5):1475-1488.
Richards et al., "Man's best friend: what can pet dogs teach US about non-Hodgkin lymphoma?" Inmunol Rev., Jan. 2015, 263 (1): 173-191.
Riddles et al., "Ellman's reagent: 5,5'-dithiobis(2-nitrobenzoic acid)—a reexamination," Anal Biochem. 1979, 94(1):75-81.
Riedel et al., "Engineered glucagon-like peptide-1-producing hepatocytes lower plasma glucose levels in mice," Am J Physiol Endocrinol Metab, Apr. 2009, 296(4):E936-E944.
Rincon et al., "Biocompatibility of elastin-like polymer poly(VPAVG) microparticles: in vitro and in vivo studies," Journal of Biomedical Materials Research, 2005, 78A, 343-351.
Rios-Doria et al., "Doxil synergizes with cancer immunotherapies to enhance antitumor responses in syngeneic mouse models," Neoplasia, Aug. 2015, 17(8):661-670.
Ritcher et al., "Antibodies against polyethylene glycol produced in animals by immunization with monomethoxy polyethylene glycol modified proteins," Int. Arch. Allergy Appl. Immunol. 70, 1983, 124-131.
Ritcher et al., "Polyethylene glycol reactive antibodies in man: titer distribution in allergic patients treated with monomethoxy polyethylene glycol modified allergens or placebo, and in healthy blood donors," Int. Arch. Allergy Appl. Immunol. 74, 1984, 36-39.
Rivory et al., "Effects of lipophilicity and protein binding on the hepatocellular uptake and hepatic disposition of two anthracyclines, doxorubicin and iododoxorubicin," Cancer Chemother Pharmacol, 1996, 38(5):439-445.
Roberts et al., "Elastin-like polypeptides as models of intrinsically disordered proteins," FEBS Lett., Sep. 2015, 589, 2477-2486.
Robinet et al. "Elastin-derived peptides enhance angiogenesis by promoting endothelial cell migration and tubulogenesis through upregulation of MT1-MMP," J. Cell Science, 2005, 118:343-356.

Rodriguez-Diaz et al., "Alpha cells secrete acetylcholine as a non-neuronal paracrine signal priming beta cell function in humans," Nat Med, Jun. 2011, 17:888-892.
Rolland et al., "Direct fabrication and harvesting of monodisperse, shape-specific nanobiomaterials," J Am Chem Soc, 2005, 127(28):10096-100.
Röomer et al., "The elaborate structure of spider silk: structure and function of a natural high performance fiber," Prion, Nov. 2008, 2(4):154-161.
Roopenian et al., "FcRn: the neonatal Fc receptor comes of age," Nat. Rev. Immunol., Sep. 2007, vol. 7, No. 9, 715-725.
Rosenberg et al., "Present and future innovations in radiation oncology," Surg Oncol Clin N Am, Jul. 2013, 22(3):599-618.
Rosenholm et al., "Towards multifunctional, targeted drug delivery systems using mesoporous silica nanoparticles—opportunities & challenges," Nanoscale, Royal Society of Chemistry, Oct. 2010, 2(10):1870-83.
Rösler et al., "Advanced drug delivery devices via self-assembly of amphiphilic block copolymers," Advanced Drug Delivery Reviews, 2001, 53:95-108.
Rozak et al., "G148-GA3: a streptococcal virulence module with atypical thermodynamics of folding optimally binds human serum albumin at physiological temperatures," Biochim Biophys Acta, 2005, 1753(2): p. 226-33.
Ruiz van Haperen et al., "Regulation of phosphorylation of deoxycytidine and 2',2'- difluorodeoxycytidine (gemcitabine); effects of cytidine 5'-triphosphate and uridine 5'- triphosphate in relation to chemosensitivity for 2',2'-difluorodeoxycytidine," Biochem. Pharmacol. 1996, 51(7):911-908.
Russo et al., "The role of neoadjuvant therapy in pancreatic cancer: a review," Future Oncol, Mar. 2016, 12(5):669-685.
Ryerson et al., "Annual report to the nation on the status of cancer, 1975-2012, featuring the Increasing incidence of liver cancer," Cancer, May 2016, 122(9): 1312-1337.
Ryu et al., "Elastin-like polypeptide for improved drug delivery for anticancer therapy: preclinical studies and future applications," Expert Opinion on Drug Delivery, Informa Healthcare, Oct. 2014, 12(4):653-667.
Saba et al., "A Comparative Oncology Study of Iniparib Defines Its Pharmacokinetic Profile and Biological Activity in a Naturally-Occurring Canine Cancer Model," PLoS One, Feb. 2016, 11(2): 1-11.
Safran et al., "Gemcitabine, paclitaxel, and radiation for locally advanced pancreatic cancer: A phase I trial," Int J Radiation Oncology Biol Phys, 2002, 54, 137-141.
Sagle et al., "Investigating the hydrogen-bonding model of urea denaturation," J Am Chem Soc, Jun. 2009, 131(26): 9304-9310.
Saifer et al., "Selectivity of binding of PEGs and PEG-like oligomers to anti-PEG antibodies induced by methoxyPEG-proteins," Molecular Immunology, Feb. 2014, 57(2):236-246.
Sandler et al., "Gemcitabine: Single-Agent and Combination Therapy in Non-Small Cell Lung Cancer," Oncologist 1999, 4(3)241-251.
Sanna et al., "Targeted therapy using nanotechnology: focus on cancer," Int J Nanomedicine, Jan. 2014, 9:467-83.
Schaal et al., "Biopolymer ß-brachytherapy delivered with concomitant paclitaxel outperforms traditional x-ray radiation to include complete regression in multiple pancreatic tumor xenograft models through synergistic modulation of the tumor microenvironment," Poster #5831, 2018.
Schaal et al., "Injectable polypeptide micelles that form radiation crosslinked hydrogels in situ for intratumoral radiotherapy," Journal of Controlled Release, Apr. 2016, 228, 58-66.
Schellenberg et al., "Gemcitabine chemotherapy and single-fraction stereotactic body radiotherapy for locally advanced pancreatic cancer," Int J Radiation Oncol Biol Phys, Nov. 2008, 72(3): 678-686.
Schellenberg et al., "Single-fraction stereotactic body radiation therapy and sequential gemcitabine for the treatment of locally advanced pancreatic cancer," Int J Radiation Oncology Biol Phys, Sep. 2011, 81(1): 181-188.
Schellenberger et al., "A recombinant polypeptide extends the in vivo half-life of peptides and proteins in a tunable manner," Nat. Biotechnol., Dec. 2009, 27(12):1186-1188.

(56) References Cited

OTHER PUBLICATIONS

Schlaff et al., "Bringing the heavy: carbon ion therapy in the radiobiological clinical context," Radiation Oncology, Mar. 2014, 9, Article 88, 1-18.
Schneider et al., "NIH Image to ImageJ: 25 years of image analysis," Nature Methods, Jul. 2012, 9(7): 671-675.
Schnell et al., "Expression of integrin αvB3 in gliomas correlates with tumor grade and is not restricted to tumor vasculature," Brain Pathol, International Society of Neuropathology, Aug. 2008, 18(3):378-86.
Schwendeman et al., "Injectable controlled release depots for large molecules," J Control Release, Sep. 2014, 190, 240-253.
Senin et al., "N-Myristoylation of recoverin enhances its efficiency as an inhibitor of rhodopsin kinase," Febs. Lett., 1995, 376, 87-90.
Senior et al., "Val-Gly-Val-Ala-Pro-Gly, a Repeating Peptide in Elastin, Is Chemotactic for Fibroblasts and Monocytes," The Journal of Cell Biology, 1984, 99: 870-874.
Serrano et al., "An infrared spectroscopic study of the conformational transition of elastin-like polypeptides," Biophys. J., Oct. 2007, 93(7):2429-2435.
Shadwick, "Mechanical design in arteries," J Exp Biol, 1999, 202, 3305-3313.
Shang et al., "pH-Dependent Protein Conformational Changes in Albumin: Gold Nanoparticle Bioconjugates: A Spectroscopic Study," Langmuir, Feb. 2007, 23 (5), 2714-2721.
Shao et al., "Super-resolution 3D microscopy of live whole cells using structured illumination," Nat Methods, Oct. 2011, 8(12): 1044-1046.
Sharma et al., "Dendrimer nanoarchitectures for cancer diagnosis and anticancer drug delivery," Drug Discov Today, Feb. 2017, 22(2):314-326.
Sharma et al., "PLGA-based nanoparticles: A new paradigm in biomedical applications," TrAC Trends in Analytical Chemistry, Jun. 2016, 80:30-40.
Sharma et al., "Polymer particle shape independently influences binding and internalization by macrophages," Journal of Controlled Release, Elsevier, Nov. 2010, 147(3):408-412.
Shen et al., "Conjugation site modulates the in vivo stability and thearpeutic activity of antibody-drug conjugates," Nat Biotechnol, Jan. 2012, 30(2):184-189.
Sheparovych et al., "Stimuli-Responsive Properties of Peptide-Based Copolymers Studied via Directional Growth of Self-Assembled Patterns on Solid Substrate," Biomacromolecules, Jul. 2009, 10:1955-1961.
Sherman et al., "Next-Generation PEGylation Enables Reduced Immunoreactivity of PEG-Protein Conjugates," Drug and Development & Delivery, Jun. 2012, vol. 12, No. 5, 36-42.
Sherman et al., "Role of the Methoxy Group in Immune Responses to mPEG-Protein Conjugates," Bioconjugate Chemistry, Mar. 2012, 23(3): 485-499.
Shi et al., "Cell adhesion on a POEGMA-modified topographical surface," Langmuir: the ACS journal of surfaces and colloids, Dec. 2012, 28 (49), 17011-8.
Shi et al., "Triggered sorting and co-assembly of genetically engineered protein microdomains in the cytoplasm," Adv Mater, Wiley, Jan. 2014, 26(3):449-454.
Shimoboji et al., "Temperature-Induced Switching of Enzyme Activity with Smart Polymer-Enzyme Conjugates," Bioconjugate Chem. 2003, 14, 517-525.
Shin et al., "Liquid phase condensation in cell physiology and disease," Science, Sep. 2017, 357(6357):eaaf4382.
Shusharina et al., "Micelles of Diblock Copolymers with Charged and Neutral Blocks: Scaling and Mean-Field Lattice Approaches," Macromolecules, 2000, 33(10): 3892-3901.
Sickmeier et al., "DisProt: the Database of Disordered Proteins," Nucleic Acids Res, Oxford Academy, Jan. 2007, 35:D786-793.
Siegel et al., "Absorbed fractions for electrons and beta particles in spheres of various sizes," J Nucl Med, 1994, 35, 152-156.
Siegwart et al., "ATRP in the Design of Functional Materials for Biomedical Applications," Prog Polymer Science, Jan. 2012, vol. 37, No. 1, pp. 18-37.
Silberstein et al., "The SNM Practice Guideline for Therapy of Thyroid Disease with $^{131}$I, 3.0," J Nucl Med, Jul. 2012, 53, 1-19.
Silva et al., "Selective differentiation of neural progenitor cells by high-epitope density nanofibers," Science, 2004, 303, 1352-5.
Simakova et al., "Aqueous ARGET ATRP," Macromolecules, Aug. 2012, 45(16):6371-6379.
Simnick et al., "In vivo tumor targeting by a NGR-decorated micelle of a recombinant diblock copolypeptide," J Control Release, Oct. 2011, 155(2): 144-151.
Simnick et al., "Morphing low-affinity ligands into high-avidity nanoparticles by thermally triggered self-assembly of a genetically encoded polymer," ACS Nano, Apr. 2010, 4(4):2217-2227.
Simon et al., "Engineered Ribonucleoprotein Granules Inhibit Translation in Protocells," Molecular cell, Jul. 2019, 75(1):66-75.
Simon et al., "Programming molecular self-assembly of intrinsically disordered proteins containing sequences of low complexity," Nat Chem, Jun. 2017, 9(6):509-515.
Singhal et al., "Fibroblast Growth Factor 21 (FGF21) Protects against High Fat Diet Induced Inflammation and Islet Hyperplasia in Pancreas," PLoS One, Feb. 2016, 11(2):e0148252.
Sisson et al., "Radiation safety in the treatment of patients with thyroid diseases by radioiodine 131I: practice recommendations of the American Thyroid Association," Thyroid, Apr. 2011, 21(4):335-346.
Skerra, "Alternative non-antibody scaffolds for molecular recognition," Curr Opin Biotechnol, Elsevier, Aug. 2007, 18(4):295-304.
Smith et al., "The Role of Beta Cell Glucagon-like Peptide-1 Signaling in Glucose Regulation and Response to Diabetes Drugs," Cell Metab, Jun. 2014, 19(6):1050-1057.
Smits et al., "Elastin-Like Polypeptide Based Nanoparticled: Design Rationale Toward Nanomedicine," Macromolecular Bioscience, Macromolecular Journals, Jan. 2015, 15(1):36-51.
Sonawane et al., "Hydrazo linkages in pH responsive drug delivery systems," European Journal Pharmaceutical Sciences, Mar. 2017, 99, 45-65.
Sorkin et al., "Signal transduction and endocytosis: close encounters of many kinds," Nat Rev Mol Cell Biol, 2002, 3(8):600-614.
Sousa et al., "Production of a polar fish antimicrobial peptide in *Escherichia coli* using an ELP-intein tag," J Biotechnol, Sep. 2016, 234:83-89.
Sriraman et al., "Barriers to drug delivery in solid tumors," Tissue Barriers, Jul. 2014, 2(3): 2-10.
Stanislaus et al., "A Novel Fc-FGF21 With Improved Resistance to Proteolysis, Increased Affinity Toward β-Klotho, and Enhanced Efficacy in Mice and Cynomolgus Monkeys," Endocrinology, May 2017, 158(5):1314-1327.
Stefl et al., "RNA sequence-and shape-dependent recognition by proteins in the ribonucleoprotein particle" EMBO reports (2005) 6(1):33-38.
Steichen et al., "A Review of Current Nanoparticle and Targeting Moieties for the Delivery of Cancer Therapeutics," Eur J Pharm Sci, Elsevier, Feb. 2013, 48(3):416-27.
Stock et al., "Penile erectile function after permanent raioactive seed implantation for treatment of prostate cancer," The Journal of urology, 2001, 165, 436-439.
Stork et al., "A novel tri-functional antibody fusion protein with improved pharmacokinetic properties generated by fusing a bispecific single-chain diabody with an albumin-binding domain from streptococcal protein G," Protein Engineering Design and Selection, Nov. 2007, 20(11): p. 569-576.
Strohmaier et al., "Comparison of $^{60}$Co and $^{192}$Ir sources in HDR brachytherapy," J Contemp Brachyther, Dec. 2011, 3(4): 199-208.
Strulson et al., "RNA catalysis through compartmentalization," Nat Chem, Nature Publishing Group, Nov. 2012, 4(11):941-946.
Stutz et al., "Seed loss through the urinary tract after prostate brachytherapy: examining the role of cystoscopy and urine straining post implant," Medical physics, 2003, 30, 2695-2698.

(56) References Cited

OTHER PUBLICATIONS

Sugyo et al., "Evaluation of efficacy of radioimmunotherapy with 90Y-labeled fully human anti-transferring receptor monoclonal antibody in pancreatic cancer mouse models," PLoS One, Apr. 2015, 10, 1-17.

Suk et al., "PEGylation as a Strategy for Improving Nanoparticle-Based Drug and Gene Delivery," Adv Drug Deliv Rev, Apr. 2016, 99(Pt A):28-51.

Sumerlin, "Proteins as Initiators of Controlled Radical Polymerization: Grafting-from via ATRP and RAFT," ACS Macro Lett. Jan. 2012, 1(1): 141-145.

Sun et al., "Autofluorescence Imaging of Living Pancreatic Islets Reveals Fibroblast Growth Factor-21 (FGF21)-Induced Metabolism," Biophys J, Dec. 2012, 103(11):2379-2388.

Sun et al., "Contributions of the extracellular and cytoplasmic domains of platelet-endothelial cell adhesion molecule-1 (PECAM-1/CD31) in regulating cell-cell localization," J. Cell Sci., 2000, 113, 1459-1469.

Sun et al., "Efficacy and safety of the hypoxia-activated prodrug TH-302 in combination with gemcitabine and nab-paclitaxel in human tumor xenograft models of pancreatic cancer," Cancer Biology & Therapy, Feb. 2015, 16(3): 438-449.

Sun et al., "EUS-guided interstitial brachytherapy of the pancreas: a feasibility study," Gastrointestinal Endoscopy, 2005, 62, 775-779.

Sun et al., "On the Thermally Reversible Dynamic Hydration Behavior of Oligo(ethylene glycol) Methacrylate-Based Polymers in Water," Macromolecules, Jan. 2013, 46(1): 236-246.

Sunamura et al., "Gene Therapy for Pancreatic Cancer Targeting the Genomic Alterations of Tumor Suppressor Genes using Replication-selective Oncolytic Adenovirus," Human Cell, 2002, 15, 138-150.

Surwit et al., Diet-induced type II diabetes in C57BL/6J mice, Diabetes 37, 1988, 1163-1167.

Sussman et al., "Porous implants modulate healing and induce shifts in local macrophage polarization in the foreign body reaction," Ann Biomed Eng, Jul. 2014, 42(7): 1508-1516.

Swee et al., "Sortase-mediated modification of aDEC205 affords optimization of antigen presentation and immunization against a set of viral epitopes," Proc Natl Acad Sci USA, Jan. 2013, 110(4):1428-1433.

Swers et al., Multivalent Scaffold Proteins as Superagonists of Trail Receptor 2-Induced Apoptosis, Mol Cancer Ther, Jul. 2013, 12(7): 1235-1244.

Swider et al., "Customizing Poly(lactic-Co-Glycolic Acid) Particles for Biomedical Applications," Acta Biomater, Jun. 2018, 73:38-51.

Takalkar et al., "Radium-223 dichloride bone-targeted alpha particle therapy for hormone-refractory breast cancer metastatic to bone," Exp Hematol Oncol, Sep. 2014, 8, Article No. 23.

Talelli et al., "Core-Crosslinked Polymeric Micelles: Principles, Preparation, Biomedical Applications and Clinical Translation," Nano Today, Feb. 2015, 10(1):93-117.

Tallarida, "Quantitative methods for assessing drug synergism," Genes & Cancer, Nov. 2011, 2(11): 1003-1008.

Talukdar et al., "A Long-Acting FGF21 Molecule, PF-05231023, Decreases Body Weight and Improves Lipid Profile in Non-human Primates and Type 2 Diabetic Subjects," Cell Metab, Mar. 2016, 23(3):427-440.

Tamburro et al., "Dissection of human tropoelastin: exon-by-exon chemical synthesis and related conformational studies," Biochemistry, 2003, 42, 13347-13362.

Tamburro et al., "Localizing alpha-helices in human tropoelastin: assembly of the elastin "puzzle"," Biochemistry, Aug. 2006, 45(31): 9518-9530.

Tan et al., "Characterization of a new primary human pancreatic tumor line," Cancer investigation, 1986, 4, 15-23.

Tang et al., "Combinatorial codon scrambling enables scalable gene synthesis and amplification of repetitive proteins," Nature Mater., Apr. 2016, 15(4): 419-424.

Tang et al., "Enzymatic Polymerization of High Molecular Weight DNA Amphiphiles That Self-Assemble into Star-Like Micelles," Advanced Materials, Feb. 2014, 26(19): 3050-3054.

Tang et al., "High-Molecular-Weight Polynucleotides by Transferase-Catalyzed Living Chain-Growth Polycondensation," Angew. Chem., Jun. 2017, 56(24): 6778-6782.

Tang et al., "Identification of PECAM-1 in solid tumor cells and its potential involvement in tumor cell adhesion to endothelium," J. Biol. Chem., 1993, 268, 22883-22894.

Tantakitti et al., "Energy landscapes and functions of supramolecular systems," Nat. Mater., Apr. 2016, 15(4): 469-476.

Tedja et al., "Effect of TiO2 nanoparticle surface functionalization on protein adsorption, cellular uptake and cytotoxicity: the attachment of PEG comb polymers using catalytic chain transfer and thiol-ene chemistry," Polymer Chemistry, Oct. 2012, 3 (10), 2743-2751.

Teicher, "In vivo/ex vivo and in situ assays used in cancer research: a brief review," Toxicol. Pathol., Jan. 2009, 37 (1), 114-122.

Thakor et al., "Clinically Approved Nanoparticle Imaging Agents," J Nucl Med, Oct. 2016, 57(12):1833-1837.

Theillet et al., "The alphabet of intrinsic disorder: I. Act like a Pro: On the abundance and roles of proline residues in intrinsically disordered proteins," Intrinsically Disord Proteins, Taylor & Francis, Apr. 2013, 1(1):e24360.

Therasse et al., "New guidelines to evaluate the response to treatment in solid tumors," J Natl Cancer Inst, 2000, 92, 205-216.

Thorens et al., "Cloning and functional expression of the human islet GLP-1 receptor: demonstration that Exendin-4 Is an agonist and Exendin-(9-39) an antagonist of the receptor," Diabetes 42, 1993, 1678-1682.

Tomiyama et al., "Relevant use of Klotho in FGF19 subfamily signaling system in vivo," Proc Natl Acad Sci USA, Jan. 2010, 107(4):1666-71.

Tompa et al., "Fuzzy complexes: polymorphism and structural disorder in protein-protein interactions," Trends Biochem Sci, Jan. 2008, 33(1): 2-8.

Tong et al., "Protein Modification with Amphiphilic Block Copoly(2-oxazoline)s as a New Platform for Enhanced Cellular Delivery," Mol. Pharm., Aug. 2010, vol. 7, No. 4, pp. 984-992.

Ton-That et al., "Assembly of pili on the surface of Corynebacterium diptheriae," 2003, 50(4):1429-1438.

Ton-That et al., "Purification and characterization of sortase, the transpeptide that cleaves surface proteins of Staphylococcus aureus and the LPXTG motif," Proc Natl Acad Sci USA, 1999, 96(22):12424-12429.

Torchilin, "Recent advances with liposomes as pharmaceutical carriers," Nature Rev. Drug Discov. 2005, 4(2):145-160.

Towler et al., "Purification and Characterization of Yeast Myristoyl-Coa—Protein N-Myristoyltransferase," P Natl Acad Sci USA, 1987, 84(9):2708-12.

Trabbic-Carlson et al., "Effect of protein fusion on the transition temperature of an environmentally responsive elastin-like polypeptide: a role for surface hydrophobicity?," Protein Engineering Design and Selection, 2004, 17(1): 57-66.

Trabbic-Carlson et al., "Expression and purification of recombinant proteins from Escherichia coli: Comparison of an elastin-like polypeptide fusion with an oligohistidine fusion" Protein Science, 2004, 13: 3274-3284.

Trakul et al., "Stereotactic body radiotherapy in the treatment of pancreatic cancer," Semin Radiat Oncol, Apr. 2014, 24(2): 140-147.

Trieu et al., "P0157 Preclinical evaluation of NBN-paclitaxel in pancreatic cancer xenograft models," Eur J Cancer, May 2014, 50(4): e53.

Triola et al., "Chemical biology of lipidated proteins," ACS Chemical Biology, Jan. 2012, 7(1): 87-99.

Troyanskaya et al., "Nonparametric methods for identifying differentially expressed genes in microarray data," Bioinformatics, 2002, 18(11):1454-61.

Truong et al., "Polymeric filomicelles and nanoworms: two decades of synthesis and application," Polymer Chemistry, Jun. 2016, 7(26):4295-4312.

Truong et al., "The Importance of Nanoparticle Shape in Cancer Drug Delivery," Expert Opin Drug Deliv, Jan. 2015, 12(1):129-42.

Truong, et al., "The effect of hydration on molecular chain mobility and the viscoelastic behavior of resilin-mimetic protein-based hydrogels," Biomaterials, Elsevier, Nov. 2011, 32(33):8462-73.

(56) References Cited

OTHER PUBLICATIONS

Tsarevsky et al., "Deactivation efficiency and degree of control over polymerization in ATRP in protic solvents," Macromolecules 37, 2004, 9768-9778.
Tschöp et al., "Unimolecular Polypharmacy for Treatment of Diabetes and Obesity," Cell Metab, Jul. 2016, 24(1):51-62.
Tsume et al., "The development of orally administrable gemcitabine prodrugs with D-enantiomer amino acids: Enhanced membrane permeability and enzymatic stability," Eur. J. Pharm. Biopharm., Apr. 2014, 86(3):514-523.
Tu et al., "Stages in tropoelastin coalescence during synthetic elastin hydrogel formation," Micron, Apr. 2010, 41(3): 268-272.
Turunen et al., "Paclitaxel Succinate Analogs: Anionic Introduction as a Strategy to Impart Blood Brain Barrier Permeability," Bioorg Med Chem Lett, Nov. 2008, 18(22):5971-5974.
Tward et al., "Survival of men with clinically localized prostate cancer treated with prostatectomy, brachytherapy, or no definitive treatment: impact of age at diagnosis," Cancer, Oct. 2006, 107(10): 2392-2400.
Uchida et al., "Potential of adenovirus-mediated REIC/Dkk-3 gene therapy for use in the treatment of pancreatic cancer," Journal of Gastroenterology and Hepatology, Apr. 2014, 29(5):973-983.
Urry et al., "Calculation of distorted circular dichroism curves for poly-L-glutamic acid suspensions," Arch Biochem Biophys, 1970, 137, 214-221.
Urry et al., "Coacervation of solubilized elastin effects a notable conformational change," Nature, 1969, 222, 795-796.
Urry et al., "Differential scatter of left and right circularly polarized light by optically active particulate systems," Proc Natl Acad Sci U S A, 1970, 65, 845-852.
Urry et al., "Distortions in circular dichroism patterns of particulate (or membranous) systems," Arch Biochem Biophys, 1968, 128, 802-807.
Urry et al., "Elastic protein-based polymers in soft tissue augmentation and generation," J. Biomater. Sci. Polym. Ed., 1998, 9, 1015-1048.
Urry et al., "Hydrophobicity Scale for Proteins Based on InverseTemperature Transitions," Biopolymers, 1992, 32:1243-1250.
Urry et al., "Physical chemistry of biological free energy transduction as demonstrated by elastic protein-based polymers," J. of Phys. Chem. B., 1997, 101, 11007-11028.
Urry et al., "Temperature dependence of length of elastin and its polypentapeptide," Biochem Biophys Res Commun, 1986, 141, 749-755.
Urry et al., "Temperature of polypeptide inverse temperature transition depends on mean residue hydrophobicity," J. Am. Chem. Soc., 1991, 113(11):4346-4348.
Urry, "Free energy transduction in polypeptides and proteins based on inverse temperature transitions," Prog Biophys Mol Biol, Jan. 1992, 57(1):23-57.
Urry, "Protein elasticity based on conformations of sequential polypeptides: The biological elastic fiber," J Protein Chemistry, 1984, 3, 403-436.
Uversky et al., "Intrinsically disordered proteins as crucial constituents of cellular aqueous two phase systems and coacervates," FEBS Lett, Jan. 2015, 589(1):15-22.
Uversky et al., "Understanding protein non-folding," Biochim Biophys Acta, Elsevier, Jun. 2010, 1804(6):1231-1264.
Valkenburg et al., "Targeting the tumour stroma to improve cancer therapy," Nature Reviews Clinical Oncology, Jun. 2018, 15, 366-381.
van der Lee et al., "Classification of intrinsically disordered regions and proteins," Chem Rev, Jul. 2014, 114(13): 6589-6631.
Van Roey et al., "Short linear motifs: ubiquitous and functionally diverse protein interaction modules directing cell regulation," Chem Rev, Jul. 2014, 114(13): 6733-6778.
Van Roy, "Beyond E-cadherin: roles of other cadherin superfamily members in cancer," Nat Rev Cancer, Feb. 2014, 14(2): 121-134.

Vasey et al., "Phase I clinical and Pharmacokinetic study of PK1 (N-(2- Hydroxypropyl)methacrylamide Copolymer Doxorubicin): First member of a New Class of Chemotherapeutic Agents-Drugs-Polymer Conjugates" Clinical Cancer Research, 1999, 5:83-94.
Vazquez-Lombardi et al., "Challenges and Opportunities for Non-Antibody Scaffold Drugs," Drug Discov Today, Oct. 2015, 20(10):1271-83.
Vega et al., "Targeting Doxorubicin to Epidermal Growth Factor Receptors by Site-Specific Conjugation of C225 to Poly(L-Glutamic Acid) through a Polyethylene Glycol Spacer," Pharmaceutical Research, 2003, 20(5):826-832.
Venkataraman et al., "The Effects of Polymeric Nanostructure Shape on Drug Delivery," Adv Drug Deliv Rev, Elsevier, Nov. 2011, 63(14-15):1228-46.
Verma et al., "Effect of surface properties on nanoparticle-cell interactions," Small, Wiley, Jan. 2010, 6(1):12-21.
Veronese et al., "PEGylation, successful approach to drug delivery," Drug Discovery Today, 2005, 10(21):1451-1458.
Veronese, "Peptide and protein PEGylation: a review of problems and solutions," Biomaterials 22, 2001, 405-417.
Vicini et al., "An interinstitutional and interspecialty comparison of treatment outcome data for patients with prostate carcinoma based on predefined prognostic categories and minimum follow-up," Cancer, 2002, 95, 2126-2135.
Viegas et al., "Polyoxazoline: Chemistry, properties and applications," Bioconjugate Chem., May 2011, 22(5): 976-986.
Vlieghe et al., "Synthetic therapeutic peptides: science and market," Drug Discovery Today, Jan. 2010, 15(1-2): 40-56.
Voelker et al., "Alteration of the specificity and regulation of fatty acid synthesis of *Escherichia coli* by expression of a plant medium-chain acyl-acyl carrier protein thioesterase," J Bacteriol., 1994, 176(23):7320-7.
Volkova et al., "Anthracycline Cardiotoxicity: Prevalence, Pathogenesis and Treatment," Curr. Cardiol. Rev., Nov. 2011, vol. 7, No. 4, pp. 214-220.
von Roemeling et al., "Breaking Down the Barriers to Precision Cancer Nanomedicine," Trends Biotechnol, Feb. 2017, 35(2):159-171.
Vonarbourg et al., "Evaluation of pegylated lipid nanocapsules versus complement system activation and macrophage uptake," J Biomed Mater Res A, Wiley, Sep. 2006, 78(3):620-8.
Vrhovski et al., "Biochemistry of tropoelastin," Eur J Biochem, 1998, 258, 1-18.
Vrhovski et al., "Coacervation Characteristics of Recombinant Human Tropoelastin," European Journal of Biochemistry, 1997, 250(1):92-98.
Vrignaud et al., "Strategies for the nanoencapsulation of hydrophilic molecules in polymer-based nanoparticles," Biomaterials, Nov. 2011, 32(33):8593-8604.
Walczak, "Death Receptor—Ligand Systems in Cancer, Cell Death, and Inflammation," Cold Spring Harb. Perspect. Biol., May 2013, 5(5): a008698.
Wali et al., "Measuring Death of Pancreatic Beta Cells in Response to Stress and Cytotoxic T Cells," Methods in Molecular Biology, Mar. 2015, 1292:165-176.
Walsh et al., "Post-translational modifications in the context of therapeutic proteins," Nat. Biotechnol., Oct. 2006, 24(10): 1241-1252.
Walsh et al., "Posttranslationale Proteinmodifikation: die Chemie der Proteomdiversifizierung," Angew Chem, 2005, 117, 7508-7539.
Walsh et al., "Protein posttranslational modifications: The chemistry of proteome diversifications," Angew. Chem. Int. Ed., 2005, 44, 7342-7372.
Wang et al., "A Molecular Grammar Governing the Driving Forces for Phase Separation of Prion-like RNA Binding Proteins," Cell, Jul. 2018, 174(3):688-699.e616.
Wang et al., "Enhanced Tumor Delivery of Gemcitabine via PEG-DSPE/TPGS Mixed Micelles," Mol. Pharm., Apr. 2014, 11(4): 1140-1150.
Wang et al., "Extending Half Life of H-Ferritin Nanoparticle by Fusing Albumin Binding Domain for Doxorubicin Encapsulation," Biomacromolecules, Mar. 2018, 19(3):773-781.

(56) References Cited

OTHER PUBLICATIONS

Wang et al., "More effective nanomedicines through particle design," Small, Wiley, Jul. 2011, 7(14):1919-31.
Wang et al., "Nanoparticle delivery of cancer drugs," Annu Rev Med, Annual Reviews, Feb. 2012, 63:185-98.
Wang et al., "Quantitative Mapping of the Spatial Distribution of Nanoparticles in Endo-Lysosomes by Local pH," Nano Lett., Feb. 2017, 17(2): 1226-1232.
Wang et al., "Size and dynamics of caveolae studied using nanoparticles in living endothelial cells," ACS nano, Dec. 2009, 3(12): p. 4110-4116.
Wang et al., "Stimuli-responsive Dendrimers in Drug Delivery," Biomater Sci, Mar. 2016, 4(3):375-90.
Wang et al., "The Weak Link: Optimization of the Ligand-Nanoparticle Interface to Enhance Cancer Cell Targeting by Polymer Micelles," Nano Lett Oct. 2017, 17(10):5995-6005.
Waterman et al., "Edema associated with I-125 or Pd-103 prostate brachytherapy and its impact on post-implant dosimetry: an analysis based on serial CT acquisition," International journal of radiation oncology, biology, physics, 1998, 41, 1069-1077.
Wechsel et al., "Renal Cell Carcinoma: Immunohistological Investigation of Expression of the Integrin $\alpha v \beta 3$," Anticancer research, 1999, 19(2C):1529-1532.
Wei et al., "Anticancer drug nanomicelles formed by self-assembling amphiphilic dendrimer to combat cancer drug resistance," Proceedings of the National Academy of Sciences of the United States of America, Mar. 2015, 112(10):2978-2983.
Wei et al., "Fibroblast growth factor 21 promotes bone loss by potentiating the effects of peroxisome proliferator-activated receptor $\gamma$," Proc Natl Acad Sci USA, Feb. 2012, 109(8):3143-3148.
Weis et al., "$\alpha V$ Integrins in Angiogenesis and Cancer," Cold Spring Harb Perspect Med, Cold Spring Harbor Laboratory Press, Sep. 2011, 1(1):a006478.
Weitzhandler et al., "Micellar Self-Assembly of Recombinant Resilin-/Elastin-Like Block Copolypeptides," Biomacromolecules, Aug. 2017, 18(8):2419-2426.
Wendt et al., "DNA-mediated Folding and Assembly of MyoD-E47 Heterodimers," Journal of Biol. Chem., 1998, 273(10):5735-5743.
Wente et al., "Fibroblast Growth Factor-21 Improves Pancreatic $\beta$-Cell Function and Survival by Activation of Extracellular Signal-Regulated Kinase 1/2 and Akt Signaling Pathways," Diabetes, Sep. 2006, 55(9):2470-2478.
Werle et al., "Strategies to improve plasma half life time of peptide and protein drugs," Amino Acids 30, Jun. 2006, 30(4):351-367.
Wienkers et al., "Predicting in vivo drug interactions from in vitro drug discovery data," Nat. Rev. Drug. Discov. 2005, 4(10):825-833.
Wilkins et al., "Hydrodynamic Radii of Native and Denatured Proteins Measured by Pulse Field Gradient NMR Techniques," Biochemistry, 1999, 38(50):16424-16431.
Williams et al., "Targeted radionuclide therapy," Medical Physics, Jul. 2008, 35(7): 3062-3068.
Williamson et al., "Efficient N-terminal labeling of proteins by use of sortase," Angew Chem Int ed Engl, Sep. 2012, 51(37):9377-9380.
Wimley et al., "Experimentally determined hydrophobicity scale for proteins at membrane interfaces," Nature Structural & Molecular Biology, 1996, 3(10):842-848.
Winzell et al., "The high-fat diet-fed mouse: a model for studying mechanisms and treatment of impaired glucose tolerance and type 2 diabetes," Diabetes 53, 2004, S215-S219.
Wold, "In vivo chemical modification of proteins," Annu. Rev. Med., 1981, 50, 783-814.
Wood et al., "Experiences Using Chloramine-T and 1,3,4,6-Tetrachloro-3-Alpha,6-Alpha-Diphenylglycoluril (Iodogen) for Radioiodination of Materials for Radioimmunoassay," J Clin Chem Clin Bio, 1981, 19, 1051-1056.
Wright et al., "Intrinsically disordered proteins in cellular signalling and regulation," Nat Rev Mol Cell Biol, Jan. 2015, 16(1):18-29.

Wright et al., "Self-assembly of block copolymers derived from elastin-mimetic polypeptide sequences," Advanced Drug Delivery Reviews, 2002, 54, 1057-1073.
Wright et al., "Thermoplastic elastomer hydrogels via self-assembly of an elastin-mimetic triblock polypeptide," Advanced Functional Materials, 2002, 12, 149-154.
Wu et al., "Site-specific chemical modification of recombinant proteins produced in mammalian cells by using the genetically encoded aldehyde tag," Proc Natl Acad Sci USA, Mar. 2009, 106(9):3000-3005.
Wu et al., "Sortase A-Catalyzed Transpeptidation of Glycosylphosphatidylinositol Derivatives for Chemoenzymatic Synthesis of GPI-Anchored Proteins," J. Am. Chem. Soc., Feb. 2010, 132(5): 1567-1571.
Wust et al., "Hyperthermia in combined treatment of cancer," The Lancet Oncology, 2002, 3, 487-497.
Xavier et al., "HPLC Method for the Dosage of Paclitaxel in Copaiba Oil: Development, Validation, Application to the Determination of the Solubility and Partition Coefficients," Chromatographia, Apr. 2016, 79(7-8): 405-412.
Xia et al., "Tunable self-assembly of genetically engineered silk—elastin-like protein polymers," Biomacromolecules, Nov. 2011, 12(11): 3844-3850.
Xie et al., "The Effect of Shape on Cellular Uptake of Gold Nanoparticles in the Forms of Stars, Rods, and Triangles," Sci Rep, Jun. 2017, 7(1):3827.
Xiong et al., "Engineering of amphiphilic block copolymers for polymeric micellar drug and gene delivery," J Control Release, Elsevier, Oct. 2011, 155(2):248-61.
Xu et al., "A quality by design (QbD) case study on liposomes containing hydrophilic Api: II. Screening of critical variables, and establishment of design space at laboratory scale," Int. J. Pharm., Feb. 2012, 423(2):543-553.
Xu et al., "Downregulation of GLP-1 and GIP Receptor Expression by Hyperglycemia," Diabetes, Jun. 2007, 56(6):1551-58.
Xu et al., "Exendin-4 stimulates both beta-cell replication and neogenesis, resulting in increased beta-cell mass and improved glucose tolerance in diabetic rats," Diabetes 48, 1999, 2270-2276.
Xu et al., "Fibroblast Growth Factor 21 Reverses Hepatic Steatosis, Increases Energy Expenditure, and Improves Insulin Sensitivity in Diet-Induced Obese Mice," Diabetes, Jan. 2009, 58(1):250-259.
Xu et al., "Genetically engineered block copolymers: influence of the length and structure of the coiled-coil blocks on hydrogel self-assembly," Pharm Res, Mar. 2008, 25, 674-682.
Xu et al., "Inorganic nanoparticles as carriers for efficient cellular delivery," Chemical Engineering Science, Elsevier, Feb. 2006, 61(3):1027-1040.
Xu et al., "Role of pancreatic stellate cells in pancreatic cancer metastasis," Am J of Pathology, Nov. 2010, 177(5): 2585-2596.
Xu et al., "Self-assembly behavior of peptide amphiphiles (PAs) with different length of hydrophobic alkyl tails," Colloids Surfaces B Biointerfaces, Nov. 2010, 81(1): 329-335.
Yamamoto et al., "ATRP Synthesis of Thermally Responsive Molecular Brushes from Oligo(ethylene oxide) Methacrylates," Macromolecules, Dec. 2007, 40(26): 9348-9353.
Yang et al., "Long Term Exendin-4 Treatment Reduces Food Intake and Body Weight and Alters Expression of Brain Homeostatic and Reward Markers," Endocrinology, Sep. 2014, 155(9): 3473-3483.
Yang et al., "Poly(carboxybetaine) nanomaterials enable long circulation and prevent polymer-specific antibody production," Nano Today, Feb. 2014, 9(1):10-16.
Yates et al., "Contemporary management of patients with high-risk non-muscle-invasive bladder cancer who fail intravesical BCG therapy," World journal of urology, May 2011, 29(4): 415-422.
Yeo et al., "Coacervation of tropoelastin," Adv Colloid Interface Sci, Sep. 2011, 167(1-2):94-103.
Yokoe et al., "Albumin-conjugated PEG liposome enhances tumor distribution of liposomal doxorubicin in rats," International Journal of Pharmaceutics, May 2008, 353(1-2): 28-34.
Yoo et al., "A systemic Small RNA Signaling System in Plants" The Plant Cell (2004) vol. 16, pp. 1979-2000.

(56) References Cited

OTHER PUBLICATIONS

Yoo et al., "Biodegradable Nanoparticles Containing Doxorubicin-Plga Conjugate for Sustained Release," Pharm. Res., 1999, 16(7):1114-1118.
Youn et al., "Evaluation of therapeutic potentials of site-specific PEGylated glucagon-like peptide-1 isomers as a type 2 anti-diabetic treatment: Insulinotropic activity, glucose-stabilizing capability, and proteolytic stability" Biochem. Pharmacol, 2007, 73: 84-93.
Youn et al., "High-yield production of biologically active mono-PEGylated salmon calcitonin by site-specific PEGylation," J. Control. Release, Feb. 2007, 117(3):371-379.
Yousefpour et al., "Co-opting biology to deliver drugs," Biotechnol Bioeng, Sep. 2014, 111(9): p. 1699-1716.
Yousefpour et al., "Genetically Encoding Albumin Binding into Chemotherapeutic-loaded Polypeptide Nanoparticles Enhances Their Antitumor Efficacy," Nano Lett., Dec. 2018, 18(12): 7784-7793.
Yu et al., "Effectiveness and security of CT-guided percutaneous implantation of (125)l seeds in pancreatic carcinoma," The British journal of radiology, Jul. 2014, 87(1039): 20130642, 7 pages.
Yusta et al., "GLP-1 receptor activation improves β cell function and survival following induction of endoplasmic reticulum stress," Cell Metab, Nov. 2006, 4(5):391-406.
Zhang et al., "A self-assembly pathway to aligned monodomain gels," Nat. Mater., Jul. 2010, 9(7): 594-601.
Zhang et al., "In Depth Analysis on the Unusual Multistep Aggregation Process of Oligo(ethylene glycol) Methacrylate-Based Polymers in Water," Macromolecules, Jul. 2014, 47(14): 4728-4737.
Zhang et al., "Nanoparticles in medicine: therapeutic applications and developments," Clin. Pharmacol. Ther., May 2008, 83(5): 761-769.
Zhang et al., "Novel agents for pancreatic ductal adenocarcinoma: emerging therapeutics and future directions," Jounral of Hematology & Oncology, Jan. 2018, 11:14, 17 pages.
Zhang et al., "Shape Effects of Nanoparticles Conjugated with Cell-Penetrating Peptides (HIV Tat PTD) on CHO Cell Uptake," Bioconjugate Chem, Sep. 2008, 19(9):1880-1887.
Zhao et al., "A new Bliss Independence model to analyze drug combination data," J Biomol Screen, Jun. 2014, 19(5): 817-821.
Zhao et al., "Cellular uptake, intracellular trafficking, and cytotoxicity of nanomaterials," Small, Wiley, May 2011, 7(10):1322-37.
Zhao et al., "Fluorescence probe techniques used to study micelle formation in water-soluble block copolymers," Langmuir 1990, 6(2):514-516.
Zhao et al., "Tumor αvβ3 Integrin Is a Therapeutic Target for Breast Cancer Bone Metastases," Cancer Res, AACR Publications, Jun. 2007, 67(12):5821-30.
Zimm, "Apparatus and Methods for Measurement and Interpretation of the Angular Variation of Light Scattering; Preliminary Results on Polystyrene Solutions," J. Chem. Phys. 1948, 16, 1099-1116.
Zini et al., "Contemporary management of adrenocortical carcinoma," European urology, Nov. 2011, 60(5): 1055-1065.
Zong et al., "Crystal structures of *Staphylococcus aureus* sortase A and its substrate complex," J. Biol. Chem. 279, 2004, 31383-31389.
Zununi Vahed et al., "Targeted cancer drug delivery with aptamer-functionalized polymeric nanoparticles," Journal of drug targeting, Mar. 2019, 27(3):292-299.
International Search Report and Written Opinion for Application No. PCT/US2008/084159 dated Feb. 27, 2009 (8 pages).
International Search Report and Written Opinion for Application No. PCT/US2016/024202 dated Aug. 26, 2016 (9 pages).
International Search Report and Written Opinion for Application No. PCT/US2016/045655 dated Dec. 2, 2016 (13 pages).
International Search Report and Written Opinion for Application No. PCT/US2016/068141 dated Jul. 19, 2017 (12 pages).
International Search Report and Written Opinion for Application No. PCT/US2016/068142 dated Jul. 19, 2017 (12 pages).
International Search Report and Written Opinion for Application No. PCT/US2018/032785 dated Sep. 25, 2018 (16 pages).
International Search Report and Written Opinion for Application No. PCT/US2017/035530 dated Aug. 23, 2017 (13 pages).
International Search Report and Written Opinion for Application No. PCT/US2017/052887 dated Jan. 26, 2018 (20 pages).
International Search Report and Written Opinion for Application No. PCT/US2017/051661 dated Jan. 2, 2018 (12 pages).
International Search Report and Written Opinion for Application No. PCT/US2018/013611 dated May 30, 2018 (18 pages).
International Search Report and Written Opinion for Application No. PCT/US2018/040409 dated Nov. 5, 2018 (16 pages).
International Search Report and Written Opinion for Application No. PCT/US2019/015176 dated Jun. 3, 2019 (12 pages).
International Search Report and Written Opinion for Application No. PCT/US2019/023583 dated Jul. 5, 2019 (10 pages).
International Search Report and Written Opinion for Application No. PCT/US2019/030022 dated Jul. 25, 2019 (8 pages).
International Search Report and Written Opinion for Application No. PCT/US2019/044911 dated Dec. 10, 2019 (11 pages).
International Search Report and Written Opinion for Application No. PCT/US2019/050077 dated Jan. 27, 2020 (19 pages).
International Search Report and Written Opinion for Application No. PCT/US2019/061144 dated May 21, 2020 (15 pages).
United States Patent Office Action for U.S. Appl. No. 13/904,836 dated Mar. 27, 2014 (10 pages).
United States Patent Office Notice of Allowance for U.S. Appl. No. 13/904,836 dated Jul. 30, 2014 (6 pages).
United States Patent Office Action for U.S. Appl. No. 13/942,037 dated Jan. 15, 2016 (19 pages).
United States Patent Office Action for U.S. Appl. No. 13/942,037 dated Jun. 4, 2015 (33 pages).
United States Patent Office Action for U.S. Appl. No. 13/942,037 dated Nov. 28, 2016 (22 pages).
United States Patent Office Action for U.S. Appl. No. 13/942,037 dated Feb. 9, 2018 (29 pages).
United States Patent Office Notice of Allowance for U.S. Appl. No. 13/245,459 dated Feb. 27, 2013 (13 pages).
United States Patent Office Action for U.S. Appl. No. 14/572,391 dated Oct. 26, 2016 (11 pages).
United States Patent Office Notice of Allowance for U.S. Appl. No. 14/572,391 dated Jun. 16, 2017 (10 pages).
United States Patent Office Action for U.S. Appl. No. 15/387,536 dated Sep. 27, 2018 (11 pages).
United States Patent Office Action for U.S. Appl. No. 15/387,540 dated Sep. 27, 2018 (12 pages).
United States Patent Office Action for U.S. Appl. No. 15/561,799 dated Dec. 27, 2018 (8 pages).
United States Patent Office Notice of Allowance for U.S. Appl. No. 15/387,536 dated Mar. 13, 2019 (13 pages).
United States Patent Office Notice of Allowance for U.S. Appl. No. 15/561,799 dated Apr. 2, 2019 (6 pages).
United States Patent Office Notice of Allowance for U.S. Appl. No. 15/387,540 dated Apr. 17, 2019 (9 pages).
United States Patent Office Action for U.S. Appl. No. 16/058,924 dated Nov. 26, 2019 (23 pages).
United States Patent Office Action for U.S. Appl. No. 16/064,424 dated Apr. 22, 2020 (18 pages).
United States Patent Office Action for U.S. Appl. No. 16/064,425 dated Apr. 22, 2020 (18 pages).
United States Patent Office Action for U.S. Appl. No. 16/058,924 dated Jul. 6, 2020 (51 pages).
United States Patent Office Action for U.S. Appl. No. 15/749,797 dated May 11, 2020 (14 pages).
Alghoul et al., "The effect of hyaluronan hydrogel on fat graft survival," Aesthet Surg J, 2012, 32: 622-633.
American Society of Plastic Surgeons, "2017 Plastic Surgery Statistics Report," Oct. 2018, 25 pages.
Balaji, "Subdermal fat grafting for Parry-Romberg syndrome," Ann Maxillofac Surg, 2014, 4: 55-59.
Banyard et al., "Preparation, Characterization, and Clinical Implications of Human Decellularized Adipose Tissue Extracellular Matrix (hDAM): A Comprehensive Review," Aesthet Surg J, 2016, 36: 349-357.

(56) References Cited

OTHER PUBLICATIONS

Bennett et al., "Association of Fat Grafting With Patient-Reported Outcomes in Postmastectomy Breast Reconstruction," JAMA Surg, 2017, 152: 944-950.
Brzezienski et al., "Autologous Fat Grafting to the Breast Using Revolve System to Reduce Clinical Costs," Ann Plast Surg, 2016, 77: 286-289.
Chang et al., "Thermoprecipitation of Glutathione S-Transferase by Glutathione-Poly(N-isopropylacrylamide) Prepared by RAFT Polymerization," Macromolecular Rapid Communications, Oct. 2010, 31: 1691-1695.
De Leon-Rodriguez et al., "Multifunctional thermoresponsive designer peptide hydrogels," Acta Biomaterialia, 2017, 47: 40-49.
Eom et al., "The number of operations required for completing breast reconstruction," Plast Reconstr Surg Glob Open, 2012, 2: e242.
Frandsen et al., "Recombinant protein-based polymers for advanced drug delivery," Chem Soc Rev, 2012, 41: 2696-2706.
Gabriel et al., "Fat grafting and breast reconstruction: tips for ensuring predictability," Gland Surg, 2015, 4: 232-243.
Gylbert, "Applanation tonometry for the evaluation of breast compressibility," Scand J Plast Reconstr Surg Hand Surg, 1989, 23: 223-229.
Hess et al., "Graphene Transistors for Multifunctional Polymer Brushes for Biosensing Applications," Applied Materials & Interfaces, 2014, 6: 9705-9710.
Hsu et al., "Fat grafting's past, present, and future: why adipose tissue is emerging as a critical link to the advancement of regenerative medicine," Aesthet Surg J, 2015, 32: 892-899.
Hwang et al., "Synthesis and Characterization of Polystyrene Brushes for Organic Thin Film Transistors," Journal of Nanoscience and Nanotechnology, 2012, 12: 4137-4141.
Kronowitz et al., "Delayed-Immediate Breast Reconstruction," Plastic and Reconstructive Surgery, 2004, 113: 1617-1628.
Minteer et al., "Fat Grafting for Pedal Fat Pad Atrophy in a 2-Year, Prospective, Randomized, Crossover, Single-Center Clinical Trial," Plast Reconstr Surg, 2018, 142: 862e-871e.
Pan et al., "A Pig Model for the Histological Analysis of Adipocytes after Co-injections of Autologous Fat with Fillers," International Journal of Surgery & Surgical Techniques, 2016, 2: 7 pages.
Park et al., "Polymer Brush as a Facile Dielectric Surface Treatment for High-Performance, Stable, Soluble Acene-Based Transistors," Chemistry of Materials, 2010, 22: 5377-5382.
Rasmussen et al., "A Novel Porcine Model for Future Studies of Cell-enriched Fat Grafting," Plast Reconstr Surg Glob Open, 2018, 6: e1735.
Roca et al., "Autologous Fat Grafting for Treatment of Breast Implant Capsular Contracture: A Study in Pigs," Aesthet Surg J, 2014, 34: 769-775.
Sandberg et al., "The Structure of the Elastic Fiber: An Overview," The Journal of Investigative Dermatology, 1982, 79(S1): 128s-132s.
Simonacci et al., "Procedure, applications, and outcomes of autologous fat grafting," Ann Med Surg (Lond), 2017, 20: 49-60.
Strong et al., "The Current State of Fat Grafting: A Review of Harvesting, Processing, and Injection Techniques," Plast Reconstr Surg, 2015, 136: 897-912.
Tamburro et al., "Fractal aspects of elastin supramolecular organization," J Biomol Struct Dyn, 1995, 12: 1161-1172.
Toshima et al., "Three-dimensional architecture of elastin and collagen fiber networks in the human and rat lung," Arch Histol Cytol, 2004, 67: 31-40.
UniProtKB-P15214 (GST_PROM1) acessed online at <https://www.uniprot.org/uniprot/P152146/> on Jun. 8, 2021, 7 pages.
Wang et al., "Pigs Can Be Used as a Large Animal Model for Autologous Fat Grafting," Ophthalmic Plast Reconstr Surg, 2016, 32: 73-74.
Wu et al., "An injectable adipose matrix for soft-tissue reconstruction," Plast Reconstr Surg, 2012, 129: 1247-1257.
United States Patent Office Action for U.S. Appl. No. 15/749,797 dated May 12, 2021 (19 pages).
United States Patent Office Notice of Allowance for U.S. Appl. No. 16/332,865 dated May 17, 2021 (5 pages).
United States Patent Office Notice of Allowance for U.S. Appl. No. 16/335,734 dated Jun. 16, 2021 (9 pages).
United States Patent Office Action for U.S. Appl. No. 16/305,696 dated Jun. 22, 2021 (20 pages).
Zhang et al., "Sensitive and Quantitative Detection of Anti-Poly(ethylene glycol) (PEG) Antibodies by Methoxy-PEG-Coated Surface Plasmon Resonance Sensors," Anal Chem, Aug. 2017, 89(16): 8217-8222.
United States Patent Office Action for U.S. Appl. No. 15/749,797 dated Oct. 20, 2020 (16 pages).
Abbaspourrad et al., "Controlling release from pH-responsive microcapsules," Langmuir, 2013, 29: 12697-12702.
Abbaspourrad et al., "Polymer microcapsules with programmable active release," J Am Chem Soc, 2013, 135: 7744-7750.
Agarwal et al., "One-step microfluidic generation of pre-hatching embryo-like core-shell microcapsules for miniaturized 3D culture of pluripotent stem cells," Lab Chip, 2013, 13: 4525-4533.
Amiram et al., "Evolution of translation machinery in recoded bacteria enables multi-site incorporation of nonstandard amino acids," Nat Biotechnol, 2015, 33: 1272-1279.
Appleyard et al., "Multiplexed protein quantification with barcoded hydrogel microparticles," Anal Chem, 2011, 83: 193-199.
Bain et al., "Formation of monolayer films by the spontaneous assembly of organic thiols from solution onto gold," Journal of the American Chemical Society, 1989, 111: 321-335.
Boeynaems et al., "Spontaneous driving forces give rise to protein-RNA condensates with coexisting phases and complex material properties," Proc Natl Acad Sci U S A, 2019, 116: 7889-7898.
Cha et al., "Microfluidics-assisted fabrication of gelatin-silica core-shell microgels for injectable tissue constructs," Biomacromolecules, 2014, 15: 283-290.
Chapin et al., "Rapid microRNA profiling on encoded gel microparticles," Angew Chem Int Ed Engl, 2011, 50: 2289-2293.
Chin et al., "Addition of p-azido-l-phenylalanine to the genetic code of *Escherichia coli*," Journal of the American Chemical Society, 2002, 124: 9026-9027.
Choi et al., "Multiplexed detection of mRNA using porosity-tuned hydrogel microparticles," Anal Chem, 2012, 84: 9370-9378.
Choi et al., "Recent advances in engineering microparticles and their nascent utilization in biomedical delivery and diagnostic applications," Lab Chip, 2017, 17: 591-613.
Chu et al., "Controllable monodisperse multiple emulsions," Angew Chem Int Ed Engl, 2007, 46: 8970-8974.
Costa et al., "Photo-crosslinkable unnatural amino acids enable facile synthesis of thermoresponsive nano- to microgels of intrinsically disordered polypeptides," Adv Mater, 2018, 30(5): 1704878.
Darling et al., "Viscoelastic properties of zonal articular chondrocytes measured by atomic force microscopy," Osteoarthritis Cartilage, 2006, 14: 571-579.
Griffin et al., "Accelerated wound healing by injectable microporous gel scaffolds assembled from annealed building blocks," Nat Mater, 2015, 14: 737-744.
Hutter et al., "Calibration of atomic-force microscope tips," Review of Scientific Instruments, 1993, 64: 1868-1873.
Hwang et al., "Differentially degradable janus particles for controlled release applications," Macromol Rapid Commun, 2012, 33: 1178-1183.
Jang et al., "Engineering Globular Protein Vesicles through Tunable Self-Assembly of Recombinant Fusion Proteins," Small, 2017, 13(36): 1700399.
Khademhosseini et al., "Micromolding of photocrosslinkable hyaluronic acid for cell encapsulation and entrapment," J Biomed Mater Res A, 2006, 79: 522-532.
Kim et al., "Generation of core-shell microcapsules with three-dimensional focusing device for efficient formation of cell spheroid," Lab Chip, 2011, 11: 246-252.
Liu, L et al., "Monodisperse core-shell chitosan microcapsules for pH-responsive burst release of hydrophobic drugs," Soft Matter, 2011, 7: 4821-4827.
Ma et al., "Core-shell hydrogel microcapsules for improved islets encapsulation," Adv Healthc Mater, 2013, 2: 667-672.

(56) References Cited

OTHER PUBLICATIONS

Matsunaga et al., "Molding cell beads for rapid construction of macroscopic 3D tissue architecture," Adv Mater, 2011, 23: H90-94.
Oh et al., "The development of microgels/nanogels for drug delivery applications," Progress in Polymer Science, 2008, 33(4): 448-477.
Panda et al., "Stop-flow lithography to generate cell-laden microgel particles," Lab Chip, 2008, 8: 1056-1061.
Paulsen et al., "Optofluidic fabrication for 3D-shaped particles," Nat Commun, 2015, 6: 6976.
Roberts et al., "Injectable tissue integrating networks from recombinant polypeptides with tunable order," Nature Materials, 2018, 17(12): 1154-1163.
Rodriguez-Cabello et al., "Elastin-like polypeptides in drug delivery," Adv Drug Deliv Rev, 2016, 97: 85-100.
Song et al., "Budding-like division of all-aqueous emulsion droplets modulated by networks of protein nanofibrils," Nat Commun, 2018, 9: 2110.
Srinivas et al., "Aptamer-functionalized microgel particles for protein detection," Anal Chem, 2011, 83: 9138-9145.
Tsuda et al., "Monodisperse cell-encapsulating peptide microgel beads for 3D cell culture," Langmuir, 2010, 26: 2645-2649.
Utada et al., "Monodisperse double emulsions generated from a microcapillary device," Science, 2005, 308: 537-541.
Uversky, "Protein intrinsic disorder-based liquid-liquid phase transitions in biological systems: Complex coacervates and membrane-less organelles," Adv Colloid Interface Sci, 2017, 239: 97-114.
Volodkin et al., "One-Step Formulation of Protein Microparticles with Tailored Properties: Hard Templating at Soft Conditions," Advanced Functional Materials, 2012, 22: 1914-1922.
Wang et al., "Functional polymeric microparticles engineered from controllable microfluidic emulsions," Acc Chem Res, 2014, 47: 373-384.
Yeh et al., "Micromolding of shape-controlled, harvestable cell-laden hydrogels," Biomaterials, 2006, 27: 5391-5398.
United States Patent Office Action for U.S. Appl. No. 16/305,696 dated Jan. 28, 2021 (15 pages).
United States Patent Office Notice of Allowance for U.S. Appl. No. 16/332,865 dated Apr. 2, 2021 (10 pages).
Resh, "Covalent Lipid Modifications of Proteins," Curr Biol., May 2013, 23(10): R431-R435.
United States Patent Office Action for U.S. Appl. No. 16/477,229 dated Apr. 12, 2021 (14 pages).
United States Patent Office Action for U.S. Appl. No. 16/335,734 dated Nov. 20, 2020 (15 pages).
United States Patent Office Action for U.S. Appl. No. 16/525,374 dated Dec. 7, 2020 (9 pages).
U.S. Appl. No. 13/245,459, filed Sep. 26, 2011, U.S. Pat. No. 8,470,967, Jun. 25, 2013.
U.S. Appl. No. 13/904,836, filed May 29, 2013, U.S. Pat. No. 8,912,310, Dec. 16, 2014.
U.S. Appl. No. 14/572,391, filed Dec. 16, 2014, U.S. Pat. No. 9,771,396, Jun. 25, 2013.
U.S. Appl. No. 15/679,751, filed Aug. 17, 2017, 2018/0037609, Feb. 8, 2018.
U.S. Appl. No. 62/138,847, filed Mar. 26, 2015.
PCT/US2016/024202, Mar. 25, 2016, WO2016/154530, Sep. 26, 2016.
U.S. Appl. No. 15/561,799, filed Sep. 26, 2017, U.S. Pat. No. 10,385,115, Aug. 20, 2019.
U.S. Appl. No. 16/525,374, filed Jul. 29, 2019, 2019/0345228, Nov. 14, 2019.
U.S. Appl. No. 62/399,123, filed Sep. 23, 2016.
PCT/US2017/052887, Sep. 22, 2017, WO2018/057847, Mar. 29, 2018.
U.S. Appl. No. 16/335,734, filed Mar. 22, 2019, 2020/0017557, Jan. 16, 2020.
U.S. Appl. No. 13/942,037, filed Jul. 15, 2015, 2014/0024600, Jan. 23, 2014.
U.S. Appl. No. 16/058,924, filed Aug. 8, 2018, 2019/0023743, Jan. 24, 2019.
U.S. Appl. No. 62/270,401, filed Dec. 21, 2015.
U.S. Appl. No. 62/310,534, filed Mar. 18, 2016.
U.S. Appl. No. 62/329,800, filed Apr. 29, 2016.
U.S. Appl. No. 62/407,403, filed Oct. 12, 2016.
PCT/US2016/068141, Dec. 21, 2016, WO2017/112825, Jun. 29, 2017.
PCT/US2016/068142, Dec. 21, 2016, WO2017/112826, Jun. 29, 2017.
U.S. Appl. No. 15/387,536, filed Dec. 21, 2016, U.S. Pat. No. 10,365,451, Jul. 30, 2019.
U.S. Appl. No. 15/387,540, filed Dec. 21, 2016, U.S. Pat. No. 10,392,611, Aug. 27, 2019.
U.S. Appl. No. 16/064,424, filed Jun. 20, 2018, 2019/0015520, Jan. 17, 2019.
U.S. Appl. No. 16/064,425, filed Sep. 12, 2016, 2018/0369399, Dec. 27, 2018.
U.S. Appl. No. 62/506,593, filed May 15, 2017.
U.S. Appl. No. 62/534,442, filed Jul. 19, 2017.
U.S. Appl. No. 62/544,720, filed Aug. 11, 2017.
U.S. Appl. No. 62/545,313, filed Aug. 14, 2017.
PCT/US20168/032785, May 15, 2018, WO2018/213320, Nov. 22, 2018.
U.S. Appl. No. 16/614,282, filed Nov. 15, 2019.
U.S. Appl. No. 62/200,726, filed Aug. 4, 2015.
PCT/US2016/045655, Aug. 4, 2016, WO2017/024182, Feb. 9, 2017.
U.S. Appl. No. 15/749,797, filed Feb. 2, 2018, 2018/0228908, Aug. 16, 2018.
U.S. Appl. No. 62/394,662, filed Sep. 14, 2016.
PCT/US2017/051661, Sep. 14, 2017, WO2018/053201, Mar. 22, 2018.
U.S. Appl. No. 16/332,865, filed Mar. 13, 2019, 2020/164082, May 28, 2020.
U.S. Appl. No. 62/445,504, filed Jan. 12, 2017.
U.S. Appl. No. 62/479,977, filed Mar. 31, 2017.
PCT/US2018/013611, Jan. 12, 2018, WO2018/132732, Jul. 19, 2018.
U.S. Appl. No. 16/477,229, filed Jul. 11, 2019, 2019/0328662, Oct. 31, 2019.
U.S. Appl. No. 62/527,836, filed Jun. 30, 2017.
U.S. Appl. No. 62/534,019, filed Jul. 18, 2017.
PCT/US2018/040409, Jun. 29, 2018, WO2019/006374, Jan. 3, 2019.
U.S. Appl. No. 16/625,899, filed Dec. 23, 2019, 2020/0148724, May 14, 2020.
U.S. Appl. No. 62/343,926, filed Jun. 1, 2016.
U.S. Appl. No. 62/414,877, filed Oct. 31, 2016.
PCT/US2017/035530, Jun. 1, 2017, WO2017/210476, Dec. 7, 2018.
U.S. Appl. No. 16/305,696, filed Nov. 29, 2018.
U.S. Appl. No. 62/728,582, filed Sep. 7, 2018.
PCT/US2019/050077, Sep. 6, 2019, WO2020/051541, Mar. 12, 2020.
U.S. Appl. No. 62/767,736, filed Nov. 15, 2018.
PCT/US2019/061144, Nov. 13, 2019, WO2020/102324, May 22, 2020.
U.S. Appl. No. 62/647,199, filed Mar. 23, 2018.
PCT/US2019/023583, Mar. 22, 2019, WO2019/183476, Sep. 26, 2019.
U.S. Appl. No. 62/664,512, filed Apr. 30, 2018.
PCT/US2019/030022, Apr. 30, 2019, WO2019/213150, Nov. 7, 2019.
U.S. Appl. No. 62/700,939, filed Jul. 20, 2018.
U.S. Appl. No. 62/873,306, filed Jul. 12, 2019.
U.S. Appl. No. 16/927,982, filed Jul. 13, 2020.
U.S. Appl. No. 62/713,752, filed Aug. 2, 2018.
PCT/US2019/044911, Aug. 2, 2019, WO2020/028806, Feb. 6, 2020.
U.S. Appl. No. 62/985,174, filed Mar. 4, 2020.
U.S. Appl. No. 62/985,179, filed Mar. 4, 2020.
U.S. Appl. No. 62/898,353, filed Sep. 12, 2019.
U.S. Appl. No. 17/015,315, filed Sep. 9, 2020.

(56) References Cited

OTHER PUBLICATIONS

Nikolic et al., "Structural basis for the recognition of LDL-receptor family members by VSV glycoprotein," Nature Communications, 2018, 9: 1029, 12 pages.
International Search Report and Written Opinion for Application No. PCT/US2021/020589 dated Jul. 15, 2021 (21 pages).
International Search Report and Written Opinion for Application No. PCT/US2021/017809 dated Jul. 22, 2021 (20 pages).
Ahmed et al., "Preliminary Identification of Potential Vaccine Targets for the COVID-19 Coronavirus (SARS-CoV-2) Based on SARS-CoV Immunological Studies," Viruses, 2020, 12:254, 15 pages.
Amanat et al., "A serological assay to detect SARS-CoV-2 seroconversion in humans," Nat Med, 2020, 26(7): 1033-1036.
American Hospital Association, "AHA Hospital Statistics," 2020 edition. Available at: <https://www.aha.org/statistics/fast-facts-us-hospitals>.
Armbruster et al., "Limit of blank, limit of detection and limit of quantitation," Clin Biochem Rev, 2008, 29 Suppl 1: S49-52.
Arshavsky-Graham et al., "Lab-on-a-Chip Devices for Point-of-Care Medical Diagnostics," Advances in Biochemical Engineering/Biotechnology, 2020, 19 pages.
Atyeo et al., "Distinct Early Serological Signatures Track with SARS-CoV-2 Survival," Immunity, 2020, 53: 524-532.
Baraf et al., "Infusion-related reactions with pegloticase, a recombinant uricase for the treatment of chronic gout refractory to conventional therapy," J Clin Rheumatol, 2014, 20: 427-432.
Benn et al., "Physiology of Hyperuricemia and Urate-Lowering Treatments," Front Med (Lausanne), 2018, 5: 160, 28 pages.
Berry et al., "Development and characterisation of neutralising monoclonal antibody to the SARS-coronavirus," J Virol Methods, 2004, 120: 87-96.
Bryant et al., "Serology for SARS-CoV-2: Apprehensions, opportunities, and the path forward," Sci Immunol, 2020, 5: eabc6347, 4 pages.
Calabrese et al., "Frequency, distribution and immunologic nature of infusion reactions in subjects receiving pegloticase for chronic refractory gout," Arthritis Res Ther, 2017, 19: 191, 7 pages.
Caves et al., "Thermal inactivation of uricase (urate oxidase): mechanism and effects of additives," Biochemistry, 2013, 52: 497-507.
Chae et al., "Pharmacokinetic and pharmacodynamic evaluation of site-specific PEGylated glucagon-like peptide-1 analogs as flexible postprandial-glucose controllers," J Pharm Sci, 2009, 98(4): 1556-1567.
Chen et al., "Real-world patterns of pegloticase use for treatment of gout: descriptive multidatabase cohort study," BMJ Open, 2020, 10: e041167, 6 pages.
Chen et al., "The influence of polymer topology on pharmacokinetics: differences between cyclic and linear PEGylated poly(acrylic acid) comb polymers," J Control Release, 2009, 140: 203-209.
Chu et al., "Molecular Diagnosis of a Novel Coronavirus (2019-nCoV) Causing an Outbreak of Pneumonia," Clin Chem, 2020, 66(4): 549-555.
Cong et al., "Nucleocapsid Protein Recruitment to Replication-Transcription Complexes Plays a Crucial Role in Coronaviral Life Cycle," J Virol, 2020, 94: e01925-19, 21 pages.
Crowther, "The ELISA guidebook," Methods Mol Biol, 2000, 149(III-IV): 1-413.
Dincer et al., "Multiplexed Point-of-Care Testing—xPOCT," Trends Biotechnol, 2017, 35(8): 728-742.
Dong et al., "An interactive web-based dashboard to track COVID-19 in real time," Lancet Infect Dis, 2020, 20: 533-534.
Dutta et al., "The Nucleocapsid Protein of SARS-CoV-2: a Target for Vaccine Development," J Virol, 2020, 94(13): e00647-20, 2 pages.
Ekladious et al., "Polymer-drug conjugate therapeutics: advances, insights and prospects," Nature Reviews Drug Discovery, 2019, 18: 273-294.

Fathallah et al., "Immunogenicity of Subcutaneously Administered Therapeutic Proteins—a Mechanistic Perspective," The AAPS Journal, 2013, 15(4): 897-900.
Fox et al., "Soluble polymer carriers for the treatment of cancer: the importance of molecular architecture," Acc Chem Res, 2009, 42(8): 1141-1151.
Garay et al., "Therapeutic perspectives on uricases for gout," Joint Bone Spine, 2012, 79: 237-242.
Harris et al., "Effect of pegylation on pharmaceuticals," Nature Reviews Drug Discovery, 2003, 2: 214-221.
Heggestad et al., "In Pursuit of Zero 2.0: Recent Developments in Nonfouling Polymer Brushes for Immunoassays," Adv Mater, 2020, 32: e1903285.
Hermanson et al., "Peginesatide for the treatment of anemia due to chronic kidney disease—an unfulfilled promise," Expert Opin Drug Saf, 2016, 15(10): 1421-1426.
Hershfield et al., "Treating gout with pegloticase, a PEGylated urate oxidase, provides insight into the importance of uric acid as an antioxidant in vivo," Proc Natl Acad Sci U S A, 2010, 107(32): 14351-14356.
Huang et al., "Clinical features of patients infected with 2019 novel coronavirus in Wuhan," China. Lancet, 2020, 395: 497-506.
Hucknall et al., "Simple Fabrication of Antibody Microarrays on Nonfouling Polymer Brushes with Femtomolar Sensitivity for Protein Analytes in Serum and Blood," Adv Mater, 2009, 21(19): 1968-1971.
Jiang et al., "Neutralizing Antibodies against SARS-CoV-2 and Other Human Coronaviruses," Trends Immunol, 2020, 41(5): 355-359.
Joh et al., "Architectural Modification of Conformal PEG-Bottlebrush Coatings Minimizes Anti-PEG Antigenicity While Preserving Stealth Properties," Advanced Healthcare Materials, 2019, 8(8): 1801177, 27 pages.
Joh et al., "Inkjet-printed point-of-care immunoassay on a nanoscale polymer brush enables subpicomolar detection of analytes in blood," Proc Natl Acad Sci U S A, 2017, 114: E7054-E7062.
Kang et al., "Crystal structure of SARS-CoV-2 nucleocapsid protein RNA binding domain reveals potential unique drug targeting sites," Acta Pharm Sin B, 2020, 10(7): 1228-1238.
Khailany et al., "Genomic characterization of a novel SARS-CoV-2," Gene Rep, 2020, 9: 100682, 6 pages.
Kozel et al., "Point-of-care testing for infectious diseases: past, present, and future," J Clin Microbiol, 2017, 55: 2313-2320.
Kozma et al., "Anti-PEG antibodies: Properties, formation, testing and role in adverse immune reactions to PEGylated nano-biopharmaceuticals," Adv Drug Deliv Rev, 2020, 154-155, 163-175.
Krammer et al., "Serology assays to manage COVID-19," Science, 2020, 368: 1060-1061.
Kuo et al., "Global epidemiology of gout: prevalence, incidence and risk factors," Nature Reviews Rheumatology, 2015, 11: 649-662.
Laing et al., "A dynamic COVID-19 immune signature includes associations with poor prognosis," Nat Med, 2020, 26:1623-1635.
Lieberman et al., "Comparison of Commercially Available and Laboratory-Developed Assays for in Vitro Detection of SARS-CoV-2 in Clinical Laboratories," J Clin Microbiol, 2020, 58(8):e00821-20.
Lipsitch et al., "Antibody testing will enhance the power and accuracy of COVID-19-prevention trials," Nat Med, 2020, 26: 818-819.
Lipsky et al., "Pegloticase immunogenicity: the relationship between efficacy and antibody development in patients treated for refractory chronic gout," Arthritis Res Ther, 2014, 16: R60.
Lisboa Bastos et al., "Diagnostic accuracy of serological tests for covid-19: systematic review and meta-analysis," BMJ, 2020, 370: m2516.
Liu et al., "High neutralizing antibody titer in intensive care unit patients with COVID-19," Emerg Microbes Infect, 2020, 9: 1664-1670.
Liu et al., "Semi-permeable coatings fabricated from comb-polymers efficiently protect proteins in vivo," Nature Communications, 2014, 5: 5526.

(56) References Cited

OTHER PUBLICATIONS

Liu et al., "The experiences of health-care providers during the COVID-19 crisis in China: a qualitative study," Lancet Glob Health, 2020, 8: e790-e798.
Lu et al., "Genomic characterisation and epidemiology of 2019 novel coronavirus: implications for virus origins and receptor binding," Lancet, 2020, 395: 565-574.
McAndrews et al., "Heterogeneous antibodies against SARS-CoV-2 spike receptor binding domain and nucleocapsid with implications for COVID-19 immunity," JCI Insight, 2020, 5(18):e142386, 14 pages.
McElvaney et al., "A linear prognostic score based on the ratio of interleukin-6 to interleukin-10 predicts outcomes in COVID-19," EBioMedicine, 2020, 61: 103026, 8 pages.
Mejía-Salazar et al., "Microfluidic Point-of-Care Devices: New Trends and Future Prospects for eHealth Diagnostics," Sensors, 2020, 20: 1951, 19 pages.
Miller et al., "Disease and healthcare burden of COVID-19 in the United States," Nat Med, 2020, 26: 1212-1217.
Nalla et al., "Comparative Performance of SARS-CoV-2 Detection Assays Using Seven Different Primer-Probe Sets and One Assay Kit," J Clin Microbiol, 2020, 58: e00557-20, 6 pages.
Norman et al., "Ultrasensitive high-resolution profiling of early seroconversion in patients with COVID-19," Nat Biomed Eng, 2020, 11 pages.
Nunn et al., "Crystal Structure of Tobacco Etch Virus Protease Shows the Protein C Terminus Bound within the Active Site," Journal of Molecular Biology, 2005, 350: 145-155.
Nyborg et al., "A Therapeutic Uricase with Reduced Immunogenicity Risk and Improved Development Properties," PLoS One, 2016, 11(12): e0167935, 23 pages.
Okba et al., "Severe Acute Respiratory Syndrome Coronavirus 2-Specific Antibody Responses in Coronavirus Disease Patients," Emerg Infect Dis, 2020, 26: 1478-1488.
Ozer et al., "Effect of Molecular Architecture on Cell Interactions and Stealth Properties of PEG," Biomacromolecules, 2017, 18: 2699-2710.
Pecoraro et al., "A systematic evaluation of immunoassay point-of-care testing to define impact on patients' outcomes," Ann Clin Biochem, 2017, 54(4): 420-431.
Ponti et al., "Biomarkers associated with COVID-19 disease progression," Crit Rev Clin Lab Sci, 2020, 57, 11 pages.
Posthuma-Trumpie et al., "Lateral flow (immuno)assay: its strengths, weaknesses, opportunities and threats. A literature survey," Anal Bioanal Chem, 2009, 393: 569-582.
Radzicka et al., "Comparing the Polrities of the Amino Acids: Side-Chain Distribution Coefficients between the Vapor Phase, Cyclohexane, 1-Octanol, and Neutral Aqueous Solution," Biochemistry, 1988, 27: 1664-1670.
Ravichandran et al., "Antibody signature induced by SARS-CoV-2 spike protein immunogens in rabbits," Sci Transl Med, 2020, 10.1126/scitranslmed.abc3539, 9 pages.
Rogers et al., "Isolation of potent SARS-CoV-2 neutralizing antibodies and protection from disease in a small animal model," Science, 2020, 369: 956-963.
Rosadas et al., "Testing for responses to the wrong SARS-CoV-2 antigen," Lancet, 2020, 396: e23.
Rothe et al., "Transmission of 2019-nCoV Infection from an Asymptomatic Contact in Germany," N Engl J Med, 2020, 382: 10, 2 pages.
Seow et al., "Longitudinal evaluation and decline of antibody responses in SARS-CoV-2 infection," medRxiv, 2020, 24 pages.
Sundy et al., "Efficacy and tolerability of pegloticase for the treatment of chronic gout in patients refractory to conventional treatment: two randomized controlled trials," Jama, 2011, 306(7): 711-720.
Sundy et al., "Pharmacokinetics and pharmacodynamics of intravenous PEGylated recombinant mammalian urate oxidase in patients with refractory gout," Arthritis Rheum, 2007, 56(3): 1021-1028.
Tang et al., "Laboratory Diagnosis of COVID-19: Current Issues and Challenges," J Clin Microbiol, 2020, 58: e00512-20, 9 pages.
Turner et al., "Challenges and Opportunities for the Subcutaneous Delivery of Therapeutic Proteins," Journal of Pharmaceutical Sciences, 2018, 107(5): 1247-1260.
U.S. FDA—Classify your medical devices. Updated as of: Feb. 7, 2020. Available at: <https://www.fda.gov/medical-devices/overview-device-regulation/classify-your-medical-device>.
U.S. FDA—In Vitro Diagnostics. Updated as of: Oct. 25, 2019. Available at: <https://www.fda.gov/medical-devices/products-and-medical-procedures/vitro-diagnostics>.
Vaninov, "In the eye of the COVID-19 cytokine storm," Nat Rev Immunol, 2020, 20: 277, 1 page.
Vashist et al., "Emerging Technologies for Next-Generation Point-of-Care Testing," Trends Biotechnol, 2015, 33(11): 692-705.
Verhoef et al., "Potential induction of anti-PEG antibodies and complement activation toward PEGylated therapeutics," Drug Discov Today, 2014, 19(12): 1945-1952.
Vugmeyster et al., "Pharmacokinetics and toxicology of therapeutic proteins: Advances and challenges," World J Biol Chem, 2012, 3(4): 73-92.
Waterboer et al., "Suppression of non-specific binding in serological Luminex assays," J Immunol Methods, 2006, 309: 200-204.
Weinhandl et al., "Relative safety of peginesatide and epoetin alfa," Pharmacoepidemiology and Drug Safety, 2014, 23(10): 1003-1011.
Whitman et al., "Evaluation of SARS-CoV-2 serology assays reveals a range of test performance," Nat Biotechnol, 2020, 38: 1174-1183.
Wiersinga et al., "Pathophysiology, Transmission, Diagnosis, and Treatment of Coronavirus Disease 2019 (COVID-19): A Review," JAMA, 2020, 324(8): 782-793.
Winter et al., "The important role of serology for COVID-19 control," Lancet Infect Dis, 2020, 20: 758-759.
Wölfel et al., "Virological assessment of hospitalized patients with COVID-2019," Nature, 2020, 581: 465-469.
Yang et al., "Analysis of Pre-existing IgG and IgM Antibodies against Polyethylene Glycol (PEG) in the General Population," Analytical Chemistry, 2016, 88(23): 11804-11812.
Yang et al., "Anti-PEG immunity: emergence, characteristics, and unaddressed questions," Wiley Interdiscip Rev Nanomed Nanobiotechnol, 2015, 7(5): 655-677.
Yang et al., "Plasma IP-10 and MCP-3 levels are highly associated with disease severity and predict the progression of COVID-19," J Allergy Clin Immunol, 2020, 146: 119-127.
Yang et al., "Uricases as therapeutic agents to treat refractory gout: Current states and future directions," Drug Dev Res, 2012, 73(2): 66-72.
Yong et al., "Connecting clusters of COVID-19: an epidemiological and serological investigation," Lancet Infect Dis, 2020, 20: 809-815.
Zhang et al., "Anti-PEG antibodies in the clinic: Current issues and beyond PEGylation," J Control Release, 2016, 244(Pt B): 184-193.
Zhang et al., "Impact of Large Aggregated Uricases and PEG Diol on Accelerated Blood Clearance of PEGylated Canine Uricase," PLoS ONE, 2012, 7(6): e39659.
Zhao et al., "Antibody responses to SARS-CoV-2 in patients of novel coronavirus disease 2019," Clin Infect Dis, 2020, 22 pages.
International Search Report and Written Opinion for Application No. PCT/US2021/020591 dated Oct. 7, 2021 (14 pages).
United States Patent Office Action for U.S. Appl. No. 16/614,282 dated Oct. 21, 2021 (14 pages).
United States Patent Office Action for U.S. Appl. No. 15/749,797 dated Nov. 29, 2021 (10 pages).
United States Patent Office Action for U.S. Appl. No. 16/477,229 dated Oct. 26, 2021 (10 pages).
International Search Report and Written Opinion for Application No. PCT/US2021/046833 dated Nov. 8, 2021 (13 pages).
International Search Report and Written Opinion for Application No. PCT/US2021/035823 dated Dec. 8, 2021 (16 pages).
United States Patent Office Action for U.S. Appl. No. 17/265,165 dated Dec. 21, 2021 (11 pages).
United States Patent Office Action for U.S. Appl. No. 16/625,899 dated Dec. 15, 2021 (12 pages).

(56) References Cited

OTHER PUBLICATIONS

United States Patent Office Action for U.S. Appl. No. 16/927,982 dated Jan. 6, 2022 (6 pages).
Chan et al., "A randomized, repeat-dose, pharmacodynamic and safety study of an antidote-controlled factor IXa inhibitor," J Thromb Haemost, 2008, 6(5): 789-796.
Chan et al., "Phase 1b randomized study of antidote-controlled modulation of factor IXa activity in patients with stable coronary artery disease," Circulation, 2008, 117(22): 2865-2874.
Chappell et al., "Computational design of small transcription activating RNAs for versatile and dynamic gene regulation," Nat Commun, 2017, 8(1): 1051.
Chappell et al., "Creating small transcription activating RNAs," Nat Chem Biol, 2015, 11(3): 214-220.
Chase et al., "Single-Stranded DNA Binding Proteins Required for DNA Replication," Ann. Rev. Biochem., 1986, 55: 103-136.
Cohen et al., "First clinical application of an actively reversible direct factor IXa inhibitor as an anticoagulation strategy in patients undergoing percutaneous coronary intervention," Circulation, 2010, 122(6): 614-622.
Dale et al., "Direct covalent mercuration of nucleotides and polynucleotides," Biochemistry, 1975, 14(11): 2447-2457.
Davis et al., "Antibodies and the RNA World: A Role for Low-molecular-weight Effectors in Biochemical Evolution," RNA World, 1993, Chapter 8, p. 185-204.
Dyke et al., "First-in-human experience of an antidote-controlled anticoagulant using RNA aptamer technology: a phase 1a pharmacodynamic evaluation of a drug-antidote pair for the controlled regulation of factor IXa activity," Circulation, 2006, 114(23): 2490-2497.
Eichhorn et al., "Interactions of metal ions with polynucleotides and related compounds. XII. The relative effect of various metal ions on DNA helicity," J. Am. Chem. Soc, 1968, 90: 7323-7328.
Ganesan et al., "Lipid Nanoparticles: Different Preparation Techniques, Characterization, Hurdles, and Strategies for the Production of Solid Lipid Nanoparticles and Nanostructured Lipid Carriers for Oral Drug Delivery," Sustain. Chem. Pharm., 2017, 6: 37-56.
Gold et al., "Aptamers and the RNA World, Past and Present," Cold Spring Harbor Perspect. Biol., 2012, 4: a003582, 9 pages.
Heus, "RNA aptamers," Nat Struct Biol, 1997, 4(8): 597-600.
Hucknall et al., "Simple Fabrication of Antibody Microarrays on Nonfouling Polymer Brushes with Femtomolar Sensitivity for Protein Analytes in Serum and Blood," Adv Mater, 2009, 21: 1968-1971.
Hwang et al., "Inhibition of gene expression in human cells through small molecule-RNA interactions," Proc. Natl. Acad. Sci. USA, 1999, 96(23): 12997-13002.
Keefe et al., "Aptamers as therapeutics," Nature Reviews Drug Discovery, 2010, 9: 537-550.
Korte et al., "Short activated partial thromboplastin times are related to increased thrombin generation and an increased risk for thromboembolism," Am J Clin Pathol, 2000, 113(1): 123-127.
Li et al., "Ferric Chloride-induced Murine Thrombosis Models," J. Vis. Exp., 2016, 115: e54479, 12 pages.
Lincoff et al., "Effect of the REG1 anticoagulation system versus bivalirudin on outcomes after percutaneous coronary intervention (Regulate-PCI): a randomised clinical trial," Lancet, 2016, 387(10016): 349-356.
Lippard et al., "Platinum complexes: probes of polynucleotide structure and antitumor drugs," Acc. Chem. Res., 1978, 11(5): 211-217.
Maier et al., "From selection hits to clinical leads: progress in aptamer discovery," Mol. Ther. Methods Clin. Dev., 2016, 3: 16014, 10 pages.
McManus et al., "Gene silencing in mammals by small interfering RNAs," Nat Rev Genet, 2002, 3(10): 737-747.
Moreno et al., "Anti-PEG Antibodies Inhibit the Anticoagulant Activity of PEGylated Aptamers," Cell Chem Biol, 2019, 26(5): 634-644.e3.
Nimjee et al., "Aptamers as Therapeutics," Annu Rev Pharmacol Toxicol, 2017, 57: 61-79.
Pisal et al., "Delivery of therapeutic proteins," Journal of Pharmaceutical Sciences, 2010, 99(6): 2557-2575.
Povsic et al., "A Phase 2, randomized, partially blinded, active-controlled study assessing the efficacy and safety of variable anticoagulation reversal using the REG1 system in patients with acute coronary syndromes: results of the Radar trial," Eur Heart J, 2013, 34(31): 2481-2489.
Povsic et al., "Pre-existing anti-PEG antibodies are associated with severe immediate allergic reactions to pegnivacogin, a PEGylated aptamer," J Allergy Clin Immunol, 2016, 138(6): 1712-1715.
Purtell et al., "Isoelectric point of albumin: effect on renal handling of albumin," Kidney Int, 1979, 16(3): 366-376.
Richter et al., "Mechanistic determinants of biotherapeutics absorption following SC administration," AAPS J, 2012, 14(3): 559-570.
Rinaldi et al., "Antisense oligonucleotides: the next frontier for treatment of neurological disorders," Nat Rev Neurol, 2018, 14(1): 9-21.
Rusconi et al., "Antidote-mediated control of an anticoagulant aptamer in vivo," Nat Biotechnol, 2004, 22(11): 1423-1428.
Rusconi et al., "RNA aptamers as reversible antagonists of coagulation factor Ixa," Nature, 2002, 19(6902): 90-94.
Shu et al., "GISAID: Global initiative on sharing all influenza data—from vision to reality," Euro Surveill 22, 2017, 22(13): 30494, 3 pages.
Smith et al., "Coronaviruses lacking exoribonuclease activity are susceptible to lethal mutagenesis: evidence for proofreading and potential therapeutics," PLoS Pathog, 2013, 9: e1003565, 11 pages.
Tuerk et al., "Systematic evolution of ligands by exponential enrichment: RNA ligands to bacteriophage T4 DNA polymerase," Science, 1990, 249(4968): 505-510.
Werstuck et al., "Controlling gene expression in living cells through small molecule-RNA interactions," Science, 1998, 282(5387): 296-298.
Woodruff et al., "Modulation of the Coagulation Cascade Using Aptamers," Arterioscler Thromb Vasc Biol, 2015, 35(10): 2083-2091.
Yamaoka et al., "Distribution and tissue uptake of poly(ethylene glycol) with different molecular weights after intravenous administration to mice," Journal of Pharmaceutical Sciences, 1994, 83(4): 601-606.
Yizhi et al., "A brush-polymer/exendin-4 conjugate reduces blood glucose levels for up to five days and eliminates poly(ethylene glycol) antigenicity," Nature Biomedical Engineering, 2016, 1(1): 0002.
Zhou et al., "Aptamers as targeted therapeutics: current potential and challenges," Nat Rev Drug Discov, 2017, 16(3): 181-202.
Gilroy et al., "Sustained release of a GLP-1 and FGF21 dual agonist from an injectable depot protects mice from obesity and hyperglycemia," Science Advances, 2020, 6(35): eaaz9890, 12 pages.
United States Patent Office Notice of Allowance for U.S. Appl. No. 15/749,797 dated Mar. 16, 2022 (6 pages).
United States Patent Office Action for U.S. Appl. No. 16/477,229 dated Mar. 3, 2022 (10 pages).
Ozer et al., "Injectable non-immunogenic PEG-like conjugate that forms a subcutaneous depot and enables sustained delivery of a peptide drug," Research Square, 2021, 38 pages.
Hu et al., "Site-specific in situ growth of a cyclized protein-polymer conjugate with improved stability and tumor retention," Biomaterials, 2015, 47:13-19.
International Search Report and Written Opinion for Application No. PCT/US2022/041241 dated Oct. 25, 2022 (10 pages).
United States Patent Office Action for Application No. 17/265,165 dated Sep. 2, 2022 (5 pages).
United States Patent Office Action for U.S. Appl. No. 17/015,315 dated Dec. 23, 2022 (10 pages).
United States Patent Office Notice of Allowance for U.S. Appl. No. 16/477,229 dated Jan. 6, 2023 (8 pages).
United States Patent Office Notice of Allowance for U.S. Appl. No. 17/265,165 dated Jan. 10, 2023 (7 pages).
United States Patent Office Notice of Allowance for U.S. Appl. No. 16/625,899 dated Jan. 18, 2023 (8 pages).

(56) References Cited

OTHER PUBLICATIONS

Erbacher et al., "Transfection and Physical Properties of Various Saccharide, Poly(ethylene glycol), and Antibody-Derivatized Polyethylenimines (PEI)," The Journal of Gene Medicine, 1999, 1: 210-222.
Alves et al., "Influence of doxorubicin on model cell membrane properties: insight from in vitro and in silico studies," Sci Rep, 2017, 7(1): 6343.
International Search Report and Written Opinion for Application No. PCT/US2022/078659 dated Feb. 1, 2023 (17 pages).
United States Patent Office Notice of Allowance for U.S. Appl. No. 17/015,315 dated Apr. 26, 2023 (7 pages).
United States Patent Office Action for U.S. Appl. No. 17/051,202 dated Jun. 21, 2023 (10 pages).
Liu et al., "Stable Evans Blue Derived Exendin-4 Peptide for Type 2 Diabetes Treatment," Bioconjugate Chem, 2016, 27: 54058.
Cereghetti et al., "Reversible, functional amyloids: towards an understanding of their regulation in yeast and humans," Cell Cycle, 2018, 17(13): 1545-1558.
Uversky et al., "Life in Phases: Intra- and Inter- Molecular Phase Transitions in Protein Solutions," Biomolecules, 2019, 9(12): 842.
McPherson, "Product purification by reversible phase transition following *Escherichia coli* expression of genes encoding up to 251 repeats of the elastomeric pentapeptide GVGVP," Protein Expression and Purification, 1996, 7: 51-57.
Cascarina et al., "Generalizable Compositional Features Influencing the Proteostatic Fates of Polar Low-Complexity Domains," International Journal of Molecular Sciences, 2021, 22(16): 8944.
Krainer et al., "Reentrant liquid condensate phase of proteins is stabilized by hydrophobic and non-ionic interactions," Nature Communications, 2021, 12(1): 1085.
United States Patent Office Action for U.S. Appl. No. 17/477,192 dated Jan. 4, 2024 (11 pages).
United States Patent Office Notice of Allowance for U.S. Appl. No. 18/051,487 dated Dec. 11, 2023 (5 pages).
United States Patent Office Action for U.S. Appl. No. 17/051,202 dated Jan. 19, 2024 (5 pages).
Ren et al., "Stimulus-Responsive Polymer Prodrugs," Progress in Chemistry, 2013, 25(5): 10 pages.
United States Patent Office Action for U.S. Appl. No. 16/614,282 dated Apr. 27, 2022 (15 pages).
United States Patent Office Notice of Allowance for U.S. Appl. No. 16/305,696 dated May 23, 2022 (10 pages).
United States Patent Office Notice of Allowance for U.S. Appl. No. 16/305,696 dated Jun. 10, 2022 (4 pages).
United States Patent Office Notice of Allowance for U.S. Appl. No. 15/749,797 dated Jun. 2, 2022 (6 pages).
United States Patent Office Action for U.S. Appl. No. 16/477,229 dated Jun. 13, 2022 (11 pages).
Da Pieve Chiara et al., "Modification of Thiol Functionalized Aptamers by Conjugation of Synthetic Polymers," Bioconjugate Chemistry, 2009, 1(1): 169-174.
International Search Report and Written Opinion for Application No. PCT2022/023158 dated Jun. 21, 2022 (7 pages).
International Search Report and Written Opinion for Application No. PCT/US2022/017349 dated Jun. 3, 2022 (20 pages).
United States Patent Office Notice of Allowance for U.S. Appl. No. 16/614,282 dated Aug. 23, 2022 (7 pages).
United States Patent Office Notice of Allowance for U.S. Appl. No. 16/927,982 dated Jul. 15, 2022 (8 pages).
Singh et al., "Polymeric microneedles for controlled transdermal drug delivery," Journal of Controlled Release, 2019, 315: 97-113.
Vancoillie et al., "Thermoresponsive poly(oligo ethylene glycol acrylates)," Progress in Polymer Science, 2014, 39(6): 1074-1095.
Zhang et al., "A triple thermoresponsive schizophrenic diblock copolymer," Polymer Chemistry, 2013, 4(16): 4322-4325.
International Search Report and Written Opinion for Application No. PCT/US2024/050476 dated Nov. 25, 2024 (18 pages).
United States Patent Office Notice of Allowance for U.S. Appl. No. 17/051,202 dated Nov. 15, 2024 (7 pages).
United States Patent Office Action for U.S. Appl. No. 17/272,887 dated Nov. 21, 2024 (13 pages).

\* cited by examiner

ALBUMIN BINDING PEPTIDE-DRUG (AlBiPeD) CONJUGATES AND METHODS OF MAKING AND USING SAME

CROSS-REFERENCE TO RELATED APPLICATIONS

This application is the U.S. national stage entry, under 35 U.S.C. § 371, of International Application Number PCT/US2019/015176, filed Jan. 25, 2019, which claims priority to U.S. Provisional Patent Application No. 62/622,249, filed Jan. 26, 2018, the entire contents of each of which are hereby incorporated by reference.

STATEMENT REGARDING FEDERALLY-SPONSORED RESEARCH OR DEVELOPMENT

This invention was made with government support under grant numbers R01EB000188 and R01EB007205 awarded by the National Institutes of Health. The government has certain rights in the invention.

SEQUENCE LISTING

The instant application contains a Sequence Listing which has been submitted electronically and is hereby incorporated by reference in its entirety. The sequence listing text filed, created on Jan. 23, 2019, is named "028193-9315-WO01 As Filed Sequence Listing" and is 2,629 bytes in size.

TECHNICAL FIELD

The present disclosure relates to a novel drug delivery system.

BACKGROUND OF THE INVENTION

Delivery and therapeutic efficacy of small molecule imaging agents and chemotherapeutics are hampered by their short half-life, low solubility, non-selectivity to cancer cells, and toxic side effects. Small molecule chemotherapeutics, although in routine use for cancer treatment, suffer from a short circulation half-life and indiscriminate accumulation in healthy tissues that result in systemic toxicities and hence limit their maximum dose. These limitations inhibit accumulation of chemotherapeutics in tumors at therapeutic levels and limit their clinical application. Efforts in past decades have been focused on developing macromolecular and nanoparticulate drug formulations that prevent first-pass elimination in kidneys and allow for selective accumulation in tumors via the enhanced permeation and retention (EPR) effect. However, the interaction of these macromolecule and nanoparticle carriers with serum proteins and components of the immune system is not well understood and is affected by several factors such as their interfacial chemistry, size, shape and stability which makes their optimization difficult. Therefore, there remains a need for new delivery systems that can overcome these disadvantages yet provide efficacy for delivery of small molecule imaging agents and chemotherapeutics.

BRIEF SUMMARY OF THE INVENTION

The present disclosure is directed to compositions comprising an albumin binding domain (ABD), a linker coupled to the ABD, and at least one molecule coupled to the linker.

The present disclosure is directed to methods of killing cancer cells comprising contacting cancer cells with an effective amount of the compositions disclosed herein.

The present disclosure is also directed to methods of treating a disease or disorder in a subject comprising administering to the subject a therapeutically effective amount of the compositions disclosed herein. The disease or disorder may be cancer.

The present disclosure is further directed to methods of purifying the compositions disclosed herein. The methods may comprise forming a conjugate comprising an elastin-like polypeptide having a transition temperature ($T_t$) above 50° C.; and the compositions disclosed herein, wherein the composition is conjugated to a first end of the elastin-like polypeptide by an amino acid sequence amenable to cleavage, treating the conjugate with an enzyme, chemical or combination thereof capable of cleaving the amino acid sequence amenable to cleavage, and separating the composition from the elastin-like polypeptide.

Other aspects of the invention will become apparent by consideration of the detailed description and accompanying drawings.

BRIEF DESCRIPTIONS OF THE DRAWINGS

FIG. 1 is a schematic of the conjugate of doxorubicin with an albumin binding domain that binds to and co-opts albumin in vivo for drug delivery to tumors.

Figure 2A:
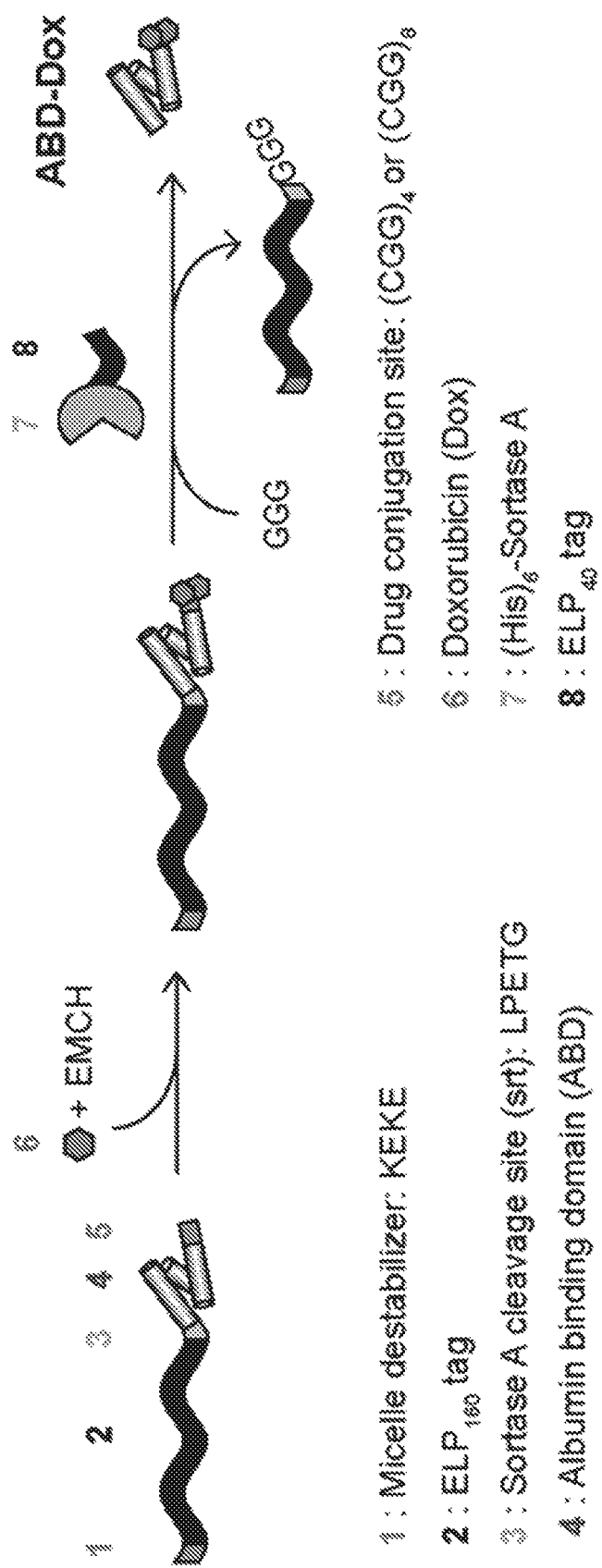
Figure 2B:
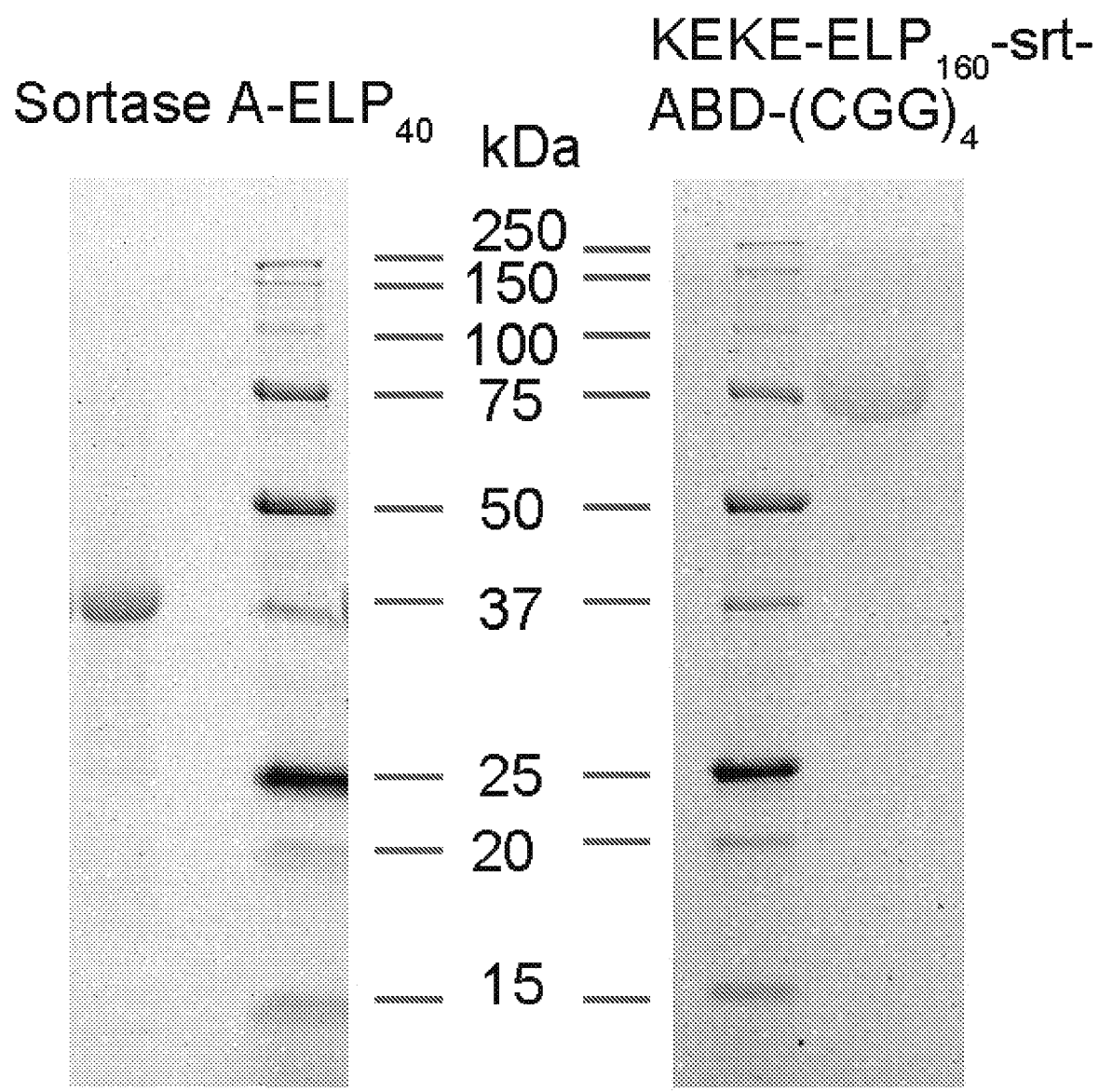
Figure 2C:
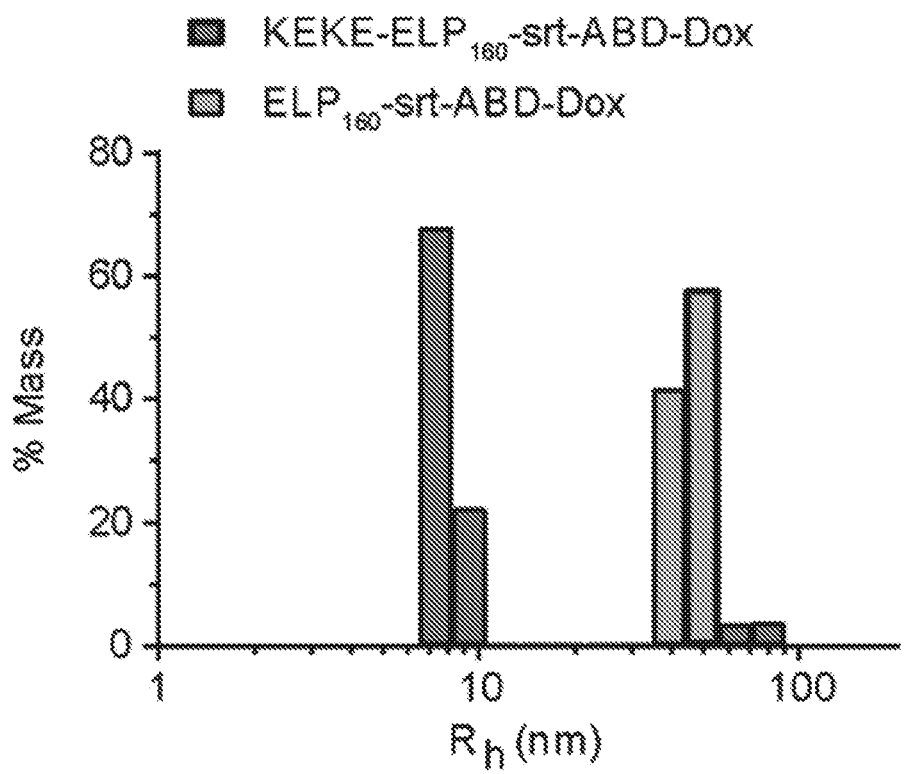

FIG. 2A, FIG. 2B, and FIG. 2C show ABD-Dox synthesis. FIG. 2A is a schematic showing the design and synthesis steps. ELP was used as a purification tag for ABD purification from bacteria and was removed following drug conjugation using sortase A. The KEKE (SEQ ID NO: 5) peptide was included at the N-terminus to disrupt micelle self-assembly upon Dox conjugation, and to enable the subsequent sortase A cleavage of the ELP from the ABD-Dox conjugate. FIG. 2B is an SDS-PAGE analysis confirming successful purification of KEKE-ELP$_{160}$-srt-ABD-(GGC)$_4$ and (His)$_6$-sortase A-ELP$_{40}$ with theoretical molecular weights of 69.4 kDa and 34.4 KDa, respectively. FIG. 2C is a graph of the hydrodynamic radius of ELP$_{160}$-srt-ABD-Dox conjugates as measured with DLS. ELP$_{160}$-srt-ABD-Dox conjugates without the N-terminal KEKE segment (SEQ ID NO: 5) self-assembled into micelles with Rh of 40-50 nm, whereas conjugates containing the N-terminal KEKE segment (SEQ ID NO: 5) were mostly (~90%) unimers with Rh<10 nm.

Figure 3A:
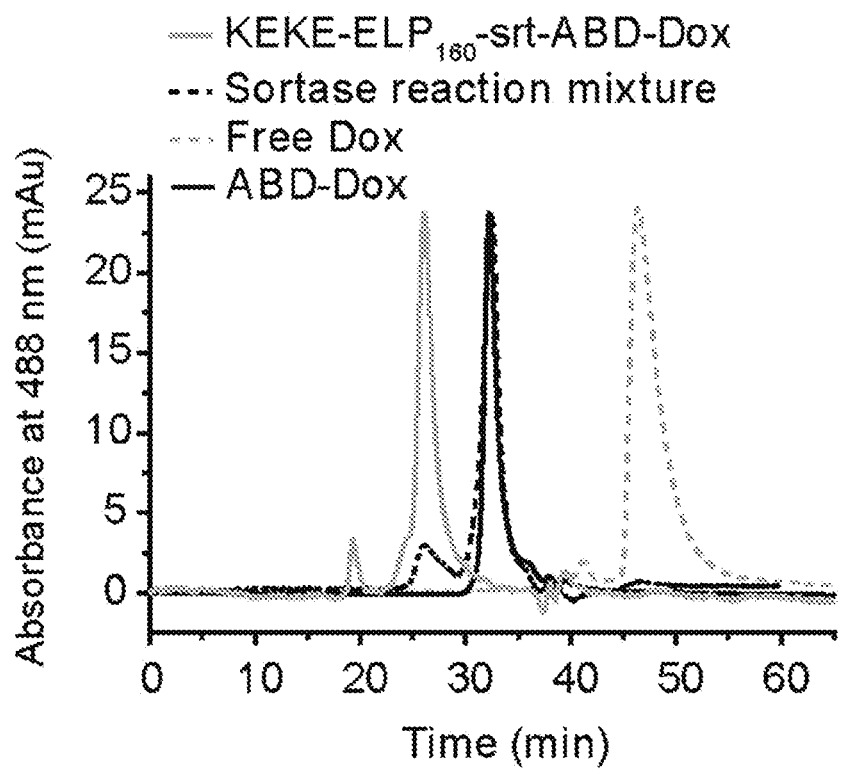
Figure 3B:
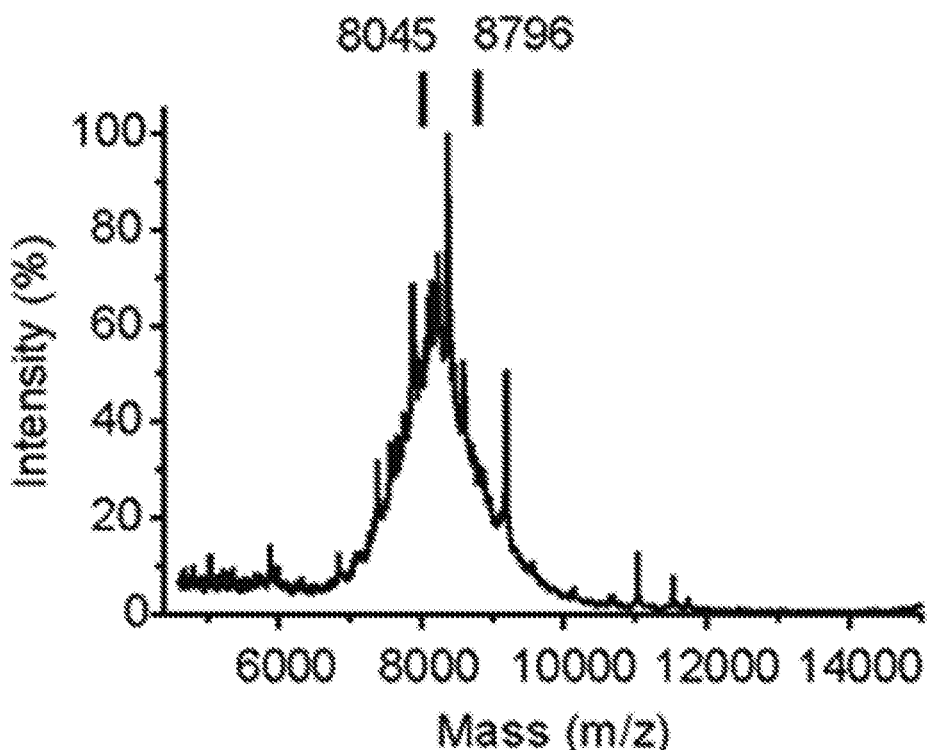
Figure 3C:
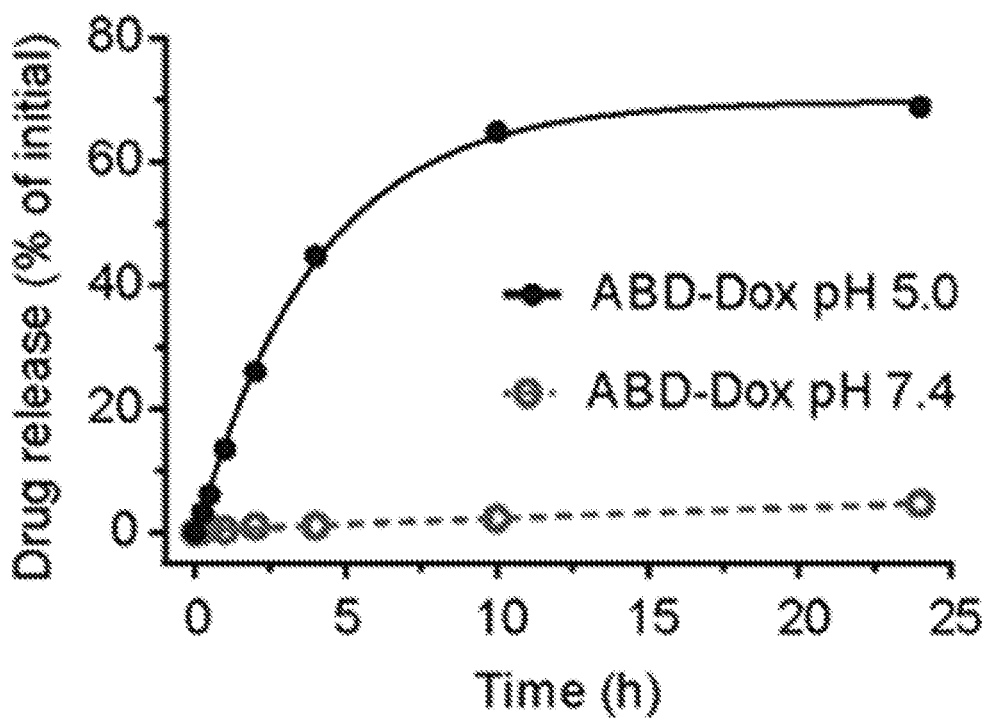
Figure 3D:
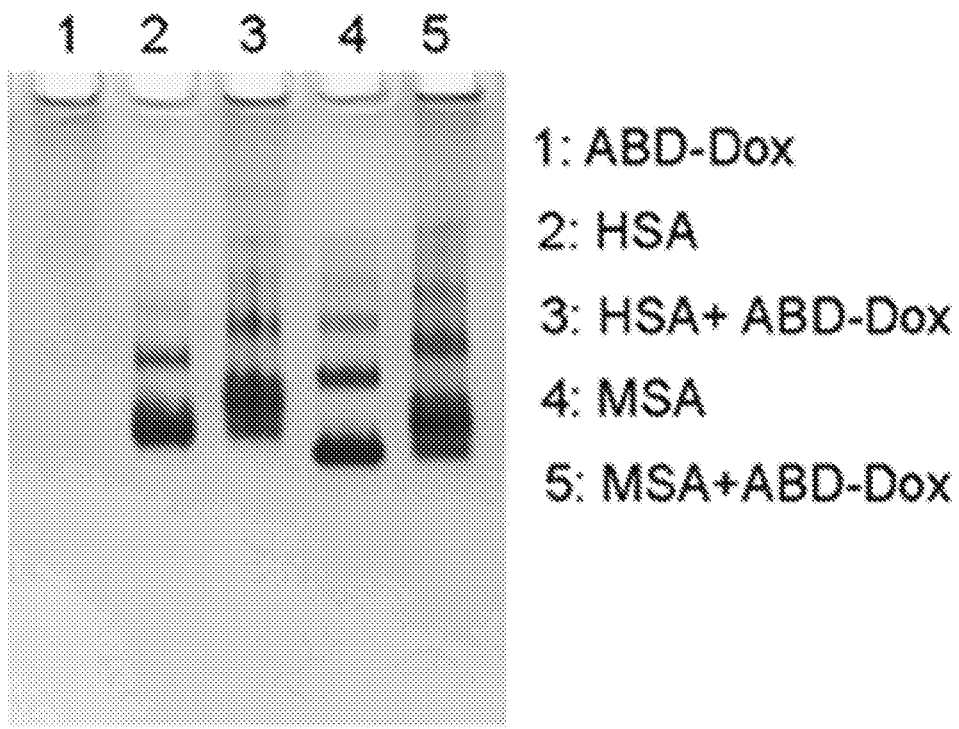
Figure 3E:
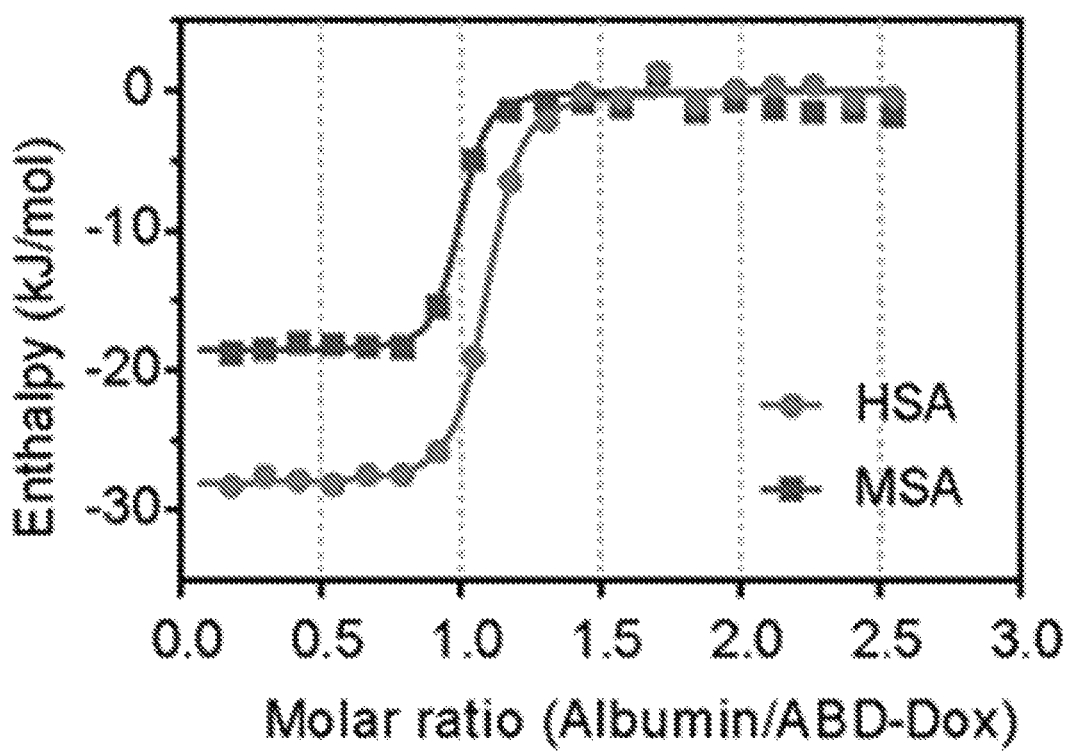
Figure 3F:
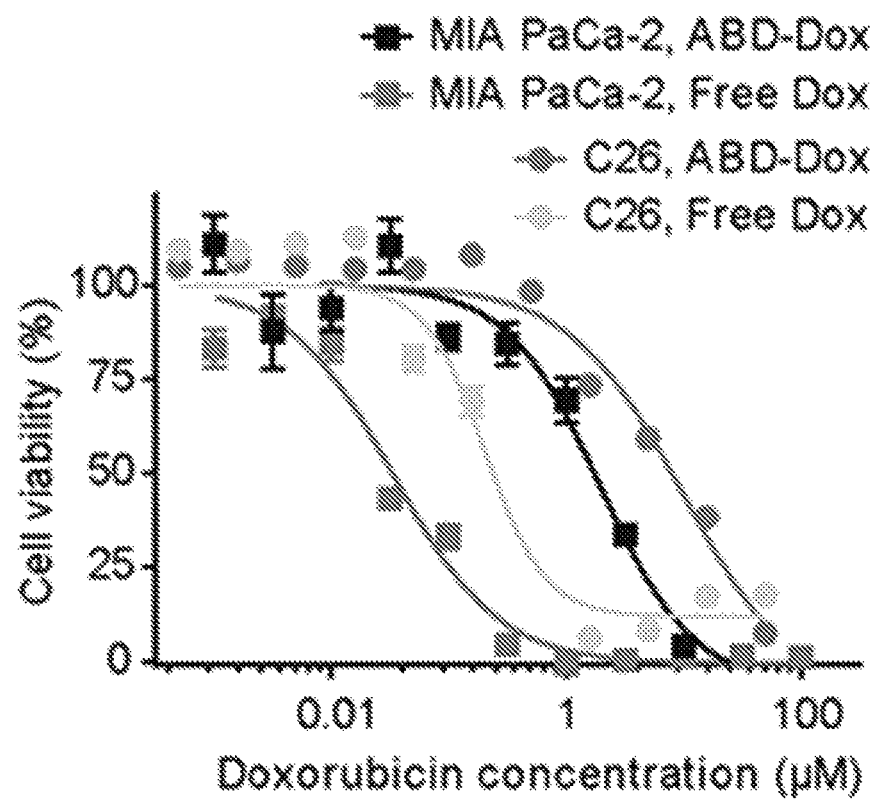

FIG. 3A, FIG. 3B, FIG. 3C, FIG. 3D, FIG. 3E, and FIG. 3F show in vitro characterization of ABD-Dox. FIG. 3A is a plot showing the HPLC chromatograms of the KEKE-ELP160-srt-ABD-Dox, sortase reaction solution after 24 h incubation, and SEC-purified ABD-Dox. FIG. 3B is a plot showing the MALDI-MS spectra of ABD-Dox and vertical bars showing the mass of conjugates with 1 and 2 drug molecules. FIG. 3C is a plot showing the in vitro drug release from ABD-Dox conjugate as a function of time at pH 5.0 and pH 7.0. Dox was released at pH 5.0 corresponding to the pH in late endosomes, and showed a low, basal level of release from the conjugate at pH 7.4, corresponding to the pH in vascular and extracellular space of normal tissues. Data are presented as mean±SEM, n=3. FIG. 3D is a native-PAGE of the interaction of ABD-Dox with human serum albumin (HSA) and mouse serum albumin (MSA). For lanes 3 and 5, ABD-Dox was mixed at a 1:1 molar ratio with HSA and MSA, respectively. FIG. 3E is a plot showing isothermal titration calorimetry thermograms of the interaction of ABD-Dox with HSA and MSA. The enthalpy data were fit to an independent binding site model, and the thermodynamic parameters (n, KD, ΔH, and ΔS) were calculated as shown in Table 1. FIG. 3F shows in vitro cytotoxicity of ABD-Dox and free Dox against C26 and MIA PaCa-2 cancer cells after 72 h incubation. The $IC_{50}$ of ABD-Dox and free Dox were computed as 6.43 and 0.51 µM, respectively, for C26 and as 1.41 and 0.04 µM, respectively, for MIA PaCa-2 cells. Data are presented as mean±SEM, n=3.

Figure 4A:
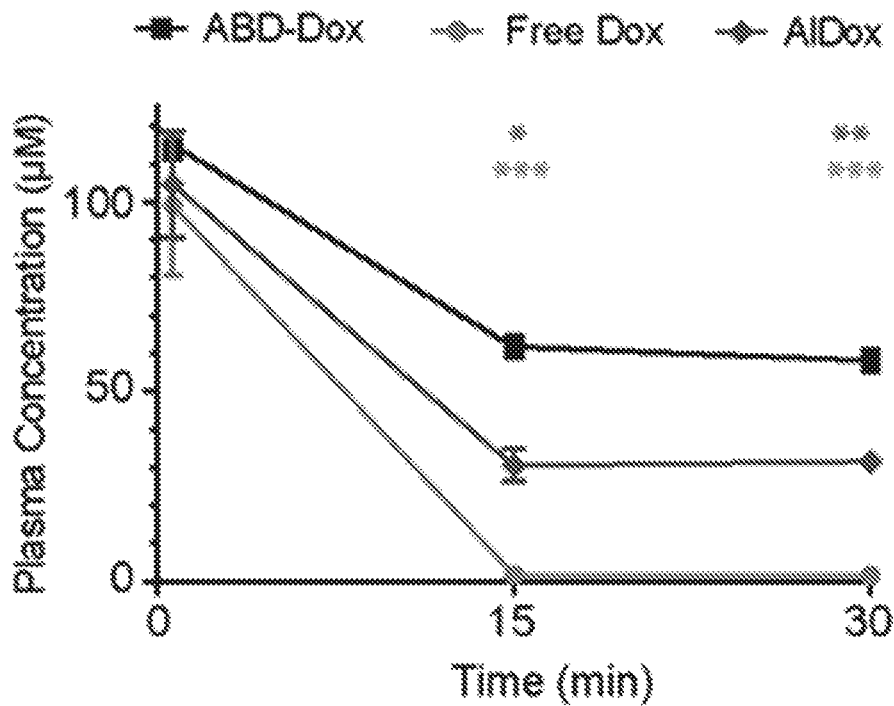
Figure 4B:
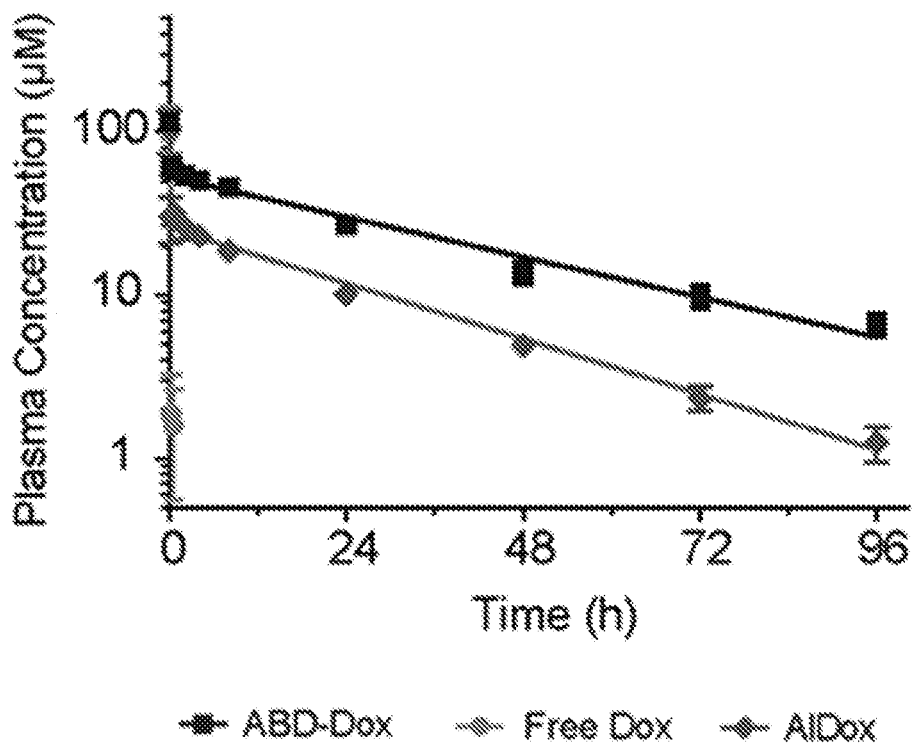

FIG. 4A and FIG. 4B are plots showing the pharmacokinetics of ABD-Dox. Plasma Dox concentration was measured over 96 h (FIG. 3A, 0-30 min view; FIG. 3B, 0-96 h view) after administration of ABD-Dox via tail vein to BALB/c mice and fit to a two-compartment model from which the elimination half-life and the plasma drug exposure (area under the curve) were estimated, and are reported in Table 2. Data are presented as mean±SEM, n=5-6, one-way ANOVA and Tukey's test, * P<0.05,  P<0.01, * P<0.001.

Figure 5A:
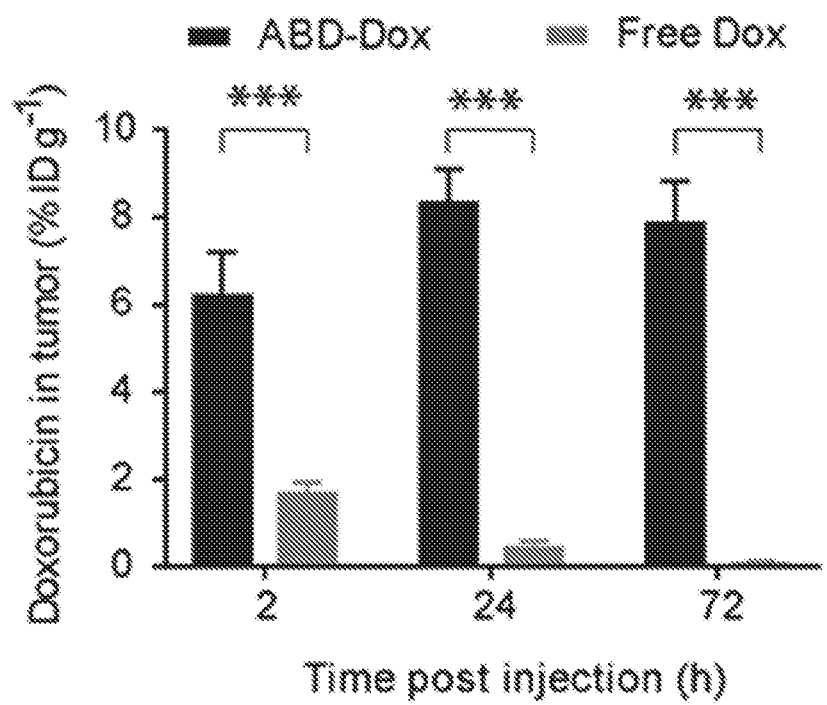
Figure 5B:
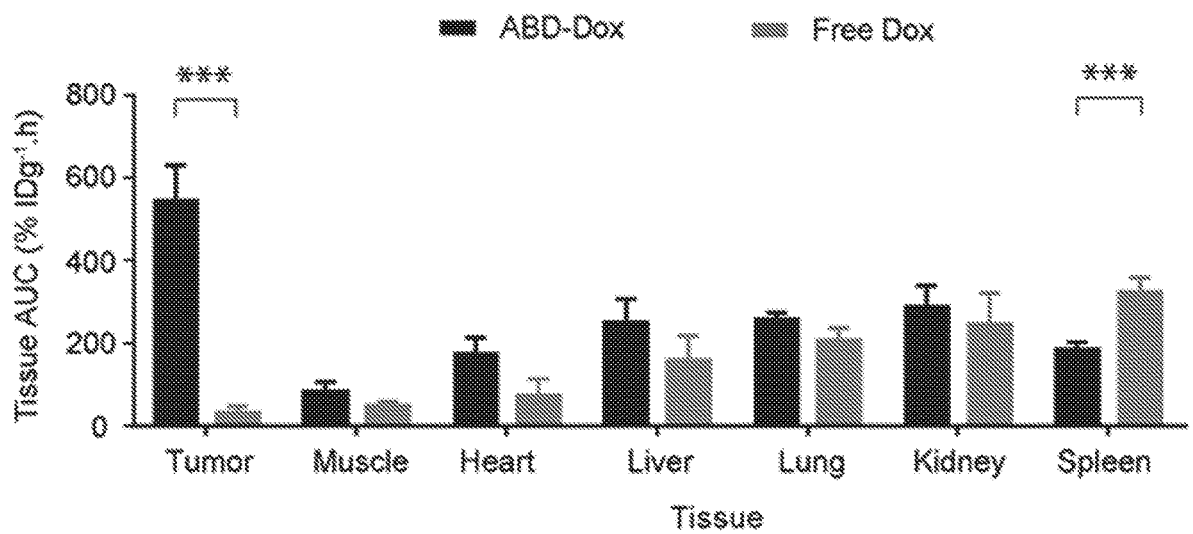

FIG. 5A and FIG. 5B are bar charts showing tissue biodistribution of ABD-Dox. FIG. 5A shows the concentration of ABD-Dox and free Dox in tumor at 2, 24, and 72 h post-administration. ABD-Dox and free Dox were injected into C26-tumor bearing mice, and Dox concentration was measured in tumor and normal tissues at 2 h, 24 h, and 72 h post-administration. FIG. 5B shows the total ABD-Dox exposure in different tissues. Total drug exposure was assessed by calculating the area under the curve (AUC) of the drug concentration-time graph from 2 to 72 h post administration in different tissues. Data are presented as mean±SEM, n=5-7, Student's t-test, *** P<0.001.

Figure 6A:
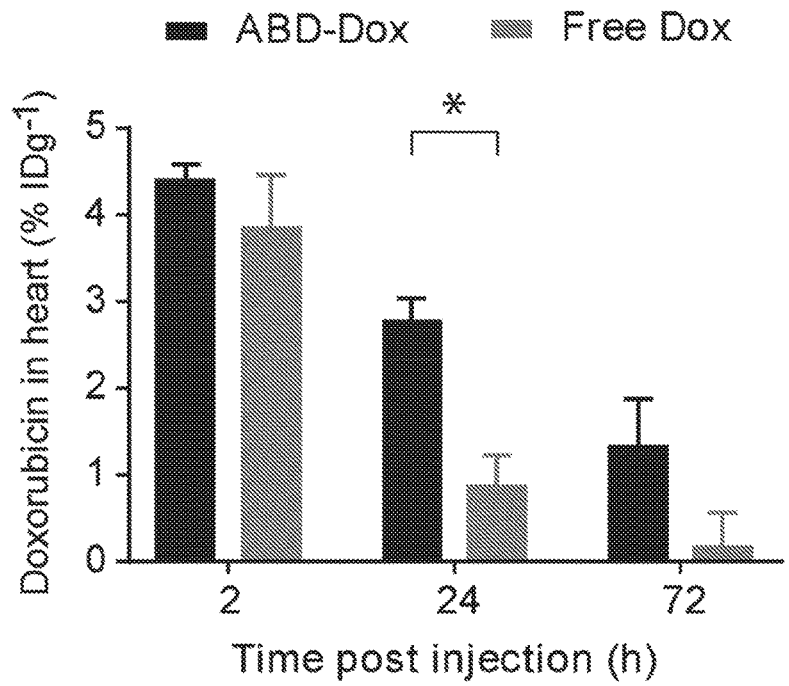
Figure 6B:
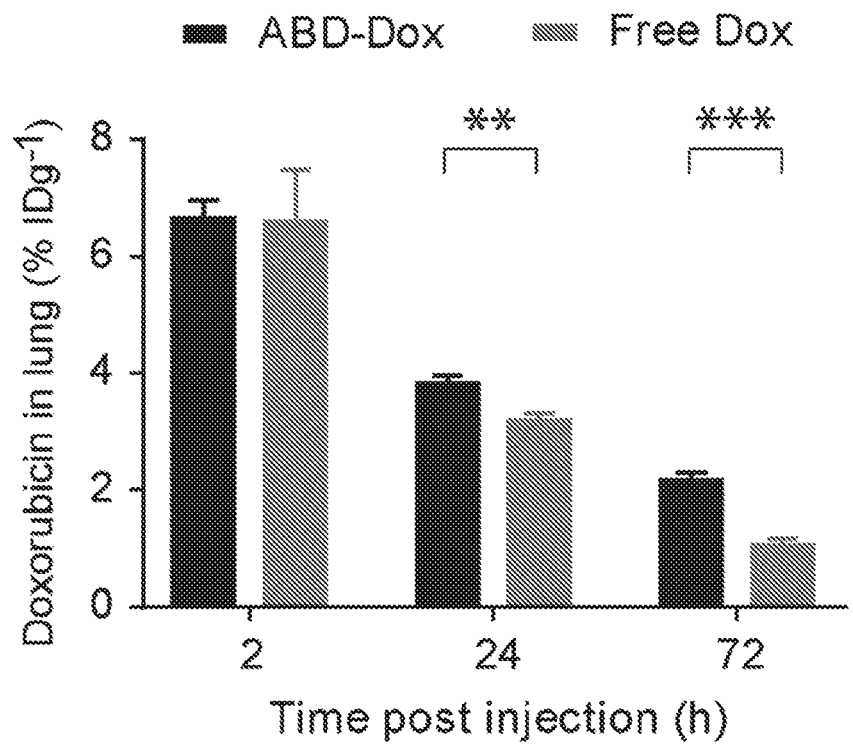
Figure 6C:
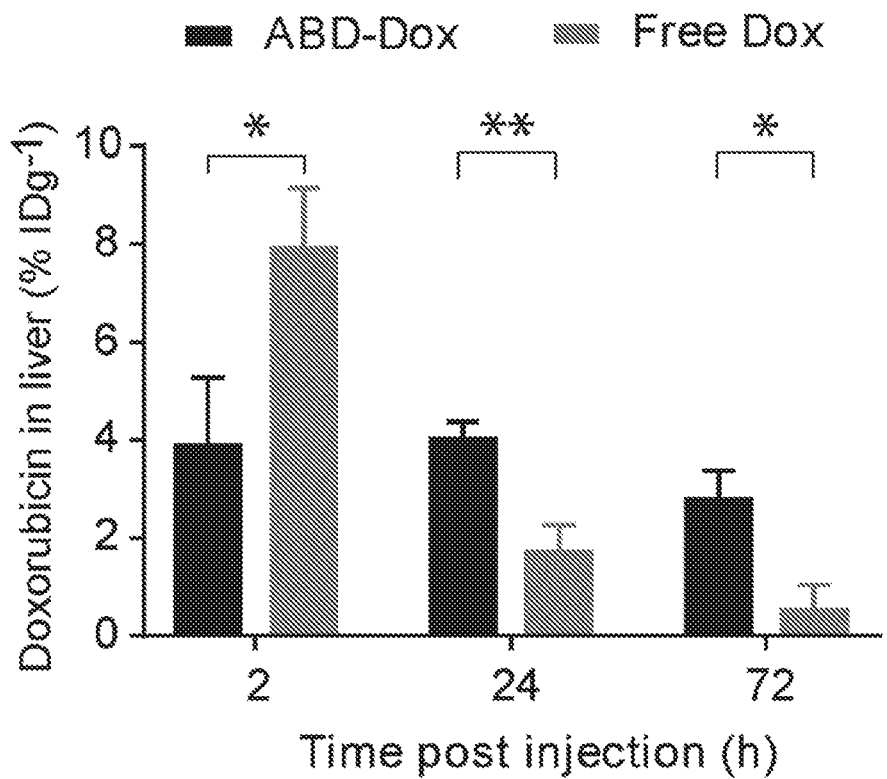
Figure 6D:
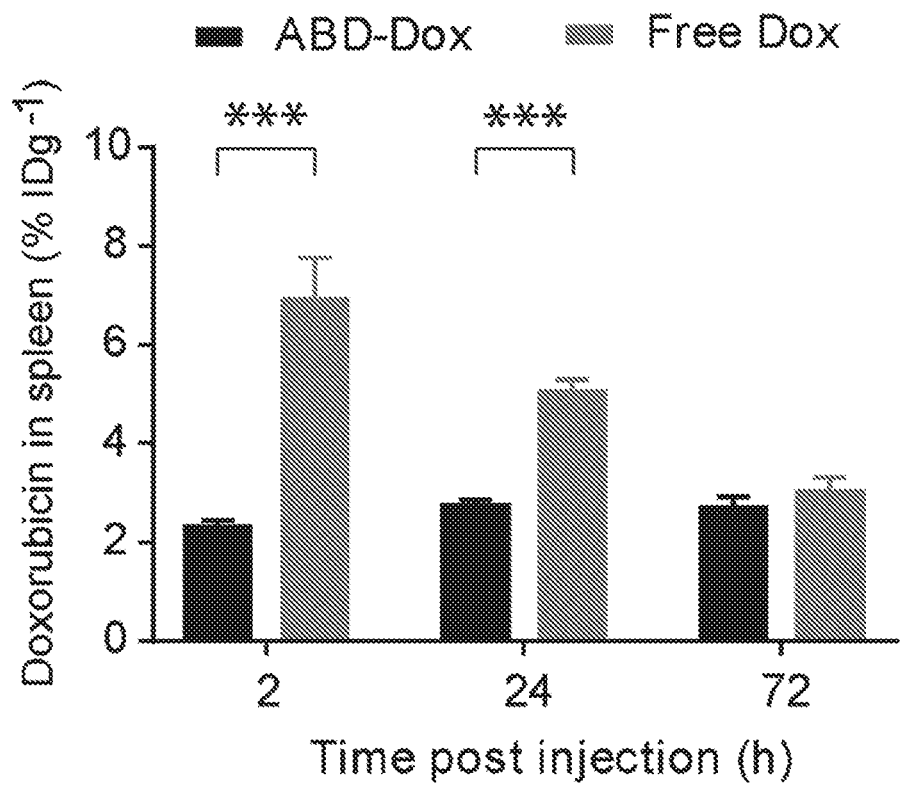
Figure 6E:
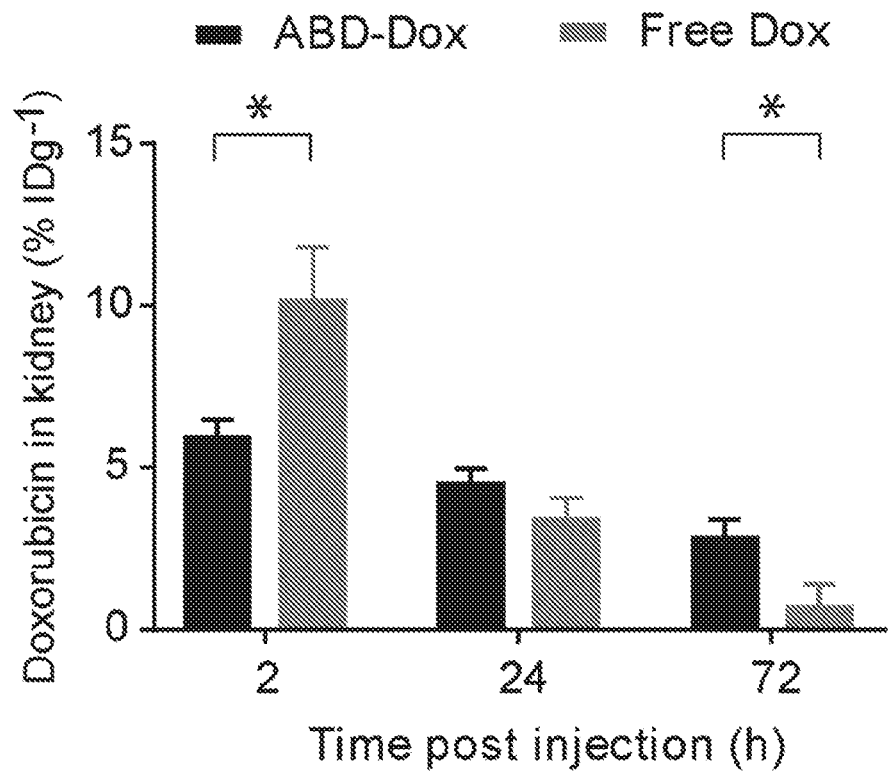
Figure 6F:
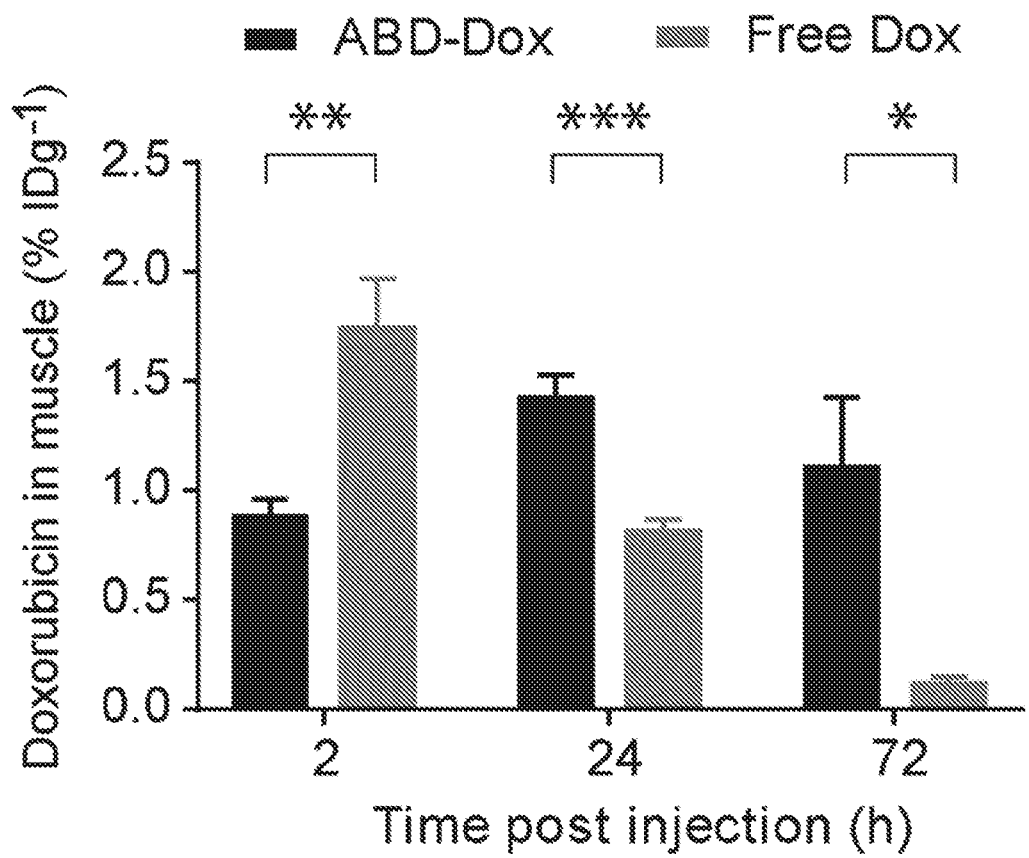

FIG. 6A, FIG. 6B, FIG. 6C, FIG. 6D, FIG. 6E, and FIG. 6F are bar charts showing the biodistribution of ABD-Dox in different tissues. C26 tumor-bearing mice were treated with ABD-Dox at 10 mg Dox Equiv.$kg^{-1}$ BW and free Dox at 10 mg$kg^{-1}$ BW. The Dox concentration was measured in at 2 h, 24 h, and 74 h post-administration in tumor and normal tissues including heart (FIG. 6A), lung (FIG. 6B), liver (FIG. 6C), spleen (FIG. 6D), kidney (FIG. 6E) and muscle (FIG. 6F). Data are presented as mean±SEM, n=5-7, Student's t-test, * P<0.05,  P<0.01, * P<0.001.

Figure 7:
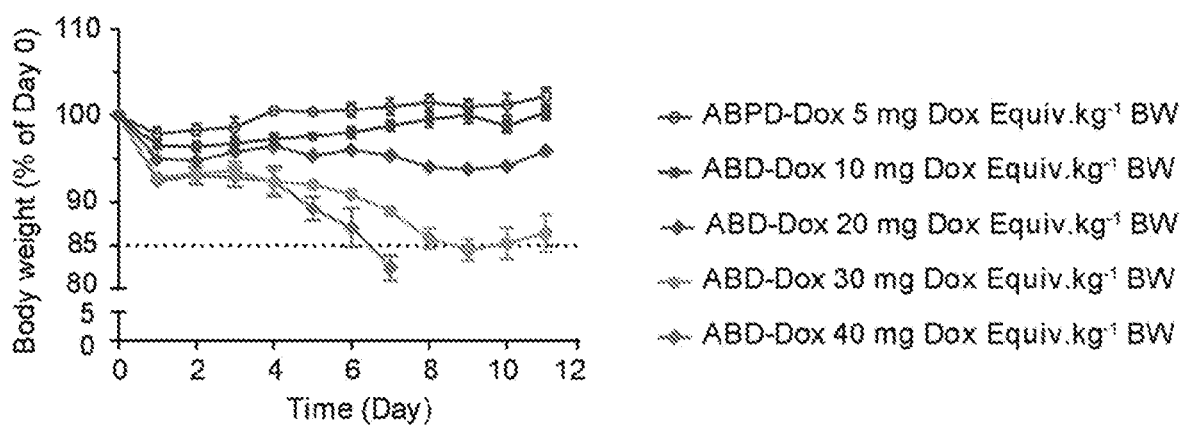

FIG. 7 is a plot showing a dose-escalation study of ABD-Dox. Increasing doses of ABD-Dox were injected i.v. in healthy BALB/c mice and body weight loss was monitored for 2 weeks. Data are presented as mean±SEM, n=4-5.

Figure 8:
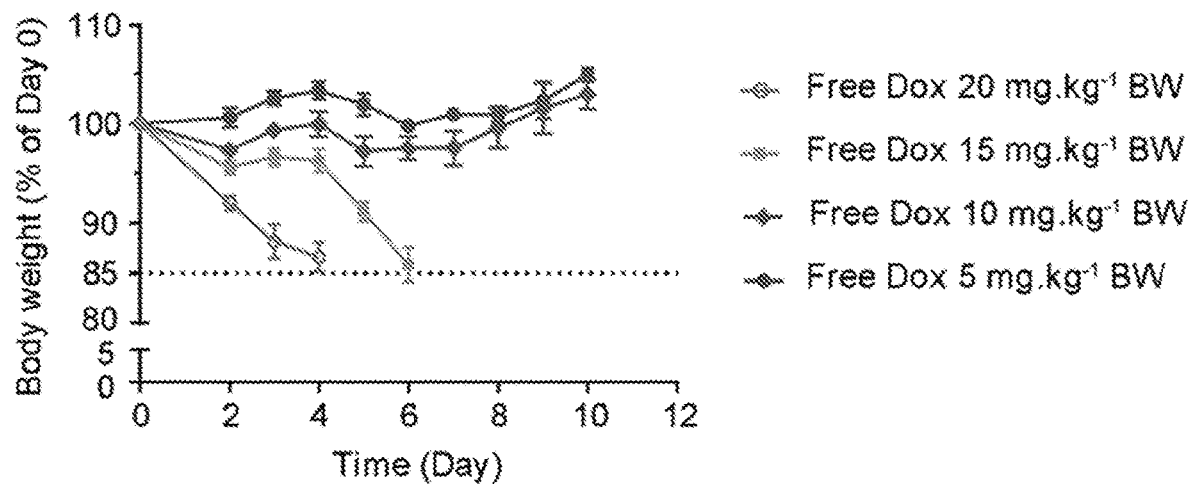

FIG. 8 is a plot showing a dose escalation study of free Dox. Increasing doses of free Dox were injected i.v. in healthy BALB/c mice and body weight loss was monitored for 2 weeks. Data are presented as mean±SEM, n=5.

Figure 9A:
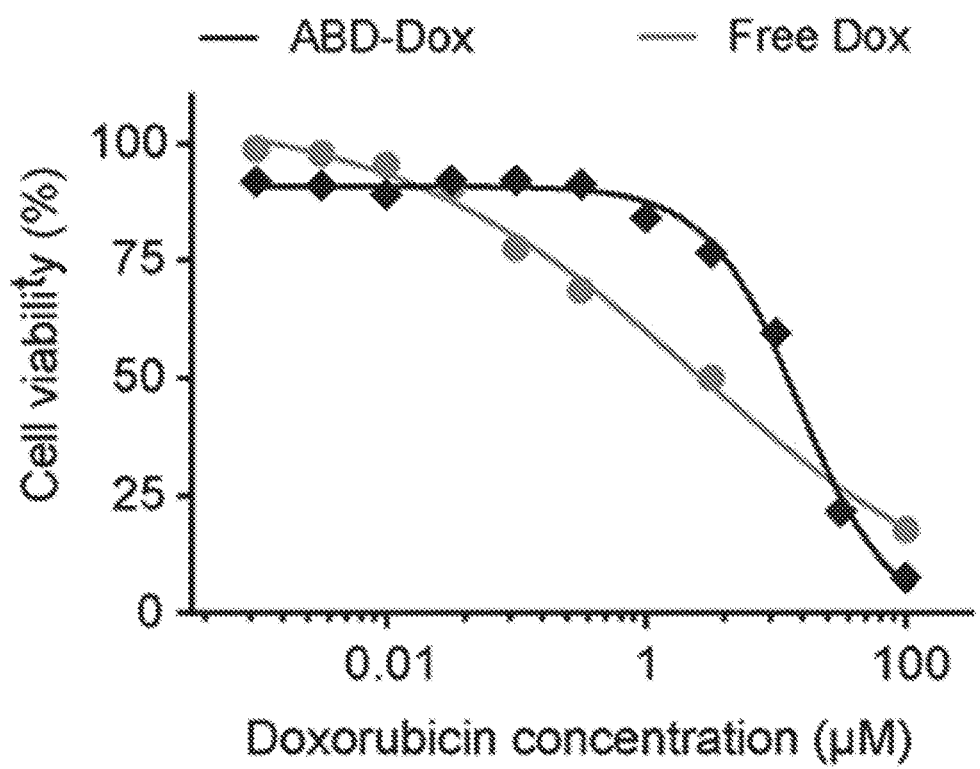
Figure 9B:
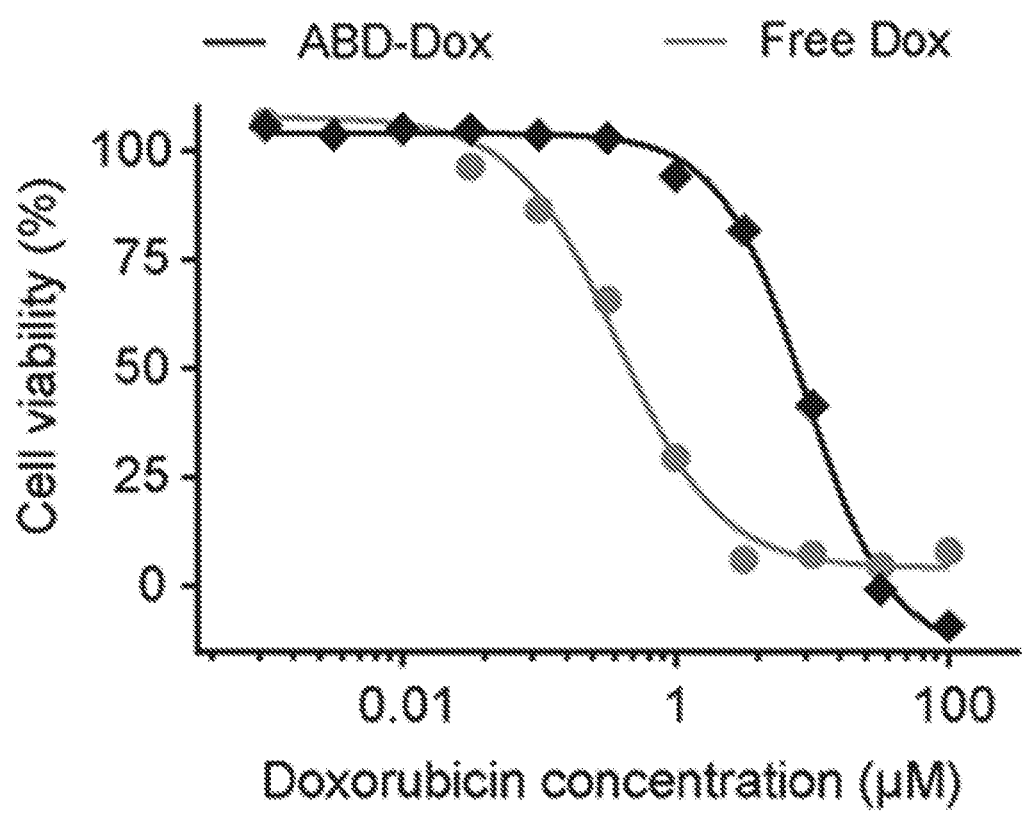

FIG. 9A and FIG. 9B are plots showing the cytotoxicity of ABD-Dox and free Dox against AsPC-1 (FIG. 9A) and BxPC-3 (FIG. 9B) pancreatic cancer cells after 72 h incubation. The $IC_{50}$ of ABD-Dox and free Dox were calculated as 15.2 and 2.5 µM, respectively, for AsPC-1 and as 8.9 and 0.4 µM, respectively, for BxPC-3 cells. Data are presented as mean±SEM, n=3.

Figure 10A:
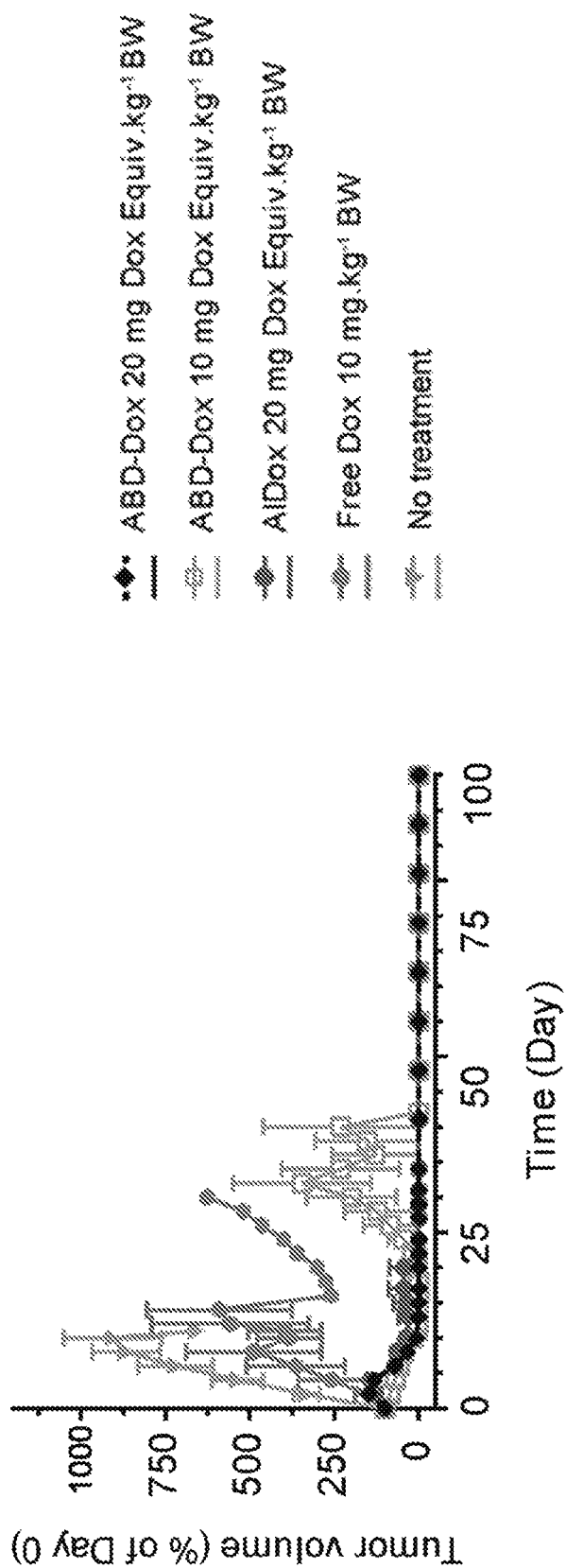
Figure 10B:
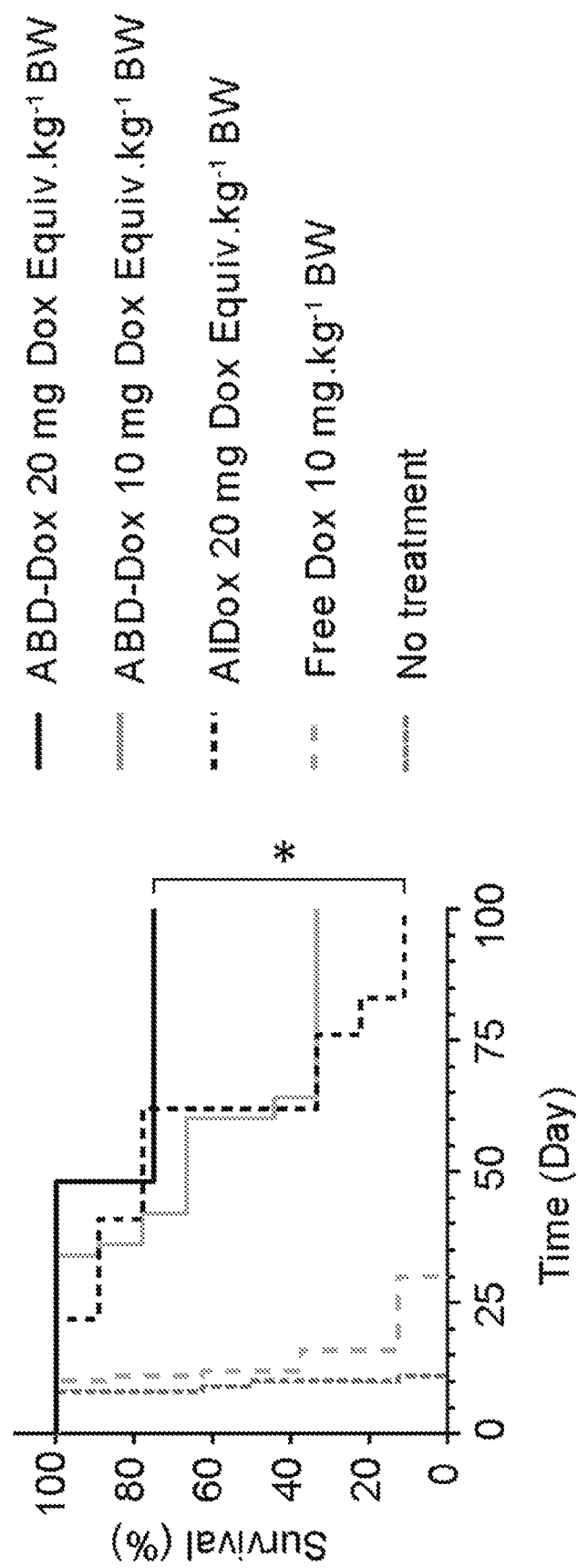
Figure 10C:
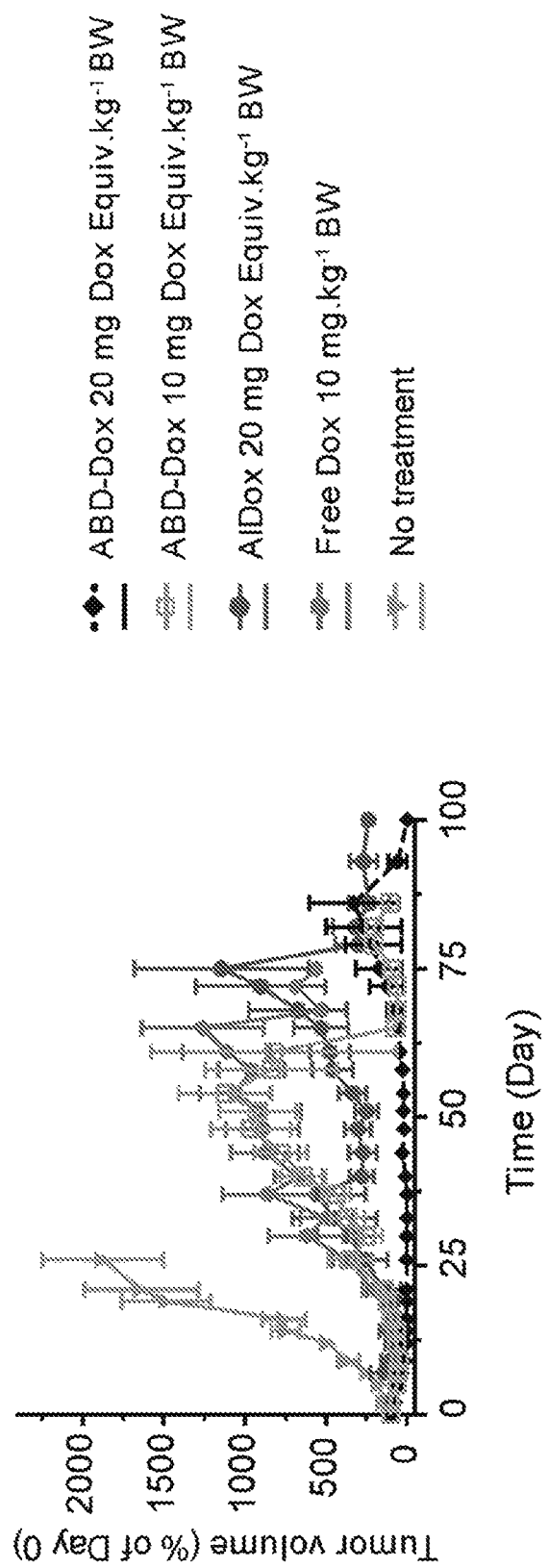
Figure 10D:
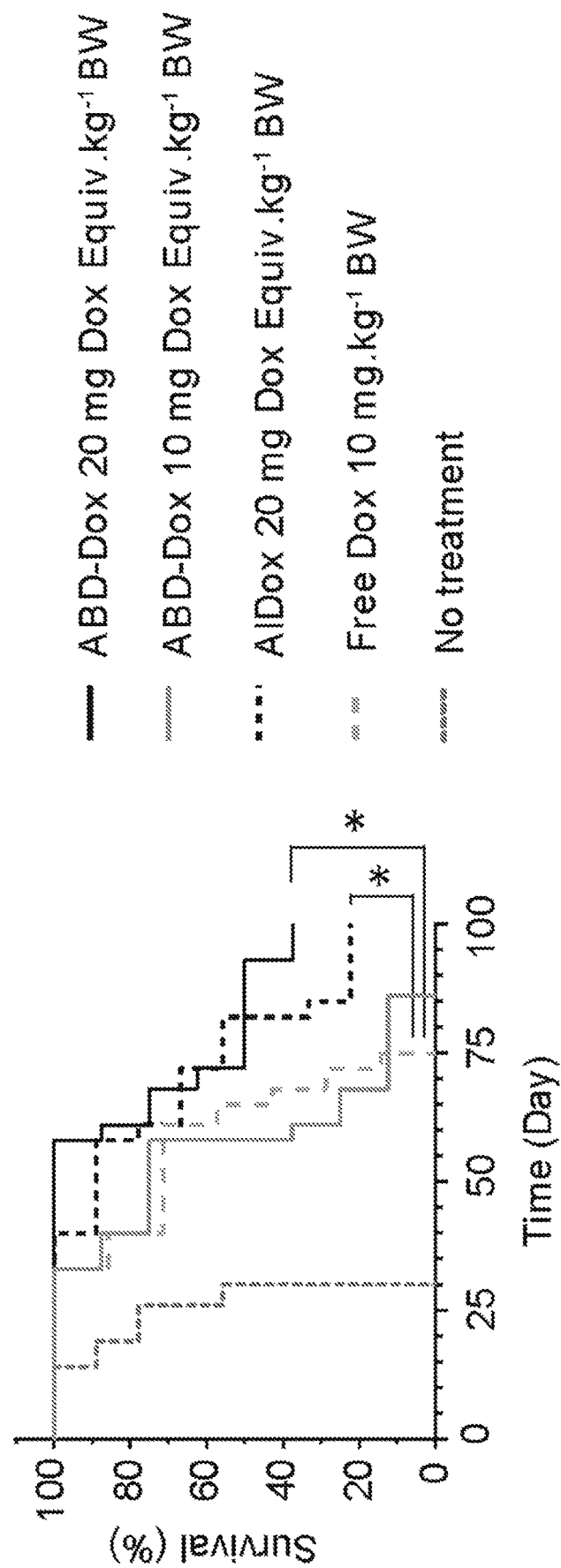
Figure 10E:
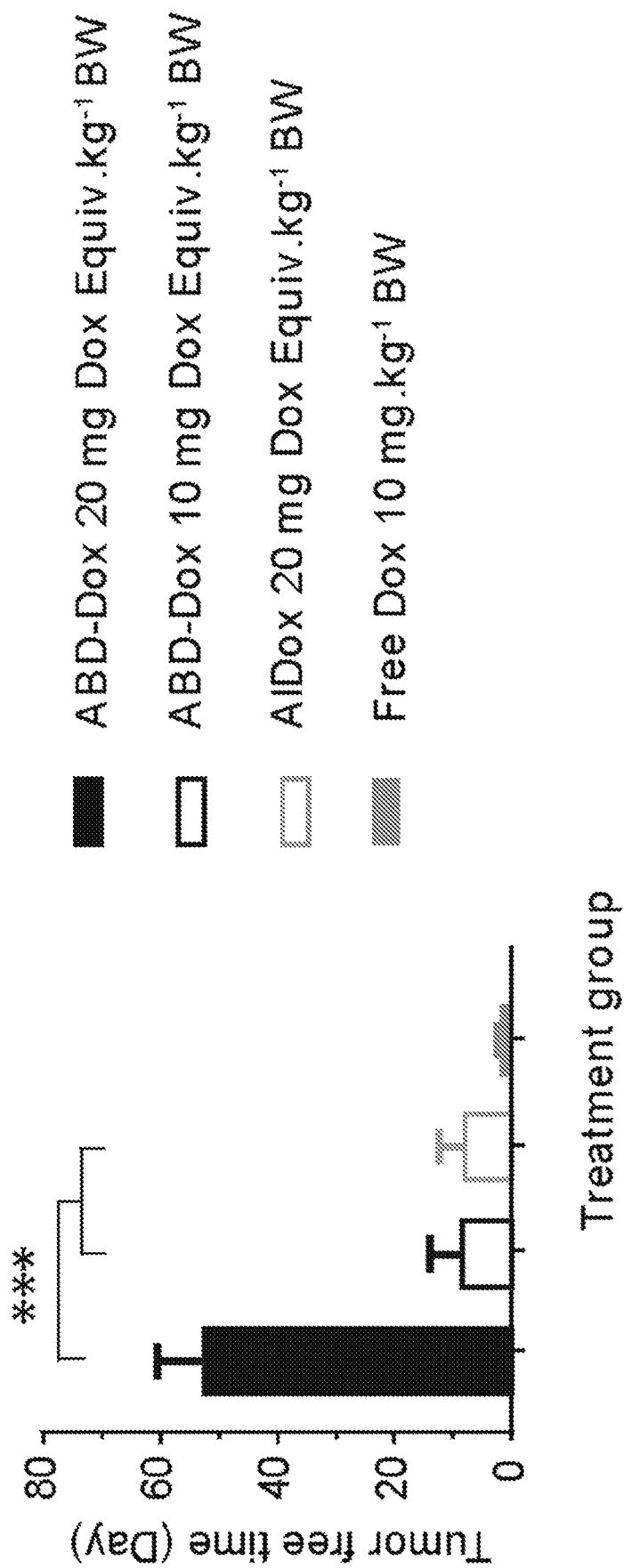

FIG. 10A, FIG. 10B, FIG. 10C, FIG. 10D, and FIG. 10E show the anti-tumor activity of ABD-Dox. BALB/c and nude BALB/c mice bearing syngeneic C26 (FIG. 10A and FIG. 10B) and xenograft MIA PaCa-2 (FIG. 10C, FIG. 10D, and FIG. 10E) tumors, respectively, were treated on day 0 with ABD-Dox (10 and 20 mg Dox Equiv.kg-1 BW), AlDox (20 mg Dox Equiv.kg-1 BW) and free Dox (10 mgkg-1 BW). FIG. 10A and FIG. 10C show tumor volume over 100 days after treatment. FIG. 10B and FIG. 10D show Kaplan-Meier cumulative survival of mice over 100 days post treatment. FIG. 10E shows tumor-free time during the 100-day span after treatment of mice with MIA PaCa-2 xenografts. Data are presented as mean±SEM, n=7-9, FIG. 10A and FIG. 10C: paired one-way ANOVA and Tukey's test, FIG. 10B and FIG. 10D: log-rank (Mantel-Cox) test, FIG. 10E: one-way ANOVA and Tukey's test, * for P<0.05,  for P<0.01, * for P<0.001.

Figure 11:
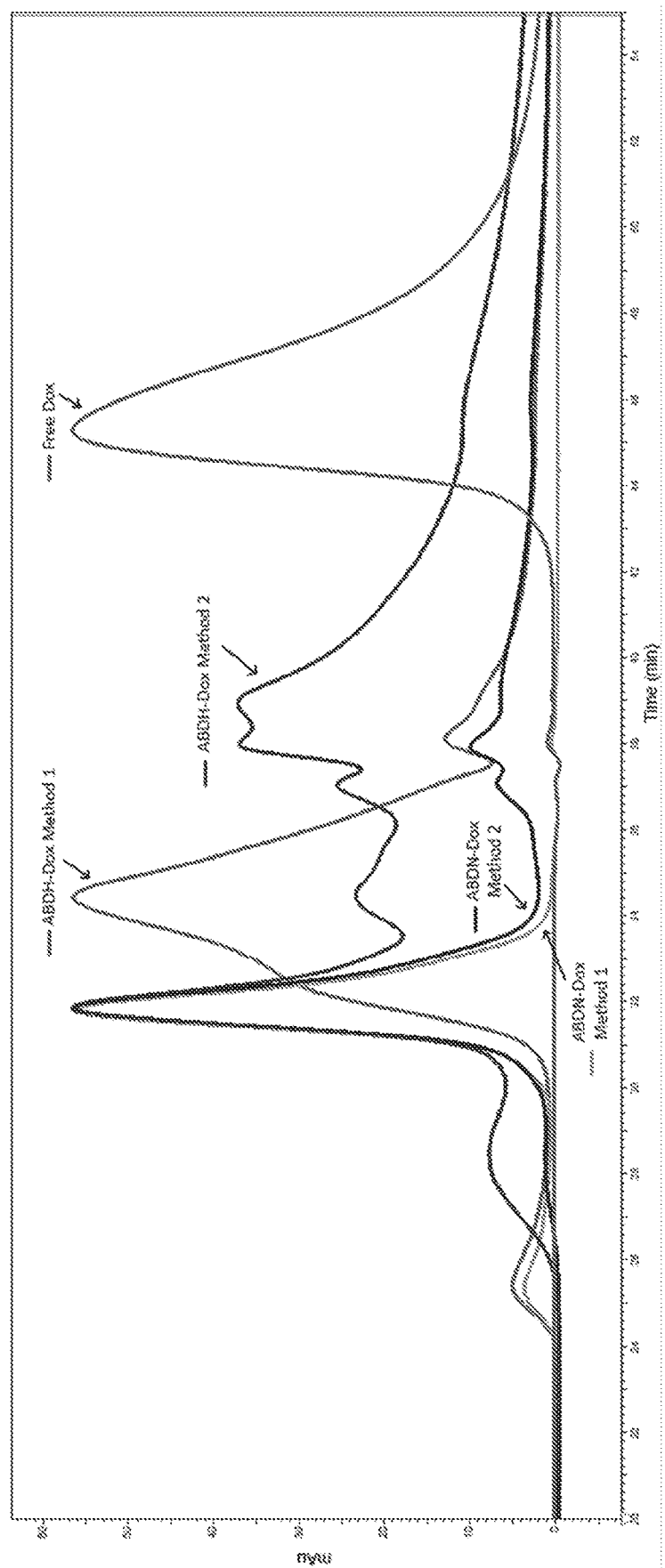

FIG. 11 is a plot showing HPLC chromatograms of ABDN-Dox (M4PL4T3-Dox) and ABDH-Dox (M4PL6T3-Dox) purified by two methods (PostAKTA and PostAmicon).

DETAILED DESCRIPTION OF THE INVENTION

Disclosed herein are compositions for a novel delivery system. The compositions comprise an albumin binding domain, a linker coupled to the albumin binding domain and at least one molecule coupled to the linker. The compositions facilitate binding to albumin upon administration and resulted in improved the pharmacokinetics, biodistribution, and therapeutic efficacy of molecule being delivered. The albumin binding ABD-Dox conjugate exhibited nanomolar affinity for human and mouse serum albumin, and upon in vivo administration in a mouse animal model, had a plasma half-life of 29.4 h, that is close to that of mouse albumin. In addition, 2 h after administration, ABD-Dox had an approximately 4-fold higher concentration in the tumor than free Dox. Free Dox cleared quickly from the tumor, while ABD-Dox maintained a steady concentration in the tumor for at least 72 h, so that the relative accumulation of ABD-Dox at 72 h was ~120-fold greater than that of free Dox. The improved pharmacokinetic and biodistribution profiles of ABD-Dox resulted in enhanced therapeutic efficacy in syngeneic C26 colon carcinoma in BALB/c mice, and in MIA-PaCa2 pancreatic tumor xenografts in nude mice, when compared with free Dox and aldoxorubicin, an albumin-reactive Dox prodrug currently in clinical development, demonstrating its superiority over Dox and aldoxorubicin as a monotherapy agent for cancer therapy.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 1º% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, the terms "administering," "providing" and "introducing" are used interchangeably herein and refer to the placement of the compositions of the disclosure into a subject by a method or route which results in at least partial localization of the composition to a desired site. The compositions can be administered by any appropriate route which results in delivery to a desired location in the subject.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

As used herein, the term "chemotherapeutic" or "anticancer drug" includes any small molecule or other drug used in cancer treatment. Chemotherapeutics include, but are not limited to, cyclophosphamide, methotrexate, 5-fluorouracil, doxorubicin, cyclophosphamide, docetaxel, doxorubicin, daunorubicin, bleomycin, vinblastine, dacarbazine, cisplatin, paclitaxel and docetaxel.

The terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the regenerative cells, the type or extent of supplemental therapy used, ongoing disease process and type of treatment desired (e.g., aggressive vs. conventional treatment).

The term "imaging agent," as used herein, refers to a molecule or compound that can be detected directly or after applying a stimulus. Imaging agents may include luminescent labels which emit radiation on exposure to an external source of radiation or other stimulus, radioactive labels, NMR-active labels, or heavy atoms.

As used herein, the term "octanol-water distribution coefficient" refers to a measure of the degree of hydrophilicity or hydrophobicity of a chemical substance, for example a drug. The measurement is the ratio of the sum of the concentrations of all forms of the compound (ionized plus un-ionized) in each of two immiscible phases, one hydrophobic and one hydrophilic phase, at equilibrium. The measurement is pH dependent, and the aqueous phase is usually buffered to a specific value. The larger the octanol-water distribution coefficient; the more hydrophobic the chemical substance becomes. The small the octanol-water distribution coefficient, the more hydrophilic.

A "peptide" or "polypeptide" is a linked sequence of two or more amino acids linked by peptide bonds. The polypeptide can be natural, synthetic, or a modification or combination of natural and synthetic. Domains are portions of a polypeptide or protein that form a compact unit and are typically 15 to 350 amino acids long.

As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

A "subject" or "patient" may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

As used herein, the term "transition temperature" or "Tt" refers to the temperature at which the material changes from one state to another, for example, soluble to insoluble. For example, below the $T_t$ the conjugate may be highly soluble. Upon heating above the transition temperature, for example, the conjugate may aggregate, forming a separate phase.

As used herein, "treat," "treating" and the like mean a slowing, stopping or reversing of progression of a disease or disorder when provided a composition described herein to an appropriate control subject. The terms also mean a reversing of the progression of such a disease or disorder to a point of eliminating or greatly reducing the cell proliferation. As such, "treating" means an application or administration of the compositions described herein to a subject, where the subject has a disease or a symptom of a disease, where the purpose is to cure, heal, alleviate, relieve, alter, remedy, ameliorate, improve or affect the disease or symptoms of the disease.

2. Albumin Binding Peptide Composition

Provided herein are compositions an albumin binding domain, a linker coupled to the albumin binding domain and at least one molecule coupled to the linker.

a) Albumin Binding Domain

The composition may include an albumin binding domain (ABD). The albumin binding domain binds albumin in vivo or in vitro. The albumin binding domain may be from any animal species, including but not limited to, human and rodent. In some embodiments, the albumin binding domain (ABD) may be a 46 amino acid polypeptide derived from bacterial protein G (ABDN). In some exemplary embodiments, the ABD comprises SEQ ID NO: 1.

In some embodiments, the albumin binding domain (ABD) may be an engineered variant of ABDN. In some embodiments, the albumin binding domain (ABD) may be an engineered variant of ABDN that exhibits different affinity for albumin compared to ABDN. In some embodiments, the albumin binding domain (ABD) may be an engineered variant of ABDN that exhibits higher affinity for albumin compared to ABDN. In some exemplary embodiments, the ABD comprises SEQ ID NO: 2. In some embodiments, the albumin binding domain (ABD) may be a deimmunized ABD variant.

b) Linker

The composition may include a linker. The linker may comprise a cysteine. In some embodiments, the linker comprises an amino acid sequence of $(CGG)_z$ (SEQ ID NO:3), in which z is greater than 1. In some embodiments, z is an integer from 1 to 40, from 1 to 30, from 1 to 20, from 1 to 10, or from 1-5. In some embodiments, z is 4 or 8.

The linker may be attached to the C-terminus or the N-terminus of the ABD. In some embodiments, the linker is attached to the N-terminus of the ABD. In some embodiments, the linker is attached to the C-terminus of the ABD.

c) Molecule

The composition may include a molecule. The molecule may be a chemotherapeutic. Such chemotherapeutic agents are well known in the art and may include, for example, doxorubicin, paclitaxel, gemcitabine, docetaxel, taxol, SN-38, irinotecan and letrozole. In some embodiments, the chemotherapeutic is doxorubicin.

The molecule may be an imaging agent. Imaging agents include luminescent labels which emit radiation on exposure to an external source of radiation or other stimulus, e.g. fluorescent materials or fluorophores, chemiluminescent materials, electroluminescent materials, phosphorescent materials, quantum dots and thermoluminescent materials. Examples of fluorophores include fluoresceins, xanthenes, cyanines, naphthalenes, coumarins, oxadiazoles, pyrenes, oxazines, acridines, arylmethines, Alexa Fluors and tetrapyrroles.

Other imaging agents include radioactive labels, including positron emitting nuclei such as $^{18}F$, $^{64}Cu$ or $^{124}I$ which can be detected by imaging techniques such as positron emission topography (PET). Other radioactive labels such as $^{14}C$, $^{3}H$, or iodine isotopes such as $^{123}I$ and $^{131}I$, which can be detected using autoradiographic analysis or scintillation detection for example, can also be used. Imaging agents may include those which can be detected by magnetic resonance techniques, for example magnetic resonance imaging (MRI) or nuclear magnetic resonance (NMR) detectors, the agents typically comprising one or more NMR-active nuclei that are not generally found in concentrated form elsewhere in the organism or biological sample, for example, $^{13}C$, $^{2}H$ (deuterium) or $^{19}F$. Further imaging agents include those which are effective contrast agents for X-ray photographic techniques or computed tomography (CT) imaging techniques generally comprising atoms with large nuclei, for example atoms with atomic number of 35 or more, preferably 40 or more and even more preferably 50 or more, for example iodine or barium.

The molecule may be relatively hydrophobic or hydrophilic. In some embodiments, the molecule may have an octanol-water distribution coefficient (log D) of greater than or equal to 1.5 at a pH of 7.4 when the molecule is not attached to the ABD.

The composition may include varying amounts of the molecule. In some embodiments, the composition may include at least one molecule. In some embodiments, the composition may include at least two molecules. In some embodiments, the composition includes one or two molecules.

In some embodiments, the molecule is coupled to a cysteine in the linker. In some embodiments, the molecule is coupled to the linker through a thiol group. The thiol group may react with many chemical groups known in the art including, but not limited to, haloacetyls, maleimides, hydrazides, aziridines and acryloyls. In some embodiments, the molecule is coupled to a cysteine in the linker with a hydrazide.

In some embodiments, the molecule is attached to the linker through a pH labile bond. The bond may be acid labile, such that the bond is broken at lower pH values. The bond may be base labile, such that the bond is broken at higher pH values. In some embodiments, the molecule is attached to the linker through a hydrazone bond.

3. Method of Purifying the Albumin Binding Peptide Composition

Provided herein are methods of purifying the albumin binding peptide compositions described herein. The method may include forming a conjugate comprising an elastin-like polypeptide having a transition temperature ($T_t$) above 50° C. and the albumin binding peptide composition described herein, wherein the composition is conjugated to a first end of the elastin-like polypeptide by an amino acid sequence amenable to cleavage, treating the conjugate with an enzyme, chemical or combination thereof capable of cleaving the amino acid sequence amenable to cleavage, and separating the composition from the elastin-like polypeptide.

a) Forming a Conjugate

The method may include forming a conjugate comprising an elastin-like polypeptide having a transition temperature ($T_t$) above 50° C. and the composition described herein ("albumin binding peptide composition"), wherein the composition is conjugated to a first end of the elastin-like polypeptide by an amino acid sequence amenable to cleavage. The composition may be conjugated to the N-terminus or the C-terminus of the elastin-like polypeptide.

i. Elastin-Like Polypeptide

Elastin-like polypeptides (ELP) are one example of thermally responsive polypeptides. Other thermally responsive polypeptides may be equally useful in this method. In some embodiments, the elastin-like polypeptide comprises an amino acid sequence of $(VPGXaaG)_p$(SEQ ID NO:4), wherein Xaa is any amino acid except proline and p is an integer from 1 to 500. In some embodiments, Xaa is alanine. P may be from 1 to 100, from 1 to 200, from 1 to 300, from 1 to 400, from 100 to 200, from 100 to 300, from 100 to 400, from 100 to 500, from 200 to 300, from 200 to 400, from 200 to 500, from 300 to 400, from 300 to 500, or from 400 to 500. In some embodiments, p is 160.

ii. Albumin Binding Peptide Composition

The composition may include an albumin binding domain, a linker coupled to the albumin binding domain and at least one molecule coupled to the linker.

The albumin binding domain may be from any animal species, including but not limited to, human and rodent. In some embodiments, the albumin binding domain (ABD) may be a 46 amino acid polypeptide derived from bacterial protein G (ABDN). In some exemplary embodiments, the ABD comprises SEQ ID NO: 1.

In some embodiments, the albumin binding domain (ABD) may be an engineered variant of ABDN. In some embodiments, the albumin binding domain (ABD) may be an engineered variant of ABDN that exhibits different affinity for albumin compared to ABDN. In some embodiments, the albumin binding domain (ABD) may be an engineered variant of ABDN that exhibits higher affinity for albumin compared to ABDN. In some exemplary embodiments, the ABD comprises SEQ ID NO: 2.

The composition may include a linker. The linker may comprise a cysteine. In some embodiments, the linker comprises an amino acid sequence of $(CGG)_z$ (SEQ ID NO:3), in which z is greater than 1. In some embodiments, z is an integer from 1 to 40, from 1 to 30, from 1 to 20, from 1 to 10, or from 1-5. In some embodiments, z is 4 or 8.

The linker may be attached to the C-terminus or the N-terminus of the ABD. In some embodiments, the linker is attached to the N-terminus of the ABD. In some embodiments, the linker is attached to the C-terminus of the ABD.

The composition may include a molecule. The molecule may be a chemotherapeutic. Such chemotherapeutic agents are well known in the art and may include, for example, doxorubicin, paclitaxel, gemcitabine, docetaxel, taxol, SN-38, irinotecan and letrozole. In some embodiments, the chemotherapeutic is doxorubicin.

The molecule may be an imaging agent. Imaging agents include luminescent labels which emit radiation on exposure to an external source of radiation or other stimulus, e.g. fluorescent materials or fluorophores, chemiluminescent materials, electroluminescent materials, phosphorescent materials, quantum dots and thermoluminescent materials. Examples of fluorophores include fluoresceins, xanthenes, cyanines, naphthalenes, coumarins, oxadiazoles, pyrenes, oxazines, acridines, arylmethines, Alexa Fluors and tetrapyrroles.

Other imaging agents include radioactive labels, including positron emitting nuclei such as $^{18}F$, $^{64}Cu$ or $^{124}I$ which can be detected by imaging techniques such as positron emission topography (PET). Other radioactive labels such as $^{14}C$, $^{3}H$, or iodine isotopes such as $^{123}I$ and $^{131}I$, which can be detected using autoradiographic analysis or scintillation detection for example, can also be used. Imaging agents may include those which can be detected by magnetic resonance techniques, for example magnetic resonance imaging (MRI) or nuclear magnetic resonance (NMR) detectors, the agents typically comprising one or more NMR-active nuclei that are not generally found in concentrated form elsewhere in the organism or biological sample, for example, $^{13}C$, $^{2}H$ (deuterium) or $^{19}F$. Further imaging agents include those which are effective contrast agents for X-ray photographic techniques or computed tomography (CT) imaging techniques generally comprising atoms with large nuclei, for example atoms with atomic number of 35 or more, preferably 40 or more and even more preferably 50 or more, for example iodine or barium.

The molecule may be relatively hydrophobic or hydrophilic. In some embodiments, the molecule may have an octanol-water distribution coefficient (log D) of greater than or equal to 1.5 at a pH of 7.4 when the molecule is not attached to the ABD.

The albumin binding peptide composition may include varying amounts of the molecule. In some embodiments, the composition may include at least ne molecule. In some embodiments, the composition may include at least two molecules. In some embodiments, the composition includes one or two molecules.

In some embodiments, the molecule is coupled to a cysteine in the linker. In some embodiments, the molecule is coupled to the linker through a thiol group. The thiol group may react with many chemical groups known in the art including, but not limited to, haloacetyls, maleimides, hydrazides, aziridines and acryloyls. In some embodiments, the molecule is coupled to a cysteine in the linker with a hydrazide.

In some embodiments, the molecule is attached to the linker through a pH labile bond. The bond may be acid labile, such that the bond is broken at lower pH values. The bond may be base labile, such that the bond is broken at higher pH values. In some embodiments, the molecule is attached to the linker through a hydrazone bond.

iii. Destabilizing Peptide

A destabilizing peptide may be conjugated to a second end of the elastin-like polypeptide. The destabilizing peptide may be conjugated to the N-terminus or the C-terminus of the elastin-like polypeptide. The destabilizing peptide may be conjugated on the opposite end of elastin-like polypeptide from the composition.

The destabilizing peptide functions to alter the ability of the elastin-like polypeptide to form a micellar arrangement. Without a destabilizing sequence, the ELP forms micelles and hampers enzymatic step in the method. However, with a destabilizing sequence that prevents micelle formation of the conjugate, the enzymatic step may be much more efficient, thereby increasing purification yield.

In some embodiments, the destabilizing peptide comprises a tetrapeptide with an amino acid sequence of KEKE (SEQ ID NO: 5).

b) Treating the Conjugate

The method may include treating the conjugate with an enzyme, chemical, or combination thereof capable of cleaving the amino acid sequence amenable to cleavage.

In some embodiments, the amino acid sequence is amenable to cleavage by an enzyme. Any of the amino acid sequence/enzyme or amino acid sequence/chemical pairs known in the art to be capable of site directed cleavage of a peptide strand may be used. The enzyme may be an endoprotease, including, for example, the enzymes enterokinase, Factor Xa, HRV3C protease, TEV Protease and Thrombin with their respective known peptide cleavage sequences.

In some embodiments, the amino acid sequence is amenable to cleavage by a chemical. The chemicals may include hydroxylamine, and cyanogen bromide with their respective known peptide cleavage sequences, for example, those which contain an asparagine-glycine peptide bonds and those with a peptide bond at the C-terminus of methionine residues, respectively.

The amino acid sequence may be cleaved by a Sortase enzyme. Sortase enzymes generally cleave sequences represented by the pentapeptide LPX$^1$TG (SEQ ID NO: 8), wherein X$^1$ is any amino acid. In such sequences, the enzyme cleaves between the T and the G. In some embodiments, the amino acid sequence is amenable to cleavage by an enzyme wherein the enzyme is Sortase A. In some embodiments, the amino acid sequence amenable to enzymatic cleavage includes a pentapeptide with an amino acid sequences of LPETG (SEQ ID NO: 6).

c) Separating the Composition from the Elastin-Like Polypeptide

The method may include separating the composition from the elastin-like polypeptide. The composition may be separated from the elastin-like polypeptide use methods known in the art including, for example, affinity, filtration, and chromatographic techniques. These techniques may be based on differences in chemical and physical properties between the composition and the elastin-like polypeptide, including charge, affinity to a binding partner, including exogenous affinity tags, size, or relative hydrophobicity. In some embodiments, the separation includes size-exclusion chromatography, filtration or ultracentrifugation.

4. Methods of Use a) Method of Killing Cancer Cells

The present disclosure also provides a method of killing multiple cancer cells. The method may include contacting multiple cancer cells with the composition as detailed herein to the subject. The cancer cells may be in an in vitro environment or an in vivo environment. In some embodiments, the cancer cells are in a subject. Many different types of cancer cells may be killed by chemotherapeutics. The compositions as detailed herein may be used to deliver chemotherapeutics to any cancer cell type.

b) Method of Treating a Disease or Disorder

The present disclosure also provides methods of treating a disease or disorder. The methods comprise administering an effective amount of the composition as detailed herein to the subject.

In some embodiments, the disease or disorder is cancer. Many different cancer types and subtypes may be treated by chemotherapeutics. The compositions as detailed herein may be used to deliver chemotherapeutics to any cancer type or subtype. In some embodiments, the cancer may be a carcinoma, sarcoma, lymphoma, leukemia, melanoma, mesothelioma, multiple myeloma, or seminoma. The cancer may be a cancer of the bladder, blood, bone, brain, breast, cervix, colon/rectum, endometrium, head and neck, kidney, liver, lung, muscle tissue, ovary, pancreas, prostate, skin, spleen, stomach, testicle, thyroid or uterus.

The disease or disorder may be a cancer comprising solid tumors. Examples of cancers that comprise solid tumors include, but are not limited to, pancreatic, bladder, non-small cell lung cancer (NSCLC), breast and ovarian cancers.

5. Administration

The disclosed compositions may be incorporated into pharmaceutical compositions suitable for administration to a subject (such as a patient, which may be a human or non-human) well known to those skilled in the pharmaceutical art. The pharmaceutical composition may be prepared for administration to a subject. Such pharmaceutical compositions can be administered in dosages and by techniques well known to those skilled in the medical arts taking into consideration such factors as the age, sex, weight, and condition of the particular subject, and the route of administration.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator. The route by which the composition is administered and the form of the composition will dictate the type of carrier to be used.

The composition can be administered prophylactically or therapeutically. In prophylactic administration, the composition can be administered in an amount sufficient to induce a response. In therapeutic applications, the composition is administered to a subject in need thereof in an amount sufficient to elicit a therapeutic effect. An amount adequate to accomplish this is defined as "therapeutically effective dose." Amounts effective for this use will depend on, e.g., the particular composition of the conjugate regimen administered, the manner of administration, the stage and severity of the disease, the general state of health of the patient, and the judgment of the prescribing physician.

The compositions can be administered by methods well known in the art as described in Donnelly et al. (*Ann. Rev. Immunol.* 1997, 15, 617-648); Felgner et al. (U.S. Pat. No. 5,580,859, issued Dec. 3, 1996); Feigner (U.S. Pat. No. 5,703,055, issued Dec. 30, 1997); and Carson et al. (U.S. Pat. No. 5,679,647, issued Oct. 21, 1997). One skilled in the art would know that the choice of a pharmaceutically acceptable carrier, including a physiologically acceptable compound, depends, for example, on the route of administration.

The compositions can be delivered via a variety of routes. Typical delivery routes include parenteral administration, e.g., intradermal, intramuscular or subcutaneous delivery. Other routes include oral administration, intranasal, intravaginal, transdermal, intravenous, intraarterial, intratumoral, intraperitoneal, and epidermal routes. In some embodiments, the conjugate is administered intravenously, intraarterially, or intraperitoneally to the subject.

The composition may conveniently be presented in a single dose or as divided doses administered at appropriate intervals, for example, as two, three, four or more sub-doses per day. The sub-dose itself may be further divided, e.g., into a number of discrete loosely spaced administrations.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials, in vivo studies and in vitro studies.

Dosage amount and interval may be adjusted individually to provide plasma levels of the molecule which are sufficient to maintain the modulating effects, or minimal effective concentration (MEC). The MEC will vary for each molecule but can be estimated from in vivo and/or in vitro data. Dosages necessary to achieve the MEC will depend on individual characteristics and route of administration. However, assays well known to those in the art can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the symptoms to be treated and the route of administration. Further, the dose, and perhaps dose frequency, will also vary according to the age, body weight, and response of the individual patient. A program comparable to that discussed above may be used in veterinary medicine.

A therapeutically effective amount of the composition disclosed herein may be administered alone or in combination with a therapeutically effective amount of at least one additional therapeutic agents. In some embodiments, effective combination therapy is achieved with a single composition or pharmacological formulation that includes both agents, or with two distinct compositions or formulations, administered at the same time, wherein one composition includes a compound of this invention, and the other includes the second agent(s). Alternatively, in other embodiments, the therapy precedes or follows the other agent treatment by intervals ranging from minutes to months.

A wide range of second therapies may be used in conjunction with the compounds of the present disclosure. The second therapy may be a combination of a second therapeutic agent or may be a second therapy not connected to administration of another agent. Such second therapies include, but are not limited to, surgery, immunotherapy, radiotherapy, or a second chemotherapeutic agent.

6. EXAMPLES

It will be readily apparent to those skilled in the art that other suitable modifications and adaptations of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

Example 1: Materials and Methods pET24+ plasmid was purchased from Novagen (Madison, WI). Oligodeoxynucleotides and gBlocks encoding sequences of interest were purchased from Integrated DNA Technologies (Coralville, IA). BL21(DE3) and EB5a chemically competent *E. coli* cells, and all molecular biology enzymes were purchased from New England Biolabs (Ipswich, MA). DNA extraction kits, DNA gel purification kits, and PCR purification kits were purchased from Qiagen (Germantown, MD). Phosphate buffered saline (PBS) tablets were purchased from EMD Millipore (Billerica, MA). All *E. coli* cultures were grown in 2×YT media, comprised of 16 gL-1 of tryptone (Becton, Dickinson and Co., Franklin Lakes, NJ), 10 gL-1 of yeast extract (Becton, Dickinson and Co., Franklin Lakes, NJ), and 5 gL-1 of NaCl (Alfa Aesar, Ward Hill, MA), with 1 μLmL-1 kanamycin sulfate (EMD Millipore, Billerica, MA). Isopropyl-beta-d-thiogalactoside (IPTG) was purchased from Gold Biotechnology (St. Louis, MO). Doxorubicin.HCl was purchased from Carbosynth LLC (San Diego, CA). Aldoxorubicin was purchased from MedKoo Biosciences (Morrisville, NC). Protein molecular weight marker (Precision Plus Protein unstained standards) and AnykD™ TGX Stain-free gels, and Laemmli's sample buffer were purchased from Bio-Rad Laboratories (Hercules, CA). SimplyBlue stain solution was purchased from Invitrogen (Carlsbad, CA). Tris(2-carboxyethyl)phosphine (TCEP) hydrochloride and HisPur cobalt spin columns were purchased from Thermo Fisher Scientific (Waltham, MA). N-(ε-maleimidocaproic acid) hydrazide, trifluoroacetic acid salt (EMCH), anhydrous methanol, Amicon Ultra-15 Amicon ultrafiltration spin columns (3 kDa and 10 kDa MWCO), mouse and human serum albumin (MSA/HSA) were purchased from Sigma-Aldrich (St. Louis, MO). All salts used for the preparation of sortase reaction buffer (50 mM Tris, 150 mM NaCl, 10 mM CaCl2, pH 7.5), conjugation buffer (0.1 M Na—PO4, 1 mM EDTA, 3 mM TCEP-HC, pH 7.0), SDS-PAGE running buffer (25 mM Tris, 192 mM glycine, 0.1% SDS, pH 8.3), and native-PAGE running buffer (25 mM Tris, 192 mM glycine, 0.1% SDS, pH 8.3), were purchased from Alfa Aesar (Ward Hill, MA). CellTiter-96® aqueous cell proliferation assay containing 3-(4,5-dimethythiozol-2-yl)-5-(3-carboxymeth oxyphenyl)-2-(4-sulfophenyl)-2H-tetrazolium (MTS) reagent was purchased from Promega (Madison WI). 96-well plates and 75- and 150-cm2 tissue culture flasks were purchased from Corning Inc. (Corning, NY). The C26 cell line was provided by Dr. Francis C. Szoka (University of California, San Francisco) and the BxPC-3, AsPC-1, and MIA PaCa-2 cell lines were purchased from the Duke University Cell Culture Facility (Durham, NC). C26 cells were cultured in RPMI-1640 supplemented with 10% fetal bovine serum, 4.5 g L−1 D-glucose (all from Sigma, St. Louis, MO), 10 mM HEPES, 1 mM sodium pyruvate (both from Invitrogen, Carlsbad, CA), and 100 UmL-1 penicillin-streptomycin (Gibco, Grand Island, NY). MIA PaCa-2 cells were cultured in Dulbecco's Modified Eagle's Medium supplemented with 10% fetal bovine serum, 2.5% horse serum (Sigma, St. Louis, MO), and 100 UmL-1 penicillin-streptomycin. BALB/c mice (5-6 weeks, female) and BALB/c athymic nude mice (nu/nu, 5-6 week, male) were purchased from Charles River Laboratories (Wilmington, MA) and Duke University Cancer Center Isolation facility (Durham, NC), respectively.

Gene synthesis and expression EB5α competent cells were used for cloning and gene assembly. Genes encoding KEKE-ELP$_{160}$-srt-ABD-(CGG)$_{4/8}$ and (His)$_6$-sortase A-ELP$_{40}$ fusions were assembled together by recursive directional ligation by plasmid reconstruction (PRe-RDL)[81] and inserted into a modified pET24+ plasmid, as described elsewhere. For protein expression, plasmids encoding the genes of interest were transformed into BL21(DE3) competent cells and were expressed in 2×YT media. 50 mL of the media was inoculated with frozen DMSO bacterial stock and were grown overnight. Cultures were then inoculated in 1 L 2×YT media and were incubated for 6-8 h at 37° C. and 200 rpm, following which IPTG was added at 1 mM final concentration and the culture was incubated for an additional 10 h. Cells were harvested by centrifugation at 4° C. and 3400 rcf for 15 min, and were resuspended in PBS.

Two different ABD were used; ABDN and ABDH. The amino acid sequence of ABDN is LAEAKVLAN-RELDKYGVSDYYKNLINNAKTVEGVKALIDEI-LAALP (SEQ ID NO:1). The amino acid sequence of ABDH is LAEAKVLAN-RELDKYGVSDFYKRLINKAKTVEGVEALKLHI-LAALP (SEQ ID NO:2).

Protein purification KEKE-ELP$_{160}$-srt-ABD-(CGG)$_4$, KEKE-ELP$_{160}$-srt-ABD-(CGG)$_8$ and (His)$_6$-sortase A-ELP$_{40}$ fusions were purified by inverse transition cycling (ITC) and immobilized metal affinity chromatography (IMAC), respectively. Cells were lysed by sonication (Q500 sonicator; QSonica, Newtown, CT) with 10 s on and 40 s off pulse for a total of 3 min. Nucleic acids and other negatively charged cellular debris were precipitated by addition of 2 mL of 20% v/v polyethyleneimine (PEI) per liter culture and removed by centrifugation at 24,000 rcf for 15 min at 4° C. The KEKE-ELP$_{160}$-srt-ABD-(CGG)$_{4/8}$ constructs were then purified from the supernatant using two cycles of ITC, as described elsewhere with slight modifications. Briefly, ELP$_{160}$-ABD went through multiple "bakeout" cycles consisting of 10 min incubation at 60° C. to transition the ELP$_{160}$-ABD fusion and precipitate contaminant proteins, 10 min incubation on ice to resolubilize the KEKE-ELP$_{160}$-srt-ABD-(CGG)$_{4/8}$ constructs, and 10-min centrifugation at 24,000 rcf and 4° C. ("cold spin") to remove the insoluble contaminants. The KEKE-ELP$_{160}$-srt-ABD-(CGG)$_{4/8}$ were then aggregated by adding NaCl to a final concentration of 2.5 M and centrifugation at 24,000 rcf for 10 min at 35° C. ("hot spin"). The pellet was resuspended in 30 mM TCEP, pH 7 followed by one more cold spin to complete the first ITC cycle. The second ITC cycle was carried out similarly to the first one but using NaCl at 0.5 M final concentration for the hot spin. (His)$_6$-sortase A-ELP$_{40}$ was purified from the clear supernatant, after PEI precipitation of DNA and centrifugation, using HisPur cobalt IMAC spin columns according to the manufacturer's instructions. Briefly, supernatant was added to the columns and was incubated for 1 h at 4° C. Impurities were removed by washing the resin multiple times with PBS. (His)$_6$-sortase A-ELP$_{40}$ was then eluted by addition of PBS with 150 mM imidazole and dialyzed against sortase reaction buffer. SDS-PAGE analysis was performed to confirm the expression and purity of the fusions. 30 µg of proteins were diluted in Laemmli's buffer, heated for 10 min at 95° C., chilled on ice, loaded onto a stain-free gel and run at 200V using SDS-PAGE buffer following which the gel was UV-activated and imaged using the Gel Doc imaging system (Bio-Rad, Hercules, CA).

ABD-Dox synthesis Doxorubicin (Dox) was conjugated to cysteine residues at the C-terminus of the KEKE-ELP$_{160}$-srt-ABD-(CGG)$_4$ and KEKE-ELP$_{160}$-srt-ABD-(CGG)$_8$ via a pH-sensitive hydrazone bond in a two-step reaction. In the first step, Dox (4.25 M) was reacted with EMCH (3.4 M) in anhydrous methanol supplemented with 0.1% (v/v) TFA with stirring at room temperature for 16 h. The activated Dox-EMCH conjugate was concentrated to 17 M by rotary evaporation and was added dropwise to the ABD-ELP fusion (1.7 M) in conjugation buffer with a methanol:buffer volume ratio of 2:1. The reaction mixture was stirred for 24 h at room temperature. Unreacted Dox was removed using 10 kDa MWCO Amicon ultrafiltration spin columns and with PBS:acetonitrile (70:30 v/v) as the eluent. The purified ELP$_{160}$-ABD-Dox was then buffer exchanged using 10 kDa MWCO Amicon ultrafiltration spin columns into sortase reaction buffer in preparation for sortase-catalyzed cleavage of the ELP$_{160}$ tag. To calculate the conjugation efficiency, a small fraction of KEKE-ELP$_{160}$-srt-ABD-Dox was buffer exchanged into Milli-Q water, lyophilized, weighed and dissolved in PBS. The conjugation efficiency was defined as the number of Dox molecules per KEKE-ELP$_{160}$-srt-ABD molecule, and was determined by measuring the concentration of the KEKE-ELP$_{160}$-srt-ABD by gravimetry of the lyophilized conjugate, and that of Dox by spectrophotometry. Following drug conjugation, the ELP$_{160}$ tag was removed by cleavage with the (His)$_6$-sortase A-ELP$_{40}$ fusion. KEKE-ELP$_{160}$-srt-ABD-Dox was mixed with (His)$_6$-sortase A-ELP$_4$ in the presence of triglycine at a KEKE-ELP$_{160}$-srt-ABD-Dox:(His)$_6$-sortase A-ELP$_{40}$:GGG molar ratio of 1:5:250, and final KEKE-ELP$_{160}$-srt-ABD-Dox concentration of 500 µM. The reaction solution was incubated for 24 h at room temperature in the dark, following which the ABD-Dox product was purified from (His)$_6$-sortase A-ELP$_{40}$, cleaved ELP$_{160}$ tag, and unreacted KEKE-ELP$_{160}$-srt-ABD-Dox by size exclusion chromatography using a Superdex 75 column (HiLoad 16/60 Superdex 75 prep grade) at 4° C. on a AKTA Purifier (both from GE Healthcare, Waukesha, WI) equipped with a photodiode detector set at 280 nm and 488 nm and using H$_2$O:PBS:acetonitrile (30:35:35 v/v) as the mobile phase.

Characterization of Dox conjugate The hydrodynamic radius (Rh) of the ELP$_{160}$-srt-ABD-Dox and KEKE-ELP$_{160}$-srt-ABD-Dox conjugates were determined by dynamic light scattering (DLS) (DynaPro; Wyatt Technology, Santa Barbara, CA) at 25° C. using a single detector at 90°. Samples were prepared in sortase reaction buffer at 25 µM, filtered through 0.22 µm Millex-GV filters (Sigma-Aldrich, St. Louis, MO) and measured using a Dynapro™ plate reader (Wyatt Technology, Santa Barbara, CA). The data were analyzed with a regularization fit of the autocorrelation function using a Rayleigh sphere model. The purity of the drug conjugates (KEKE-ELP$_{160}$-ABD-Dox and ABD-Dox) and efficiency of the sortase enzymatic reaction was assessed by size exclusion HPLC. Samples were injected into a LC10 HPLC (Shimadzu Scientific Instruments; Columbia, MD) with a Shodex OHPak SB-804 column (New York, NY) and PBS:acetonitrile (70:30 v/v) as the mobile phase at an isocratic flow rate of 0.3 mLmin$^{-1}$. Eluting peaks were detected with a UV-visible detector set at 488 nm. Mass spectrometry analysis of the ABD-Dox conjugate was performed on a Bruker Autoflex Speed MALD-TOF MS (Bruker Daltonics, Billerica, MA) using succinic acid matrix and porcine insulin as the internal standard.

Drug release Dox release from the ABD-Dox conjugate was measured at pH 7.4 and 5.0, corresponding to the physiological pH and late endosomal pH, respectively. ABD-Dox in PBS (400 µM Dox Equiv.) was diluted with an equal volume of either 0.1 M Na—$PO_4$, pH 7.4 buffer, 0.1 M Na-acetate, pH 5.0 buffer, incubated at 37° C. for 0, 0.25, 0.5, 1, 2, 4, 6, and 24 h, and neutralized using an equal volume of 0.1 M Na—$PO_4$, pH 7.4 buffer. Samples were then analyzed by size exclusion HPLC using the same chromatography conditions as described above for the characterization of Dox conjugates and the percentage of released Dox was calculated by integrating the area under the peak corresponding to unbound Dox. The cumulative percent released Dox (F %, released) versus time was fit to a first order release model: F %, released=$a[1-\exp(-\ln(2)t/t_{1/2})]$ where t is the time (h) after incubation, tia is the half-maximal release time (h), and a (%) is the maximum extent of drug release, using GraphPad Prism software (GraphPad, San Diego, CA).

Interaction of ABD-DOX with human and mouse albumin The affinity of ABD-Dox for mouse serum albumin (MSA) and human serum albumin (HSA) was studied qualitatively by native-PAGE electrophoresis and quantitatively by isothermal titration calorimetry. For native-PAGE, ABD-Dox was mixed with an equal number of moles of MSA and HSA, and incubated for 30 min at room temperature, prior to carrying out native PAGE. ABD-Dox, HSA, MSA, and mixtures of ABD-Dox with HSA and MSA were mixed with native-PAGE buffer, loaded onto stain-free gels and run at 180 V for 45 min using native-PAGE running buffer. The gel was stained with SimplyBlue stain according to the manufacturer's instructions and imaged using the Gel Doc imaging system (Bio-Rad, Hercules, CA). Isothermal titration calorimetry was done using a standard volume Nano ITC from TA instruments (Lindon, Utah). 250 µL of HSA or MSA at a 500 µM concentration in PBS was injected as 10 µL aliquots into the calorimeter cell containing 1 mL of 45 µM ABD-Dox in PBS at 37° C. with stirring. The heat of dilution was measured by injecting HSA or MSA in PBS into the PBS buffer without ABD-Dox under the same titration conditions and was subtracted from the heat of titration of ABD-Dox with HSA or MSA. The calorimetric data were analyzed by NanoAnalyze software (TA instruments, Lindon, UT) and were fit to an independent binding site model to compute the thermodynamic parameters including dissociation constant (KD), binding stoichiometry (n), enthalpy ($\Delta H$), and entropy ($\Delta S$).

Pharmacokinetics and biodistribution Pharmacokinetics and biodistribution experiments were performed to study the concentration of ABD-Dox in blood and tissues over time following intravenous (i.v.) administration. For the pharmacokinetic study, ABD-Dox and Dox in PBS and AlDox in 10 mM sodium phosphate, 5% D-(+)-glucose, pH 5.8 were injected at 5 mg Dox Equiv. per kg of body weight (BW) into healthy BALB/c mice. 10 µL blood samples were collected at 40 s, 15 min and 30 min, and 2, 4, 8, 24, 48, 72 and 96 h post injection and were diluted into heparinized PBS (1 $kUmL^{-1}$), and centrifuged at 4,000 rcf, 10 min, 4° C. to collect the plasma. 10 µL of the plasma samples were then diluted in 490 µL of acidified isopropanol (0.075 M HCl, 10% water) and incubated overnight at 4° C. For the biodistribution study, ABD-Dox and Dox in PBS were injected at 5 mg Dox Equiv.$kg^{-1}$ BW into C26 tumor-bearing BALB/c mice. At 2 h, 24 h, and 72 h post-injection, mice were sacrificed and tumor, heart, lung, liver, spleen, kidney and muscle tissues were dissected, weighed, homogenized in acidified isopropanol using a Mini-Beadbeater (Biospec, Bartlesville, OK) with 2 mm diameter zirconia beads for 1-2 min, and were incubated overnight at 4° C. Following overnight incubation in acidified isopropanol, plasma and tissue samples were centrifuged at 16,000 rcf, 4° C. for 10 min and the supernatants were loaded onto black 96-well plates in duplicate and the Dox fluorescence was measured using on a Victor3 microplate reader (Perkin Elmer, Waltham, MA) with fluorescence excitation at 485 nm and emission at 590 nm. Tissues were also dissected from three untreated mice, processed in the same manner, serially diluted, and loaded on the plates to prepare a standard curve of fluorescence intensity versus the weight for each tissue from which the background tissue fluorescence was calculated and subtracted for each sample. Serial dilution of free Dox in acidified isopropanol was used as standard to quantify the Dox concentration as pmoles per liter of plasma (µM) and as the percent of the injected dose per gram (% ID $g^{-1}$) in the tumor and other tissues. Plasma concentrations of Dox Equiv. of ABD-Dox versus time were fit to a two-compartment model using SAAM II software (SAAM Institute, Seattle, WA) and the elimination half-life and the area-under-curve were computed. The tissue concentration of Dox. Equiv. of ABD-Dox and free Dox at each time point were compared in GraphPad Prism software (GraphPad, San Diego, CA) by Student's t-test with P<0.05 considered statistically significant.

In vitro cytotoxicity C26 murine colon carcinoma cells and three different pancreatic cancer cell lines, BxPC-3, AsPC-1, and MIA PaCa-2, were used to study the in vitro cytotoxicity of ABD-DOX and Dox. Cells were cultured and grown as monolayers at 37° C. with C02 in a humidified incubator and were passaged at ~80% confluency using 0.05% trypsin-EDTA (Invitrogen, Carlsbad, CA). C26, BxPC-3, AsPC-1, and MIA PaCa-2 cells were seeded in 96-well plates (5,000 cells/well) and incubated overnight. Three-fold serial dilutions of drug were then added to the wells in triplicate and also to control wells (media with no cells) to correct for the background Dox absorbance. After 72 h treatment, 20 µL MTS reagent was added to each well and was incubated for 3 h at 37° C., and the absorbance at 490 nm was measured using a Victor3 plate reader (Perkin Elmer, Boston, MA). Cell viability (%) was defined as the percentage of the absorbance of the drug-treated cells relative to buffer-treated cells and $IC_{50}$ values were determined using logistic non-linear regression analysis with GraphPad Prism software. The $IC_{50}$ was defined as the Dox Equiv. concentration of formulations resulting in 50% growth inhibition compared with a negative control, buffer-treated cells.

In vivo tumor regression For in vivo tumor implantation, C26 cells at $5 \times 10^5$ cells in 30 µL Minimum Essential Medium (MEM) (Invitrogen, Carlsbad, CA) and MIA PaCa-2 cells at $2 \times 10^6$ cells in 50 µL 10:90 v/v MEM: Matrigel matrix (Corning Inc, Corning, New York) were inoculated in the right flank of normal and athymic nude BALB/c mice, respectively. Tumor cells were allowed to grow until the tumor volume, calculated as $\pi/6 \times length \times width^2$, reached 75-100 $mm^3$ for C26 tumors and 100-125 $mm^3$ for MIA PaCa-2 tumors. Tumor bearing mice were then treated with ABD-Dox at 10 and 20 mg Dox Equiv.$kg^{-1}$ BW, AlDox at 20 mg Dox Equiv.$kg^{-1}$ BW, and free Dox at 10 $mgkg^{-1}$ BW. Tumor volumes and body weights were monitored for 100 days after treatment and mice displaying excessive tumor volume (>2000 mm), body weight loss (>15%), or ill health were euthanized. Tumor growth and survival data were analyzed by GraphPad Prism software. Survival curves were generated with the Kaplan-Meier method and compared with the log-rank (Mantel-Cox) test.

Tumor growth data were compared with a paired one-way ANOVA followed by Tukey-Kramer (Tukey's) post-hoc test. P<0.05 was considered as statistically significant.

Example 2: AlBiPeDs Synthesis and Purification

The ABD used here was a 46 amino acid, three-helix protein domain from streptococcal protein G. It shows a high stability with respect to both temperature (Tm~72° C.) and pH, has high aqueous solubility and can be easily produced recombinantly at a high level by overexpression in E. coli. In addition, it binds to albumin from different species allowing for a plethora of animal models to be used for preclinical studies. All of these properties make the ABD desirable for pharmaceutical formulations. In addition, ABD does not contain any cysteine residues and therefore does not interfere with the C-terminal cysteine-containing drug conjugation site used in our synthesis scheme.

The design of the construct from the N- to C-terminus is as follows: (1) a peptide with the sequence KEKE (SEQ ID NO: 5); (2) an elastin-like polypeptide (ELP); (3) a sortase A cleavage site with the amino acid sequence, LPETG (SEQ ID NO:6), that is named srt; (4) the ABD; and (5) a $(GGC)_4$ or $(GGC)_8$ (SEQ ID NO:3) peptide for site-specific conjugation of Dox (FIG. 2A). ELPs are recombinant polypeptides composed of repeats of the pentapeptide (Val-Pro-Gly-Xaa-Gly)$_p$ (SEQ ID NO:4) where Xaa is the guest residue and can be any amino acid except proline, and p is the number of pentapeptide repeats. ELPs are thermally responsive polypeptides and undergo a lower critical solution temperature (LCST) phase transition. ELPs retain this behavior when fused to other peptides and proteins. An ELP was chosen because it can promote high levels of soluble protein expression, and importantly an ELP can be used as a purification tag to isolate recombinant ELP-fused peptides and proteins from cell contaminants by cycling the soluble fraction of the cell lysate through the insoluble and soluble phases by a chromatography-free method known as inverse transition cycling. The ELP used here consists of 160 repeats of the VPGAG (SEQ ID NO: 7) pentapeptide (denoted here as $ELP_{160}$).

Because the desired final product was an ABD-Dox conjugate, the srt sequence was added between $ELP_{160}$ and ABD to remove the $ELP_{160}$ tag by cleavage with sortase A. Two drug conjugation segments downstream of the ABD, $(CGG)_4$ and $(CGG)_8$, were chosen to provide four or eight cysteine residues as Dox attachment sites. Early studies found that attachment of Dox to the ELP-ABD fusions led to the formation of micelles (FIG. 2C), which was undesirable because micelle formation buries the sortase cleavage site within the micelle, making cleavage with sortase A inefficient. The alternative of first cleaving the ELP from the fusion, prior to Dox conjugation, was problematic as the size and physicochemical differences between ABD-Dox and Dox makes their separation by centrifugal ultrafiltration or chromatography difficult.

To prevent the self-assembly of ELP-ABD-Dox conjugates into micelles, a zwitterionic KEKE (SEQ ID NO: 5) peptide was incorporated at the N-terminus of the construct, as it was previously shown to be a potent destabilizer of ELP micelles. Following gene synthesis, the plasmid encoding KEKE-$ELP_{160}$-srt-ABD-$(CGG)_{4/8}$ was transformed into E. coli BL21(DE3) cells. The cells were allowed to grow for 6-8 h at 37° C. following which the fusion was expressed by addition of 1 mM isopropyl-β-d-thiogalactopyranoside (IPTG). The fusion was purified from the soluble fraction of the E. coli lysate by two rounds of inverse transition cycling (FIG. 2B) at a yield of 75-100 mg protein per liter culture.

To remove the ELP tag from $ELP_{160}$-ABD, sortase A was fused to an N-terminal tag comprised of 6 histidine residues (His-tag) and a C-terminal ELP tag comprised of 40 repeats of a VPGAG (SEQ ID NO: 4) pentapeptide ($ELP_{40}$) (FIG. 2A). The ELP was appended at the C-terminus of sortase A to increase its molecular weight from 18 kDa to 34 kDa to facilitate its separation from the ABD-Dox product that has a molecular weight (MW) of 8 kDa, following the sortase cleavage reaction by size exclusion chromatography (SEC). The $(His)_6$-sortase A-$ELP_{40}$ fusion was transformed into and expressed in E. coli BL21(DE3) cells and was successfully isolated from cell contaminants by immobilized metal affinity chromatography with a yield of ~100 mg per liter of culture.

For drug conjugation, Dox was conjugated with 3,3'-N-(ε-maleimidocaproic acid) hydrazide (EMCH) and the resulting Dox-EMCH conjugate was reacted with the free thiols of the Cys residues of the $(CGG)_{4/8}$ segment at the C-terminus of KEKE-$ELP_{160}$-srt-ABD-$(CGG)_{4/8}$. Free Dox was removed by ultracentrifugation (FIG. 3A). Dynamic light scattering (DLS) confirmed that the KEKE-$ELP_{160}$-srt-ABD-Dox conjugates were mostly unimers (Rh<10 nm) so that the sortase cleavage site should be accessible to sortase A, whereas $ELP_{160}$-srt-ABD-Dox without the N-terminal KEKE segment self-assembled into micelles with a Rh of 40-50 nm (FIG. 2C) with the ABD-Dox and the srt sortase cleavage site presumably buried in the core of the micelle.

To remove the $ELP_{160}$ tag, the KEKE-$ELP_{160}$-srt-ABD-Dox conjugate was buffer exchanged into sortase reaction buffer, and was reacted with $(His)_6$-sortase A-$ELP_{40}$ in the presence of a 50 fold molar excess of triglycine (FIG. 2A). The efficiency of the sortase reaction, defined as the percent conversion of ELP-ABD-Dox substrate to ABD-Dox, was determined by size exclusion HPLC and was calculated to be ≥85% (FIG. 3A). The ABD-Dox product was then separated from $(His)_6$-sortase A-$ELP_{40}$, the cleaved KEKE-$ELP_{160}$ tag, and unreacted KEKE-$ELP_{160}$-srt-ABD-Dox in the sortase reaction solution by preparative size exclusion chromatography (SEC). The number of Dox molecules conjugated per ABD (Dox/ABD molar ratio) was measured before the sortase reaction by dissolving the lyophilized KEKE-$ELP_{160}$-srt-ABD-Dox conjugate in PBS and calculating the moles of KEKE-$ELP_{160}$-srt-ABD-Dox and Dox gravimetrically and spectrophotometrically at 488 nm, respectively. 3-4 Dox molecules were attached to each KEKE-$ELP_{160}$-srt-ABD-$(CGG)_8$. However, following removing the $ELP_{160}$ tag, the resulting ABD-Dox conjugate was too hydrophobic and insoluble in pH 7.4 PBS because of the high number of conjugated Dox molecules. In contrast, only 1-2 Dox molecules were attached to KEKE-$ELP_{160}$-srt-ABD-$(CGG)_4$, and this ABD-Dox conjugate showed aqueous solubility up to 4 mg Dox Equiv.$mL^{-1}$ in pH 7.4 PBS and was hence used for further studies. The site-specific ABD-Dox conjugate had a better solubility profile compared with AlDox, which shows poor solubility at physiological pH and requires an acidic pH for solubility in aqueous solutions at concentrations as low as 0.5 mg Dox Equiv.$mL^{-1}$. Formulation of AlDox in acidic pH, however, is undesirable as it can trigger the premature, in vitro degradation of the hydrazone bond between Dox and EMCH, converting AlDox back to free Dox.

The attachment of 1-2 Dox molecules to ABD-$(CGG)_4$ was confirmed by MALDI-TOFMS that gave a broad peak centered around 7813 and 8563 m/z that corresponds to the theoretical MW of ABD-(CGG)$_4$-Dox with 1 and 2 conjugated Dox molecules ("ABD-Dox"), respectively.

The interaction of ABD-Dox with albumin was confirmed qualitatively by native-PAGE and quantitatively by isothermal titration calorimetry. Human serum albumin (HSA) and mouse serum albumin (MSA) are negatively charged and migrate toward the cathode in native-PAGE. ABD-Dox however did not migrate on the native PAGE gel, and when mixed with HSA and MSA, hindered their mobility resulting in higher and smeared bands compared with free HSA and MSA bands (FIG. 3D). This mobility shift confirmed binding of ABD-Dox to HSA and to MSA. The thermodynamics of the interaction was studied by isothermal titration calorimetry, and the binding isotherms were fit using an independent binding site model and yielded an equilibrium dissociation constant ($K_D$) of 125 nM and 73.8 nM, and a stoichiometry (n) of 1.03 and 0.94 for HSA and MSA, respectively (FIG. 3E, Table 1). These nanomolar dissociation constants indicated that ABD-Dox has a high affinity for both HSA and MSA. Given the high concentration of albumin in plasma (~0.6 mM), these results suggested that the ABD-Dox conjugates will largely exist as an albumin bound complex in murine or human circulation.

TABLE 1

Thermohydnamic parameters of the binding of ABD-Dox to human serum albumin (HAS) and mouse serum albumin (MSA)

|  | n | $K_D$ (nM) | ΔH (kJ · mol$^{-1}$) | ΔS (Jmol$^{-1}$K$^{-1}$) |
| --- | --- | --- | --- | --- |
| ABD-Dox:HSA | 1.0 | 125 | −28.1 | 41.5 |
| ABD-Dox:MSA | 0.9 | 73.8 | −18.6 | 76.6 |

Example 3: ABD-Dox Release Dox at Acidic pH

The release of Dox from the ABD-Dox conjugate was studied at the physiological pH of 7.4 and the late endosomal pH of 5.05. Dox release was negligible at pH 7.4, whereas at pH 5.0, about 70% of the drug was released over 24 h (FIG. 3C), which was attributed to the pH-sensitive hydrolysis of the hydrazone bond between Dox and EMCH linker. The release data at pH 5.0 was fit to a first-order release model, from which 50% of the total release ($t_{1/2}$) was calculated to occur within 2.8 h at pH 5.0. The pH-dependent release of Dox from ABD-Dox prevents systemic toxicity of ABD-Dox as it prevents premature release of Dox in the blood and the extracellular space of healthy tissues where the pH is 7.4.

Example 4: Albumin Binding Prolongs the Circulation Time of AlBiPeDs

The intravenous (i.v.) pharmacokinetics of ABD-Dox was compared with that of AlDox and free drug. ABD-Dox, AlDox and Dox were injected i.v. at a dose of 5 mg Dox Equiv. per kg of body weight (BW) into healthy BALB/c mice and the Dox fluorescence was measured from blood samples collected at different time points following i.v. injection to quantify the Dox Equiv. concentration in plasma as a function of time. Free Dox has an in vivo elimination half-life on the order of minutes, with a systemic clearance that was so fast that 15 min after i.v. injection, the concentration of Dox in blood was less than 2% of the initial concentration (FIG. 4A). In contrast, ABD-Dox had a much longer elimination half-life of 29.4±0.8 h that was close to the previously reported 35 h half-life of MSA53, resulting in the drug being detectable in plasma even 96 h after injection (FIG. 4B). The elimination half-life of AlDox was 21.3±0.6 h, shorter than the 29.4±0.8 h half-life of ABD-Dox (P<0.001, Student's t-test). The impact of this difference in the half-life on pharmacokinetics is relevant, as 15 min after i.v. injection, the concentration of AlDox was ~2-fold lower than that of ABD-Dox (P<0.05, one-way ANOVA and Tukey's test) (FIG. 4A), which could be the result of a reaction of AlDox with thiols and lysines on blood cells leading to some loss from the plasma compartment of blood. Finally, total plasma exposure, as defined by the area under the curve, of ABD-Dox was 2263.6±44.7 µM·h, which was 3-fold higher than that of AlDox (801.2±23.7 µM·h) and was statistically different (P<0.001, Student's t-test). These results demonstrated that the use of a peptide that binds albumin via molecular recognition is superior to a Dox derivative, Aldoxorubicin, that piggybacks on to albumin by virtue of its preferential chemical reactivity with albumin.

TABLE 2

Pharmacokinetic parameters of ABD-Dox. Values are shown as mean ± SD.

| Pharmacokinetic Parameter | ABD-Dox | AlDox |
| --- | --- | --- |
| Elimination half-life (h) | 29.4 ± 0.8 | 21.3 ± 0.6 |
| Area under curve (µM · h) | 2263.6 ± 44.7 | 801.2 ± 23.7 |

Example 5: Albumin Binding Improves Targeting and Biodistribution Profile

To study the biodistribution and tumor localization of ABD-Dox, tumor and major tissues were harvested at 2 h, 24 h, and 72 h post injection and the concentration of the Dox Equiv. at each time point was measured and compared with animals injected with the same dose of free Dox. Within 2 h after administration, the concentration of ABD-Dox was 6.2% ID.g$^{-1}$ of Dox equivalent in the tumor, which is 4-fold greater than the accumulation of free Dox (P<0.001, Student's t-test). Longer term, at 24 h and 72 h, the tumor accumulation of ABD-Dox reached ~8% ID.g$^{-1}$. In contrast to ABD-Dox, which showed steady levels DOX accumulation over 72 h, the accumulation of free Dox decreased over 72 h, with a maximum of 1.6% ID.g$^{-1}$ at 2 h and a minimum of 0.07% ID.g$^{-1}$, indicating that much of the initial accumulation of free drug is transient. This level of accumulation of ABD-Dox, especially at 72 h was notable, as it was ~120-fold greater than that of the free drug (FIG. 5A).

At 2 h post-administration, ABD-Dox accumulated at a lower concentration in liver (P<0.05, Student's t-test), kidneys (P<0.05, Student's t-test), spleen (P<0.001, Student's t-test), and muscle (P<0.01, Student's t-test) (FIG. 6). Furthermore, compared with the tumor, where ABD-Dox continued to accumulate for at least 72 h (FIG. 5A), the concentration in other tissues, with the exception of spleen and muscle, decreased over time. At 24 h after administration, compared to free Dox, ABD-Dox had a lower concentration in spleen (P<0.001, Student's t-test), but higher concentration in heart (P<0.05, Student's t-test), lungs (P<0.01, Student's t-test), liver (P<0.01, Student's t-test), and muscle (P<0.001, Student's t-test) (FIG. 6). At 72 h, the accumulation of ABD-DOX was higher in lungs (P<0.001, Student's t-test), liver (P<0.05, Student's t-test), kidneys (P<0.05, Student's t-test), and muscle (P<0.05, Student's t-test) (FIG. 6).

As the biodistribution data for ABD-Dox and free Dox (control) was collected at three time points spanning 2 to 72 h post administration, it allowed the total exposure of different tissues over time to be determined by calculating the area under the curve (AUC) of the Dox Equiv. concentration for each formulation. ABD-Dox showed significantly higher, 16-fold, greater AUC in the tumor and ~50% lower AUC in the spleen compared to free Dox. No significant difference was observed between the AUC of ABD-Dox and free Dox in other tissues (FIG. 5A). The lower AUC of ABD-Dox than free Dox in the spleen was consistent with the ability of albumin to reduce opsonization, which reduces subsequent uptake by macrophages that are present at a high level in the spleen, while also directing cellular uptake of albumin and its conjugates via FcRn receptors in the liver and spleen that then recycle albumin in these organs back into systemic circulation.

The significantly greater drug exposure solely in the tumor afforded by ABD-Dox compared with free Dox was of clinical significance as it showed that that the long circulating ABD-Dox conjugate targeted the tumor to a far higher level than the free drug, and suggested that this formulation may achieve therapeutic levels of drug in the tumor. The biodistribution results also suggested that this formulation should not intensify cardiotoxicity, hepatotoxicity, and nephrotoxicity, which are the major side effects associated with free Dox.

Example 6: Binding to Albumin Enhances the Tumoricidal Effect

With these encouraging biodistribution results in hand, tumor regression in vivo by ABD-Dox was investigated. The maximum tolerated dose (MTD) of ABD-Dox was established in healthy mice. A range of doses of ABD-Dox were injected into healthy BALB/c mice, and body weight loss and mortality of the mice were monitored over a two-week period to assess systemic toxicity. The MTD was defined as the highest dose that did not cause mortality or body weight loss greater than 15% in any of the mice. Using these criteria, the MTD was determined to be 20 mg Dox Equiv.kg$^{-1}$ for ABD-Dox (FIG. 7) and 10 mgkg$^{-1}$ BW MTD of free Dox (FIG. 8).

Next, tumor regression studies were performed in a syngeneic model of murine colon carcinoma (C26) and in a xenograft model of human pancreatic adenocarcinoma (MIA PaCa-2). These tumor lines were chosen for several reasons: First, inclusion of a human-derived cancer cell line was desired for clinical relance, but this required use of immunocompromised mice for tumor implantation, and one mouse-derived cancer cell line that allowed use of immunocompetent mice was chosen as previous studies showed that host immunity can contribute to the therapeutic efficacy of doxorubicin formulations. Second, both C26 and MIA PaCa-2 respond poorly to doxorubicin treatment in vivo, so they were a stringent test of the utility of the ABD-Dox formulation in enhancing the efficacy of the drug. Third, in an in vitro scouting study to identify the most promising pancreatic cancer for treatment by ABD-Dox, of the three human pancreatic cell lines, MIA Paca-2, AsPC-1 and BxPC-3, treated with ABD-Dox, MIA Paca-2 was the most sensitive to ABD-Dox (FIG. 3F and FIG. 9) and was therefore selected as a candidate for in vivo studies.

Prior to in vivo regression studies, the efficacy of ABD-Dox against C26 and MIA PaCa-2 tumor cells was first investigated in vitro. The half-maximal inhibitory concentration ($IC_{50}$) of ABD-Dox was 6.4 µM and 1.4 µM for C26 and MIA PaCa-2 cells, respectively. In contrast the $IC_{50}$ of free Dox was 0.5 µM and 0.04 µM for C26 and MIA PaCa-2 cells, respectively (FIG. 3F). Although the in vitro cytotoxicity of ABD-DOX was 10-30 fold lower than that of free Dox, based on previous experience with Dox loaded into nanoparticles, this level of cytotoxicity was significant and acceptable, as the extended half-life and greater tumor accumulation of ABD-Dox compared with free Dox was hypothesized to more than compensate for its lower cytotoxicity, in vivo.

For in vivo tumor regression studies, a single dose of ABD-Dox was injected via tail vein at 10 mg Dox Equiv.kg$^{-1}$ BW (MTD of free Dox) and 20 mg Dox Equiv.kg$^{-1}$ BW (MTD of ABD-Dox) in separate cohorts of BALB/c mice with s.c. C26 tumors or nude mice with s.c. MIA Paca-2 tumors. Free Dox was injected at its MTD of 10 mgkg-1 BW, and AlDox was injected at 20 mg Dox Equiv.kg$^{-1}$ BW, a dose that was reported to be safe in previous studies. All animals were injected when the tumors were 75-100 mm; in size for C26 tumors and 100-125 mm$^3$ for MIA PaCa-2 tumors. Tumor growth was monitored over 100 days after treatment, with predetermined endpoints for euthanasia, when the tumor volume exceeded 2000 m$^3$, body weight loss exceeded 15%, or if animals showed signs of morbidity including hunching, limb paralysis, and fur ruffling, as examined and determined by the veterinary staff at the Duke Cancer Center Isolation Facility.

In the colon carcinoma C26 tumor model, ABD-Dox at both 10 and 20 mg Dox Equiv.kg$^{-1}$ BW doses showed superior efficacy to free Dox (dose of 10 mgkg$^{-1}$ BW) with respect to both tumor regression (P<0.001, paired one-way ANOVA and Tukey's test) (FIG. 10A) and survival (P<0.001, log-rank (Mantel-Cox) test) (FIG. 10B). At 20 mg Dox Equiv.kg$^{-1}$ BW, both ABD-Dox and AlDox treatments resulted incomplete eradication of C26 tumors, without recurrence of the primary tumor in any mice. At 10 mg Dox Equiv.kg$^{-1}$ BW, ABD-Dox showed complete tumor disappearance within 2 weeks after injection, but tumor recurrence was observed in 33% of mice with eradicated tumors. 75% and 25% of the mice in the ABD-Dox and AlDox arms (both at 20 mg Dox Equiv.kg$^{-1}$ BW), respectively, did not survive over the 100-day course of study (FIG. 10B) due to either poor body conditions or body weight loss exceeding 15%, presumably caused by metastasis of the primary tumor. Therefore, the therapeutic efficacy of ABD-Dox was equivalent to AlDox with respect to tumor regression, but was higher in terms of overall survival (P<0.05, log-rank (Mantel-Cox) test).

In the pancreatic MIA PaCa-2 tumor model, ABD-Dox treatment at 20 mg Dox Equiv.kg$^{-1}$ BW resulted in significantly longer survival compared with treatment with free Dox (P<0.05, log-rank (Mantel-Cox) test). No significant difference was found between ABD-Dox and free Dox at 10 mg Dox Equiv.kg$^{-1}$ BW dose and between ABD-Dox and AlDox arms at 20 mg Dox Equiv.kg$^{-1}$ BW dose (FIG. OD). ABD-Dox, however, showed superior tumor regression efficacy (P<0.05, paired one-way ANOVA and Tukey's test) (FIG. 10C) and a longer tumor-free period (P<0.001, one-way ANOVA and Tukey's test) (FIG. 1E) compared with AlDox at the same dose 20 mg Dox Equiv.kg-1 BW dose. By day 15 after treatment, all of ABD-Dox-treated mice, but only 50% for AlDox-treated mice showed tumor disappearance. Furthermore, by day 50, tumors recurred in all of the tumor-eradicated mice in the AlDox arm, while in the 20 mg Dox Equiv.kg$^{-1}$ BW ABD-Dox treatment group, tumors reoccurred in only 25% of the tumor-eradicated mice throughout the 100 day course of study.

In aggregate, these results show that ABD-Dox has superior therapeutic efficacy to AlDox in the syngeneic C26 colon carcinoma model in BALB/c mice and in the MIA PaCa-2 pancreatic adenocarcinoma xenograft model in nude mice, and that both formulations are superior to free Dox. This is the first report showing that a conjugate of doxorubicin with an albumin binding protein domain provides a 16-fold greater drug exposure in tumor than the free drug formulation, a 2-fold higher maximum tolerated dose, and results in complete tumor eradication and prolonged survival with a single injection. There was one published report of a somewhat different system that consists of doxorubicin conjugated to an albumin binding domain fused to tumor-penetrating sequences, but despite the apparent sophistication of the design, it failed to exhibit any tumor regression, highlighting the fact that careful design of a delivery system is critical to success.

In addition, these highlight that in vitro tumor cytotoxicity does not predict in vivo therapeutic efficacy, as it does not account for the important role of physiological transport barriers in vivo that control tumor exposure, and hence efficacy. In fact, despite a 10-30 fold lower anti-tumor cytotoxicity compared with free Dox in vitro, ABD-Dox showed far superior tumoricidal efficacy in vivo. In addition, ABD-Dox was more efficacious in the C26 model that showed less sensitivity to ABD-Dox and free Dox in vitro than MIA PaCa-2 and resulted in significant tumor regression and a higher survival rate compared with free Dox in this tumor model even at the lower dose of 10 mg Dox Equiv.kg$^{-1}$ BW. The higher therapeutic efficacy of ABD-Dox in the C26 allografts compared with MIA PaCa-2 xenografts was likely due to a cellular immune response triggered by treatment with ABD-Dox in this immunocompetent model, resulting in immunogenic cell death in addition to direct tumor cytotoxicity caused by the drug.

Example 7: Comparison of Albumin Binding Domains

To compare the effects of different albumin binding domains on the characteristics of the AlBiPeD conjugates, two conjugates were made; one comprising ABDN and one comprising ABDH. Dox was loaded on both conjugates at ≤1 drug/ABD.

ABDN-Dox and ABDH-Dox were purified by two methods; size exclusion chromatography and ultrafiltration (Post-AKTA and PostAmicon in FIG. 11, respectively). With both purification methods, ABDH-Dox (FIG. 11, blue and green chromatograms) showed multiple peaks instead of a single peak. ABDH-Dox was interacting with column resin and not eluting normally as most one main peak. ABDN-Dox (FIG. 11, black and yellow chromatograms) eluted out of column normally and showed a clean sharp peak at approximately 32 minutes. The second smaller peak corresponded to any remaining uncleaved ELP-ABD-Dox.

These results indicated that ABDH-Dox had a higher hydrophobicity than ABDN-Dox. Thus, these results provided evidence that ABDN-Dox is more soluble and has a decreased propensity to form aggregates than ABDH. Therefore, in a conjugate with Dox, ABDN is the preferred form of ABD.

To address any potential immunogenicity concerns, a deimmunized ABD variant (ABD094) was generated by mutagenesis of the ABD sequence by substitution of the T-cell epitope residues located within the ABD. In T-cell proliferation assays, this variant showed a very week immunogenic response (Affibody AB). Of note, in preclinical studies, ABD used in previous experiments were well-tolerated in repeated administrations and ABD fusions have even been shown to reduce the immunogenicity of a fused protein.

The albumin binding strategy developed in this work could be readily applied to other small molecule anticancer drugs such as gemcitabine, paclitaxel, and fluorouracil whose clinical application is limited by their poor pharmacokinetic or pharmacodynamic profiles. In addition, small active targeting protein domains such as affibodies or Fn3 domains that are readily overexpressed in E. coli may be recombinantly fused to the ABD to yield actively targeted, long-circulating drug conjugates to further enhance tumor localization and therapeutic efficacy. In conclusion, the system demonstrated here allowed site-specific conjugation of chemotherapeutics to an ABD that is readily overexpressed in E. coli and purified with high yield and purity without the need for chromatography. This system may also enable other functional elements, such as targeting protein domains, to be easily incorporated at the gene level to yield a modular and flexible system for delivery of small molecule drugs to tumors for cancer therapy.

For reasons of completeness, various aspects of the invention are set out in the following numbered clauses:

Clause 1. A composition comprising: an albumin binding domain (ABD); a linker coupled to the ABD; and at least one molecule coupled to the linker.

Clause 2. The composition of clause 1, wherein the ABD comprises SEQ ID NO:1

Clause 3. The composition of clause 1 or clause 2, wherein the linker comprises a cysteine, and the at least one molecule is coupled to the cysteine.

Clause 4. The composition of any one of clauses 1-3, wherein the linker comprises an amino acid sequence of (CGG)$_z$ (SEQ ID NO:3), wherein z is greater than 1 and wherein the linker is conjugated to the N or C terminus of the ABD.

Clause 5. The composition of clause 4, wherein z is 4 or 8.

Clause 6. The composition of any one of clauses 1-5, wherein the at least one molecule is attached to the linker through a pH labile bond.

Clause 7. The composition of any one of clauses 1-6, wherein the at least one molecule is attached to the linker through a hydrazone bond.

Clause 8. The composition of any one of clauses 1-7, wherein the at least one molecule is a chemotherapeutic or an imaging agent.

Clause 9. The composition of any one of clauses 1-8, wherein the at least one molecule is doxorubicin.

Clause 10. The composition of any one of clauses 1-9, wherein the at least one molecule has an octanol-water distribution coefficient (log D) of greater than or equal to 1.5 at a pH of 7.4 when the molecule is not attached to the ABD.

Clause 11. The composition of any one of clauses 1-10, wherein the at least one molecule comprises one or two of the molecules.

Clause 12. A method of killing cancer cells comprising contacting cancer cells with an effective amount of the composition of any of clauses 1-11.

Clause 13. A method of treating a disease or disorder in a subject comprising administering to the subject a therapeutically effective amount of the composition of any of clauses 1-11.

Clause 14. The method of clause 13, wherein the disease or disorder is cancer.

Clause 15. A method of purifying the composition of clause 1, comprising forming a conjugate comprising, an elastin-like polypeptide having a transition temperature ($T_t$) above 50° C.; and the composition of claim 1, wherein the composition is conjugated to a first end of the elastin-like polypeptide by an amino acid sequence amenable to cleavage; treating the conjugate with an enzyme, chemical, or combination thereof capable of cleaving the amino acid sequence amenable to cleavage; and separating the composition from the elastin-like polypeptide.

Clause 16. The method of clause 15, further comprising a destabilizing peptide conjugated to a second end to an elastin-like polypeptide.

Clause 17. The method of clause 16, wherein the destabilizing peptide comprises SEQ ID NO: 5.

Clause 18. The method of any of clauses 15-17, wherein the amino acid sequence is amenable to cleavage by an enzyme, wherein the enzyme is Sortase A.

Clause 19. The method of any of clauses 15-18, wherein the amino acid sequence amenable to cleavage comprises SEQ ID NO: 6.

Clause 20. The method of any of clauses 15-19, wherein the elastin-like polypeptide comprises an amino acid sequence of (VPGXaaG)$_p$(SEQ ID NO: 4), wherein Xaa is any amino acid except proline and p is 1 to 500.

Clause 21. The method of clause 20, wherein Xaa is alanine and p is 160.

Various features and advantages of the invention are set forth in the following claims.

What is claimed is:

1. A composition comprising:
   an albumin binding domain (ABD) consisting of the amino acid sequence of SEQ ID NO:1;
   a linker coupled to the ABD at the C terminus of the ABD, the linker consisting of the amino acid sequence of $(CGG)_z$ (SEQ ID NO:3), wherein z is selected from the group consisting of 1, 2, 3, and 4, wherein if there is more than one sequence of CGG, the amino acid sequence, wherein the N terminus cysteine of the linker is coupled to the C terminus ABD is repeated sequentially;
   one or two chemotherapeutic molecules selected from the group consisting of doxorubicin, paclitaxel, and docetaxel;
   wherein the one or two chemotherapeutic molecules are individually coupled to a cysteine thiol of the amino acid sequence of CGG through a 3,3'-N-[ε-maleimidocaproic acid] hydrazide moiety; and
   wherein the composition has an aqueous solubility of up to 4 mg of molecule equivalent/mL.

2. The composition of claim 1, wherein the molecule is doxorubicin.

3. A method of killing cancer cells comprising contacting cancer cells with an effective amount of the composition of claim 1, wherein the cancer cells are colon cancer cells or pancreatic cancer cells.

4. A method of treating a cancer in a subject comprising administering to the subject a therapeutically effective amount of the composition of claim 1, wherein the cancer is colon cancer or pancreatic cancer.

5. A method of purifying the composition of claim 1, comprising
   forming a conjugate comprising, an elastin-like polypeptide having a transition temperature $(T_t)$ above 50° C.; and the composition of claim 1, wherein the composition is conjugated to a first end of the elastin-like polypeptide by an amino acid sequence amenable to cleavage;
   treating the conjugate with an enzyme, chemical, or combination thereof capable of cleaving the amino acid sequence amenable to cleavage; and
   separating the composition from the elastin-like polypeptide.

6. The method of claim 5, further comprising a destabilizing peptide conjugated to a second end to an elastin-like polypeptide, wherein the destabilizing peptide comprises SEQ ID NO: 5.

7. The method of claim 5, wherein the amino acid sequence is amenable to cleavage by an enzyme, and wherein the enzyme is Sortase A.

8. The method of claim 5, wherein the amino acid sequence amenable to cleavage comprises SEQ ID NO: 6.

9. The method of claim 5, wherein the elastin-like polypeptide comprises the amino acid sequence of $(VPGXaaG)_p$ (SEQ ID NO: 4), wherein Xaa is any amino acid except proline and p is 1 to 500.

10. The method of claim 9, wherein Xaa is alanine and p is 160.

* * * * *

```
                        SEQUENCE LISTING

<160> NUMBER OF SEQ ID NOS: 8

<210> SEQ ID NO 1
<211> LENGTH: 46
<212> TYPE: PRT
<213> ORGANISM: Artificial Sequence
<220> FEATURE:
<223> OTHER INFORMATION: Synthetic

<400> SEQUENCE: 1

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Asn Ala Lys Thr Val Glu
            20                  25                  30

Gly Val Lys Ala Leu Ile Asp Glu Ile Leu Ala Ala Leu Pro
        35                  40                  45

<210> SEQ ID NO 2
<211> LENGTH: 46
<212> TYPE: PRT
<213> ORGANISM: Artificial Sequence
<220> FEATURE:
<223> OTHER INFORMATION: Synthetic

<400> SEQUENCE: 2

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Lys Ala Lys Thr Val Glu
            20                  25                  30

Gly Val Glu Ala Leu Lys Leu His Ile Leu Ala Ala Leu Pro
        35                  40                  45

<210> SEQ ID NO 3
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: the sequence Cys Gly Gly at positions 1 through
      3 repeats two or more times

<400> SEQUENCE: 3

Cys Gly Gly
1

<210> SEQ ID NO 4
```

```
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: the sequence Val Pro Gly Xaa Gly at positions 1
      through 5 may repeat from 1 to 500 times
<220> FEATURE:
<221> NAME/KEY: Xaa
<222> LOCATION: (4)..(4)
<223> OTHER INFORMATION: Xaa at position 4 is any amino acid except
      proline

<400> SEQUENCE: 4

Val Pro Gly Xaa Gly
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic

<400> SEQUENCE: 5

Lys Glu Lys Glu
1

<210> SEQ ID NO 6
<211> LENGTH: 5
<212> TYPE: PRT
<213> ORGANISM: Artificial Sequence
<220> FEATURE:
<223> OTHER INFORMATION: Synthetic

<400> SEQUENCE: 6

Leu Pro Glu Thr Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic

<400> SEQUENCE: 7

Val Pro Gly Ala Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: Xaa
<222> LOCATION: (3)..(3)
<223> OTHER INFORMATION: Xaa at position 3 is any amino acid

<400> SEQUENCE: 8

Leu Pro Xaa Thr Gly
1               5
```